United States Patent
Davies et al.

(10) Patent No.: US 9,604,940 B2
(45) Date of Patent: Mar. 28, 2017

(54) 2-AMINOPYRAZINE DERIVATIVES AS CSF-1R KINASE INHIBITORS

(71) Applicant: Chroma Therapeutics Ltd., Abingdon, Oxfordshire (GB)

(72) Inventors: Stephen John Davies, Abingdon (GB); Stephane Pintat, Abingdon (GB); Carl Leslie North, Abingdon (GB); David Festus Charles Moffat, Abingdon (GB)

(73) Assignee: Chroma Therapeutics Ltd., Abingdon, Oxfordshire (GB)

( * ) Notice: Subject to any disclaimer, the term of this patent is extended or adjusted under 35 U.S.C. 154(b) by 46 days.

(21) Appl. No.: 14/411,024

(22) PCT Filed: Jun. 26, 2013

(86) PCT No.: PCT/GB2013/051693
§ 371 (c)(1),
(2) Date: Dec. 23, 2014

(87) PCT Pub. No.: WO2014/001802
PCT Pub. Date: Jan. 3, 2014

(65) Prior Publication Data
US 2015/0368210 A1     Dec. 24, 2015

(30) Foreign Application Priority Data

Jun. 26, 2012   (GB) .................... 1211310.6

(51) Int. Cl.
| | | |
|---|---|---|
| A61K 31/4965 | (2006.01) | |
| C07D 241/20 | (2006.01) | |
| C07D 401/12 | (2006.01) | |
| C07D 403/12 | (2006.01) | |
| C07D 401/14 | (2006.01) | |
| C07D 403/10 | (2006.01) | |
| C07D 403/04 | (2006.01) | |

(52) U.S. Cl.
CPC ......... *C07D 241/20* (2013.01); *C07D 401/12* (2013.01); *C07D 401/14* (2013.01); *C07D 403/04* (2013.01); *C07D 403/10* (2013.01)

(58) Field of Classification Search
CPC ... C07D 241/20; C07D 401/12; C07D 403/12
See application file for complete search history.

(56) References Cited

U.S. PATENT DOCUMENTS

| | | |
|---|---|---|
| 7,932,246 B2 | 4/2011 | Moffat et al. |
| 7,939,666 B2 | 5/2011 | Davidson et al. |
| 7,973,181 B2 | 7/2011 | Davidson et al. |
| 8,003,695 B2 | 8/2011 | Moffat et al. |
| 8,044,211 B2 | 10/2011 | Moffat et al. |
| 8,106,091 B2 | 1/2012 | Moffat et al. |
| 8,148,531 B2 | 4/2012 | Davidson et al. |
| 8,211,900 B2 | 7/2012 | Davidson |
| 2009/0203711 A1 | 8/2009 | Moffat |
| 2009/0215800 A1 | 8/2009 | Davidson et al. |
| 2010/0004250 A1 | 1/2010 | Philips et al. |
| 2010/0010010 A1 | 1/2010 | Davidson et al. |
| 2010/0010057 A1 | 1/2010 | Moffat et al. |
| 2010/0216802 A1 | 8/2010 | Moffat et al. |
| 2010/0267774 A1 | 10/2010 | Moffat et al. |
| 2010/0317678 A1 | 12/2010 | Moffat et al. |
| 2010/0317865 A1 | 12/2010 | Davidson et al. |
| 2011/0034520 A1 | 2/2011 | Moffat et al. |
| 2011/0039920 A1 | 2/2011 | Moffat et al. |
| 2011/0046210 A1 | 2/2011 | Moffat et al. |
| 2011/0190306 A1 | 8/2011 | Moffat et al. |
| 2012/0035251 A1 | 2/2012 | Drummond et al. |

(Continued)

FOREIGN PATENT DOCUMENTS

| | | |
|---|---|---|
| EP | 0505321 A2 | 9/1992 |
| WO | 2004/076412 A2 | 9/2004 |

(Continued)

OTHER PUBLICATIONS

Hamilton, "Colony-stimulating factors in inflammation and autoimmunity", Nature Reviews, Immunology, Jul. 2008, vol. 8, pp. 533-544.
Pixley et al., "CSF-1 regulation of the wandering macrophage: complexity in action", Trends in Cell Biology, vol. 14 No. 11, Nov. 2004, pp. 628-638.
Haringman et al. "Synovial tissue macrophages: a sensitive biomaker for response to treatment in patients with rheumatoid arthritis", Ann Rheum Dis 2005; 64, pp. 834-838.
Isbel et al. "Local macrophage proliferation correlates with increased renal M-CSF expression in human glomerulonephritis", Nephrol Dial Transplant, (2001) 16: pp. 1638-1647.

(Continued)

*Primary Examiner* — Brian McDowell
(74) *Attorney, Agent, or Firm* — Norton Rose Fulbright US LLP

(57) ABSTRACT

The present invention provides a compound of formula (I) or a pharmaceutically acceptable salt, N-oxide, hydrate or solvate thereof: wherein: ring A, $R^1$, $R^2$, n, X, V, W, Z, ring B, [Linker] and R areas defined herein. The compounds are useful as inhibitors of CSF-1R kinase. The compounds can thus be used in medicine.

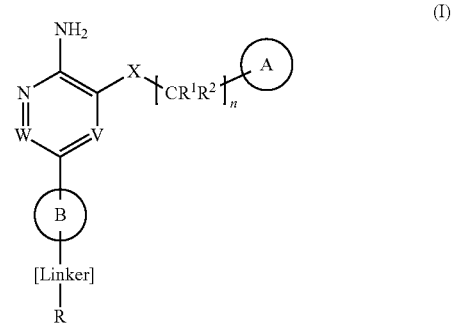

17 Claims, No Drawings

(56) References Cited

U.S. PATENT DOCUMENTS

| | | |
|---|---|---|
| 2012/0149736 A1 | 6/2012 | Donald et al. |
| 2013/0116318 A1 | 5/2013 | Davidson et al. |
| 2013/0143926 A1 | 6/2013 | Donald et al. |
| 2013/0197042 A1 | 8/2013 | Davidson et al. |
| 2013/0303576 A1 | 11/2013 | Donald et al. |
| 2014/0010762 A1 | 1/2014 | Charlton et al. |
| 2014/0088159 A1 | 3/2014 | Drummond et al. |
| 2014/0155439 A1 | 6/2014 | Donald et al. |
| 2014/0163042 A1 | 6/2014 | Davidson et al. |

FOREIGN PATENT DOCUMENTS

| | | |
|---|---|---|
| WO | 2006/021881 A2 | 3/2006 |
| WO | 2006/021886 A1 | 3/2006 |
| WO | 2008/053157 A1 | 5/2008 |
| WO | 2008/058341 A1 | 5/2008 |

OTHER PUBLICATIONS

Chen et al., "Tumor-Associated Macrophages: The Double-Edged Sword in Cancer Progression", Journal of Clinical Oncology, vol. 23, No. 5, Feb. 10, 2005, pp. 953-964.

Lewis et al., "Distinct Role of Macrophages in Different Tumor Microenvironments", Cancer Research, 2006; 66: (2), Jan. 15, 2006, pp. 605-612.

Lin et al., "Discovery of a Cytokine and Its Receptor by Functional Screening of the Extracellular Proteome", Science, vol. 320, May 9, 2008, pp. 807-811.

Meyers et al., "Structure-based drug design enables conversion of a DFG-in binding CSF-1R kinase inhibitor to a DFG-out binding mode", Bioorganic & Medicinal Chemistry Letters, 20, (2010), pp. 1543-1547.

U.S. Appl. No. 14/508,248, filed Oct. 7, 2014—Non-published application.

2-AMINOPYRAZINE DERIVATIVES AS CSF-1R KINASE INHIBITORS

CROSS REFERENCE TO RELATED APPLICATIONS

This application is a national phase application under 35 U.S.C. §371 that claims priority to International Patent Application No. PCT/GB2013/051693 filed on Jun. 26, 2013, designating the United States, which claims the benefit of priority to Great Britain Application No. 1211310.6 filed Jun. 26, 2012, all of which are incorporated herein by reference in their entireties.

The invention relates to a series of amino acid ester and cyclic amino acid ester compounds, to compositions containing them, to processes for their preparation and to their use in medicine as inhibitors of CSF-1R for the treatment of diseases and disorders mediated by CSF-1R kinase. Such diseases and disorders include cell proliferative disease such as cancer and psoriasis, polyglutamine disease such as Huntingdon's disease, neurodegenerative disease such as Alzheimers disease, autoimmune disease such as rheumatoid arthritis, diabetes, haematological disease, inflammatory disease, cardiovascular disease, atherosclerosis, and the inflammatory sequelia of infection.

BACKGROUND OF THE INVENTION

Colony-stimulating factor-1 receptor (FMS, also known as CSF-1R) is a homodimeric, class III receptor tyrosine kinase for colony-stimulating factor-1 (CSF-1 or macrophage colony-stimulating factor, M-CSF) that is encoded by the FMS proto-oncogene and has been the focus of recent reviews [*Nat. Rev. Immunol*. 2008, 8, 533.]. CSF-1 regulates the survival, proliferation, differentiation, and function of the macrophage lineage, including monocytes, tissue macrophages, dendritic cells, microglia, and osteoclasts [*Trends Cell Biol*. 2004, 14, 628-638.]. These mononuclear phagocytes act as a defence against invading pathogens by maintaining tissue homeostasis. CSF-1 exists in 3 major isoforms, namely, a secreted glycoprotein and a secreted proteoglycan, both of which circulate throughout the body, and a cell surface protein, which is involved in local regulation of target cells.

The class III receptor tyrosine kinases (RTKs), which include c-FMS, c-Kit, Flt-3, and PDGFR, are characterized by an extracellular ligand-binding domain, a single transmembrane domain (TM), a juxtamembrane domain (JM), two intracellular kinase domains (TK1 and TK2) divided by a kinase insert domain (KI), and a C-terminal domain.

Binding of CSF-1 to the extracellular domain of FMS stabilizes receptor dimerization, induces trans-autophosphorylation of the intracellular FMS domain, and activates downstream cytoplasmic signaling, which leads to differentiation and activation of macrophage lineage cells.

Small molecule inhibitors of the FMS active site block receptor autophosphorylation and subsequently block the signals that control the survival, expression, proliferation, and differentiation of macrophages. Evidence linking macrophage numbers to several diseases, including cancer and inflammatory disease, has led to extensive efforts in developing small molecule inhibitors of FMS. In studies, high macrophage levels in target tissues have been correlated with disease severity in RA [*Ann. Rheum. Dis*. 2005, 64, 834-838] and immune nephritis [*Nephrol. Dial. Transplant*. 2001, 16, 1638-1647] and poor survivability and tumor progression [*J. Clin. Oncol*. 2005, 23, 953-964. *Cancer Res*. 2006, 66, 605-612] in some cancers. Consequently, regulation of macrophage numbers may be the key role of CSF-1 function.

The colony-stimulating factors (CSFs) are a group of hematopoietic cell growth factors that include M-CSF and granulocyte colony-stimulating factor (G-CSF), both of which are relatively lineage-specific, and granulocyte/macrophage CSF (GM-CSF), which functions at earlier stages of cell lineage by regulating hematopoietic progenitors [1]. Recently, a new ligand for FMS has been identified, interleukin-34 (IL-34), which functions as a specific and independent ligand of FMS, stimulates FMS dependent phosphorylation of extracellular signal-regulated kinase-1 and -2 (ERK1/2), and promotes the formation of the colony-forming unit-macrophage (CFU-M) in human bone marrow cultures [*Science* 2008, 320, 807-811].

FMS is a critical player in the CSF-1 pathway and has emerged as a viable target for regulating macrophage levels in multiple diseases including cancer, inflammation, and autoimmunity. Therefore, the identification of novel and selective small molecule CSF-1 antagonists has become the focus of extensive competitive research efforts By regulating the development and activation of mononuclear phagocytes, CSF-1 plays a key role in the innate immune response to viral, bacterial, and fungal infections and increases the efficiency of vaccination. CSF-1 is also involved in promoting and sustaining inflammation in several diseases. Early evidence that CSF-1 depletion has a therapeutic benefit in autoimmune and inflammatory diseases was observed in the collagen-induced arthritis (CIA) mouse model. CSF-1-deficient mice were resistant to the development of arthritis despite a normal immune response to type II collagen[23]. Indeed, increased levels of CSF-1, like that found in the synovial fluid of RA patients, demonstrate a strong correlation with disease severity in conditions such as RA and immune nephritis. The proinflammatory cytokines interleukin-1β (IL-1β) and TNF-α that stimulate the production of these synovial macrophages also play a contributing role. In the CIA model, both monoclonal antibodies and small-molecule inhibitors of CSF-1 have shown efficacy in decreasing macrophage numbers in joints and slowing the overall progression of disease.

BRIEF DESCRIPTION OF THE INVENTION

The present invention makes available a new class of inhibitors of CSF-1R having pharmaceutical utility in the treatment of diseases and disorders mediated by CSF-1R kinase such as cancer, autoimmune and inflammatory diseases. The inhibitors of the invention are characterised by having an alpha amino acid motif or an alpha amino acid ester motif, which is a substrate for intracellular carboxylesterase (also referred to herein as an "esterase motif") covalently linked to the parent molecular template. The hydrophobic esterase motif allows the molecule to pass through the cell wall, and thereby allows intracellular carboxylesterase activity to hydrolyse the ester to release the parent acid. Being charged, the acid is not readily transported out of the cell, where it therefore accumulates to increase the intracellular concentration of active CSF-1R inhibitor. This leads to increases in potency and duration of action relative to the parent CSF-1R inhibitor template.

Accordingly, the present invention provides a compound which is an amino acid or amino acid ester of formula (I) or a salt, N-oxide, hydrate or solvate thereof:

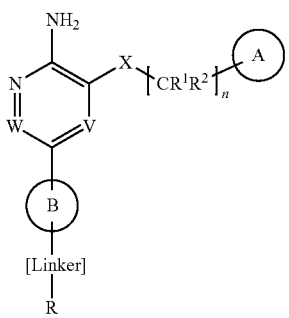

(I)

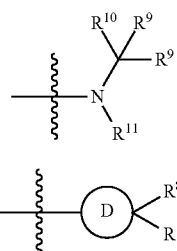

(X)

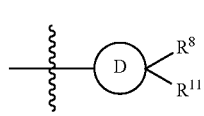

(Y)

wherein:

ring A is a $C_{6-12}$ aryl, 5- to 12-membered heterocyclyl or $C_{3-7}$ carbocyclyl ring;

$R^1$ and $R^2$ independently represent hydrogen, halogen or an unsubstituted group selected from $C_{1-4}$ alkyl, $C_{2-4}$ alkenyl, $C_{1-4}$ alkoxy, $C_{2-4}$ alkenyloxy, $C_{1-4}$ haloalkyl, $C_{2-4}$ haloalkenyl, $C_{1-4}$ haloalkoxy, $C_{2-4}$ haloalkenyloxy, hydroxyl, —$SR^3$, cyano, nitro, $C_{1-4}$ hydroxyalkyl and —$NR^3R^4$ groups, wherein $R^3$ and $R^4$ are the same or different and represent hydrogen or unsubstituted $C_{1-2}$ alkyl;

n is 0 or 1;

X is NH or O;

V and W independently represent —N= or —C(Z)=;

each Z is the same or different and represents hydrogen, fluoro, chloro, bromo, iodo, cyano, unsubstituted $C_{1-3}$ fluoroalkyl or unsubstituted $C_{1-3}$ alkyl;

ring B is a $C_{6-12}$ aryl, 5- to 12-membered heterocyclyl or $C_{3-7}$ carbocyclyl ring;

[Linker] represents a group of formula —$(CH_2)_m$—$X^1$-$L^1$-$Y^1$— wherein:

m is 0, 1, 2 or 3;

$X^1$ represents a bond, —O—, —S—, —$NR^7$—, —C(=O)—, —C(=O)O—, —OC(=O)—, —S(=O)$_2$—; —$NR^5C(=O)$—, —C(=O)$NR^5$—, —$NR^5C(=O)NR^6$—, —$NR^5S(=O)_2$—, or —S(=O)$_2NR^5$— wherein $R^5$ and $R^6$ are independently hydrogen or $C_{1-6}$ alkyl and $R^7$ represents hydrogen, unsubstituted $C_{1-4}$ alkyl or —C(=O)CH$_3$;

$L^1$ represents a divalent radical of formula -$(Alk^1)_x$-$(Q)_y$-$(Het)_w$-$(Alk^2)_z$- or -$(Alk^1)_x$-$(Het)_w$-$(Q)_y$-$(Alk^2)_z$- wherein x, y, w and z are independently 0 or 1;

Q represents a divalent $C_{6-12}$ aryl, 5- to 12-membered heterocyclyl or $C_{3-7}$ carbocyclyl ring;

Het represents —O—, —S— or —$NR^7$— wherein $R^7$ represents hydrogen, unsubstituted $C_{1-4}$ alkyl or —C(=O)CH$_3$;

$Alk^1$ and $Alk^2$ independently represent divalent $C_{3-7}$ cycloalkyl radicals, or straight or branched, $C_{1-6}$ alkylene, $C_{2-6}$ alkenylene, or $C_{2-6}$ alkynylene radicals;

$Y^1$ represents a bond, —O—, —S—, —$NR^7$—, —C(=O)—, —C(=O)O—, —OC(=O)—, —S(=O)$_2$—, —$NR^5C(=O)$—, —C(=O)$NR^5$—, —$NR^5C(=O)NR^6$—, —$NR^5S(=O)_2$—, or —S(=O)$_2NR^5$—, wherein $R^5$ and $R^6$ are independently hydrogen or $C_{1-6}$ alkyl and $R^7$ represents hydrogen, unsubstituted $C_{1-4}$ alkyl or —C(=O)CH$_3$;

R represents a group of formula (X) or (Y):

in which:

$R^8$ is a group —COOH or an ester group which is hydrolysable by one or more intracellular carboxylesterase enzymes to a —COOH group;

$R^9$ and $R^{10}$ are the same or different and each represents the α-substituent of a natural or non-natural α-amino acid, or $R^9$ and $R^{10}$, taken together with the carbon to which they are attached, form a 3- to 6-membered saturated spiro cycloalkyl or heterocyclyl ring;

$R^{11}$ represents a hydrogen atom or a $C_{1-4}$ alkyl group;

ring D is a 5- to 7-membered saturated heterocyclyl group having at least one nitrogen atom in the ring, wherein $R^8$ and $R^{11}$ are linked to a ring carbon adjacent to a ring nitrogen, and wherein the bond shown intersected by a wavy line may be from a nitrogen atom or a carbon atom in ring D;

wherein when R is (X), [Linker] is not connected to (X) via an O, N or S atom; and wherein, unless otherwise stated:

any alkyl, alkenyl and alkynyl groups and moieties in $R^5$, $R^6$, $R^8$, $R^9$, $R^{10}$, $R^{11}$, $Alk^1$ and $Alk^2$ are the same or different and are each unsubstituted or substituted with 1, 2 or 3 unsubstituted substituents which are the same or different and are selected from halogen atoms and $C_{1-4}$ alkoxy, $C_{2-4}$ alkenyloxy, $C_{1-4}$ haloalkoxy, $C_{2-4}$ haloalkenyloxy, hydroxyl, —$SR^3$, cyano, nitro and —$NR^3R^4$ groups, wherein $R^3$ and $R^4$ are the same or different and represent hydrogen or unsubstituted $C_{1-2}$ alkyl;

any aryl, heterocyclyl, cycloalkyl and carbocyclyl groups and moieties in rings A, B, Q, D, $Alk^1$ and $Alk^2$ and the ring formed by $R^9$ and $R^{10}$ are the same or different and are each unsubstituted or substituted by 1, 2, 3 or 4 unsubstituted substituents selected from halogen atoms, and cyano, nitro, $C_{1-4}$ alkyl, $C_{1-4}$ alkoxy, $C_{2-4}$ alkenyl, $C_{2-4}$ alkenyloxy, $C_{1-4}$ haloalkyl, $C_{2-4}$ haloalkenyl, $C_{1-4}$ haloalkoxy, $C_{2-4}$ haloalkenyloxy, hydroxyl, $C_{1-4}$ hydroxyalkyl, —$SR^3$ and —$NR^3R^4$ groups wherein each $R^3$ and $R^4$ is the same or different and represents hydrogen or unsubstituted $C_{1-2}$ alkyl, or from substituents of formula —$COOR^{12}$, —$COR^{12}$, —$SO_2R^{12}$, —$CONR^{12}R^{13}$, —$SO_2NR^{12}R^{13}$, —$OCONR^{12}R^{13}$, —$NR^{12}COR^{13}$, —$NR^{12}COOR^{13}$, —$NR^{12}SO_2R^{13}$, —$NR^{12}SO_2OR^{13}$ or —$NR^{12}CONR^{12}R^{13}$ wherein $R^{12}$ and $R^{13}$ are the same or different and represent hydrogen or unsubstituted $C_{1-4}$ alkyl, or $R^{12}$ and $R^{13}$ when attached to the same nitrogen atom form a non-fused 5- or 6-membered heterocyclyl group, with the proviso that the compound is not:

4-(4-{6-Amino-5-[1-(2,6-dichloro-3-fluoro-phenyl)-ethoxy]-pyridin-3-yl}-pyrazol-1-yl) -pyrrolidine-2-carboxylic acid methyl ester. It is preferable, in line with general principles of medicinal chemistry practice, that the compounds with which this invention is concerned should have molecular weights of no more than 600.

The present invention also provides a compound as defined above for use in a method of treatment of the human or animal body.

The present invention further provides a pharmaceutical composition which comprises a compound as defined above and one or more pharmaceutically acceptable carrier(s) and/or excipients.

In another aspect, the present invention provides a compound as defined above for use in the treatment of a disease or disorder mediated by CSF-1R kinase. The invention also provides use of a compound as defined above in the manufacture of a medicament for use in the treatment or prevention of a disease or disorder mediated by CSF-1R kinase.

Still further, the invention provides a method of treating or preventing a disease or disorder mediated by CSF-1R kinase in a subject, which method comprises administering to said subject an effective amount of a compound as defined above.

DETAILED DESCRIPTION OF THE INVENTION

Terminology

The alkyl, alkenyl and alkynyl groups and moieties in $R^5$, $R^6$, $R^8$, $R^9R^{10}$, $R^{11}$, $Alk^1$ and $Alk^2$ are unsubstituted or substituted with 1, 2 or 3, preferably 1 or 2, unsubstituted substituents which are the same or different and are selected from halogen atoms and $C_{1-4}$ alkoxy, $C_{2-4}$ alkenyloxy, $C_{1-4}$ haloalkoxy, $C_{2-4}$ haloalkenyloxy, hydroxyl, —$SR^3$, cyano, nitro and —$NR^3R^4$ groups, wherein $R^3$ and $R^4$ are the same or different and represent hydrogen or unsubstituted $C_{1-2}$ alkyl. More preferred substituents are halogen, $C_{1-4}$ alkoxy, hydroxyl and —$NR^3R^4$ groups, wherein $R^3$ and $R^4$ are the same or different and represent hydrogen or unsubstituted $C_{1-2}$ alkyl.

When the alkyl, alkylene, alkenylene and alkynylene moieties above are substituted by two or three substituents, it is preferred that not more than two substituents are selected from hydroxyl, cyano and nitro. More preferably, not more than one substituent is selected from hydroxyl, cyano and nitro.

As used herein, a $C_{1-6}$ alkyl group or moiety is a linear or branched alkyl group or moiety containing from 1 to 6 carbon atoms, for example a $C_{1-4}$ alkyl group or moiety containing from 1 to 4 carbon atoms. Examples of $C_{1-4}$ alkyl groups include methyl, ethyl, n-propyl, i-propyl, n-butyl, i-butyl and t-butyl. For the avoidance of doubt, where two alkyl moieties are present in a group, the alkyl moieties may be the same or different.

As used herein, a $C_{2-6}$ alkenyl group or moiety is a linear or branched alkenyl group or moiety having at least one double bond of either E or Z stereochemistry where applicable and containing from 2 to 6 carbon atoms, for example a $C_{2-4}$ alkenyl group or moiety containing from 2 to 4 carbon atoms, such as —CH=CH$_2$ or —CH$_2$—CH=CH$_2$, —CH$_2$—CH$_2$—CH=CH$_2$, —CH$_2$—CH=CH—CH$_3$, —CH=C(CH$_3$)—CH$_3$ and —CH$_2$—C(CH$_3$)=CH$_2$. For the avoidance of doubt, where two alkenyl moieties are present in a group, they may be the same or different.

As used herein, a $C_{1-6}$ alkylene group or moiety is a linear or branched alkylene group or moiety, for example a $C_{1-4}$ alkylene group or moiety. Examples include methylene, n-ethylene, n-propylene and —C(CH$_3$)$_2$— groups and moieties.

As used herein, a $C_{2-6}$ alkenylene group or moiety is a linear or branched alkenylene group or moiety, for example a $C_{2-4}$ alkenylene group or moiety. Examples include —CH=CH—, —CH=CH—CH$_2$—, —CH$_2$—CH=CH— and —CH=CH—CH=CH—.

As used herein, a $C_{2-6}$ alkynylene group or moiety is a linear or branched alkynylene group or moiety, for example a $C_{2-4}$ alkynylene group or moiety. Examples include —C≡C—, —C≡C—CH$_2$— and —CH$_2$—C≡C—.

As used herein, a halogen atom is chlorine, fluorine, bromine or iodine.

As used herein, a $C_{1-4}$ alkoxy group or $C_{2-4}$ alkenyloxy group is typically a said $C_{1-4}$ alkyl group or a said $C_{2-4}$ alkenyl group respectively which is attached to an oxygen atom.

A haloalkyl, haloalkenyl, haloalkoxy or haloalkenyloxy group is typically a said alkyl, alkenyl, alkoxy or alkenyloxy group respectively which is substituted by one or more said halogen atoms. Typically, it is substituted by 1, 2 or 3 said halogen atoms. Preferred haloalkyl and haloalkoxy groups include perhaloalkyl and perhaloalkoxy groups such as —CX$_3$ and —OCX$_3$ wherein X is a said halogen atom, for example chlorine or fluorine. A fluoroalkyl group is typically a said alkyl group which is substituted by one or more fluorine atoms. Typically, it is substituted by 1, 2 or 3 said fluorine atoms.

As used herein, a $C_{1-4}$ hydroxyalkyl group is a $C_{1-4}$ alkyl group substituted by one or more hydroxy groups. Typically, it is substituted by one, two or three hydroxy groups. Preferably, it is substituted by a single hydroxy group.

As used herein, a $C_{6-12}$ aryl group or moiety is a monocyclic, 6- to 12-membered aromatic hydrocarbon ring having from 6 to 12 carbon atoms, for example phenyl or naphtyl. Phenyl is preferred.

As used herein the unqualified term "heteroaryl" refers to a mono-, bi- or tri-cyclic aromatic radical containing one or more, for example 1, 3 or 4, in particular 1 or 2, heteroatoms selected from S, N and O, and includes radicals having two such monocyclic rings, or one such monocyclic ring and one monocyclic aryl ring, which are directly linked by a covalent bond. Illustrative of such radicals are thienyl, benzthienyl, furyl, benzfuryl, pyrrolyl, imidazolyl, benzimidazolyl, thiazolyl, benzthiazolyl, isothiazolyl, benzisothiazolyl, pyrazolyl, oxazolyl, benzoxazolyl, isoxazolyl, benzisoxazolyl, isothiazolyl, triazolyl, benztriazolyl, thiadiazolyl, oxadiazolyl, pyridinyl, pyridazinyl, pyrimidinyl, pyrazinyl, triazinyl, indolyl and indazolyl, in particular pyrazole.

As used herein the unqualified term "heterocyclyl" or "heterocyclic" includes "heteroaryl" as defined above, and in its non-aromatic meaning relates to a saturated or unsaturated mono-, bi- or tri-cyclic non-aromatic radical containing one or more, for example 1, 2, 3 or 4 in particular 1 or 2, heteroatoms selected from S, N and O, and to groups consisting of a monocyclic non-aromatic radical containing one or more such heteroatoms which is covalently linked to another such radical or to a monocyclic carbocyclic radical. Illustrative of such radicals are pyrrolyl, furanyl, thienyl, piperidinyl, imidazolyl, oxazolyl, isoxazolyl, thiazolyl, thiadiazolyl, pyrazolyl, pyridinyl, pyrrolidinyl, pyridazinyl, pyrimidinyl, pyrazinyl, morpholinyl, piperazinyl, indolyl, benzfuranyl, pyranyl, isoxazolyl, benzimidazolyl, methylenedioxyphenyl, ethylenedioxyphenyl, maleimido and succinimido groups, in particular piperidinyl, piperazinyl and pyrazolyl.

As used herein, a $C_{3-7}$ carbocyclic group or moiety is a non-aromatic saturated or unsaturated hydrocarbon ring having from 3 to 7 carbon atoms. Preferably it is a saturated or mono-unsaturated hydrocarbon ring (i.e. a cycloalkyl moiety or a cycloalkenyl moiety) having from 3 to 7 carbon atoms, more preferably having from 3 to 6 carbon atoms. Examples include cyclopropyl, cyclobutyl, cyclopentyl and cyclohexyl and their mono-unsaturated variants. Preferred examples of $C_{3-7}$ carbocyclic group or moieties are cyclopentyl and cyclohexyl. A $C_{3-7}$ carbocyclyl group or moiety also includes $C_{3-7}$ carbocyclyl groups or moieties described above but wherein one or more ring carbon atoms are replaced by a group —C(O)—. More preferably, 0, 1 or 2 ring carbon atoms (most preferably 0 or 2) are replaced by —C(O)—. A preferred such group is benzoquinone.

As used herein the term "cycloalkyl" refers to a monocyclic saturated carbocyclic radical having from 3-8 carbon atoms and includes, for example, cyclopropyl, cyclobutyl, cyclopentyl, cyclohexyl, cycloheptyl and cyclooctyl.

When the aryl, heterocyclyl, cycloalkyl and carbocyclyl groups and moieties in rings A, B, Q and D and the rings formed by $Alk^1$ and $Alk^2$ and by $R^9$ and $R^{10}$ are substituted by two, three or four substituents, it is preferred that not more than two substituents are selected from hydroxyl, cyano and nitro. More preferably, not more than one substituent is selected from hydroxyl, cyano and nitro. Furthermore, when the aryl, heteroaryl, heterocyclyl and carbocyclyl moieties are substituted by two or three substituents, it is preferred that not more than one substituent is selected from —COOR$^{12}$, —COR$^{12}$, —SO$_2$R$^{12}$, —CONR$^{12}$R$^{13}$, —SO$_2$NR$^{12}$R$^{13}$, —OCONR$^{12}$R$^{13}$, —NR$^{12}$COR$^{13}$, —NR$^{12}$COOR$^{13}$, —NR$^{12}$SO$_2$R$^{13}$, —NR$^{12}$SO$_2$OR$^{13}$ or —NR$^{12}$CONR$^{12}$R$^{13}$.

As used herein the term "salt" includes base addition, acid addition and quaternary salts. Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris(hydroxymethyl)amino-methane, L-arginine, L-lysine, N-ethyl piperidine, dibenzylamine and the like. Those compounds which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesulfonic, glutamic, lactic, and mandelic acids and the like.

It is expected that compounds of the invention may be recovered in hydrate or solvate form. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Compounds of the invention which contain one or more actual or potential chiral centres, because of the presence of asymmetric carbon atoms, can exist as a number of diastereoisomers with R or S stereochemistry at each chiral centre. The invention includes all such diastereoisomers and mixtures thereof.

Preferably ring A represents phenyl or a 5- to 6-membered heterocyclyl group, said ring A group being unsubstituted or substituted by 1, 2 or 3 substituents which are the same or different and are selected from halogen atoms and unsubstituted $C_{1-4}$ alkyl, $C_{1-4}$ alkoxy, hydroxyl, $C_{1-4}$ haloalkyl, $C_{1-4}$ haloalkoxy, $C_{1-4}$ hydroxyalkyl, cyano, nitro, —SR$^3$ and —NR$^3$R$^4$ groups, wherein R$^3$ and R$^4$ are the same or different and represent hydrogen or unsubstituted $C_{1-2}$ alkyl. More preferably, ring A represents a phenyl group, said ring A group being unsubstituted or substituted by 1, 2 or 3 substituents which are the same or different and are selected from halogen atoms and unsubstituted $C_{1-4}$ alkyl, $C_{1-4}$ alkoxy, hydroxyl and —NR$^3$R$^4$ groups, wherein R$^3$ and R$^4$ are the same or different and represent hydrogen or unsubstituted $C_{1-2}$ alkyl. For example, ring A may represent a phenyl group, said ring A group being unsubstituted or substituted by 1, 2 or 3 substituents which are the same or different and are selected from fluorine and chlorine.

Preferably R$^1$ and R$^2$ independently represent hydrogen, halogen or unsubstituted $C_{1-4}$ alkyl; more preferably hydrogen.

Preferably n is 1.

Preferably X is NH.

The ring containing V and W may contain a total of 1, 2 or 3 nitrogen atoms. In one embodiment, V is —N= and W is —C(Z)=. In another embodiment, V is —C(Z)= and W is —N=. Preferably, V is —N= and W is —C(Z)=; more preferably —CH=.

Preferably Z represents hydrogen, fluoro, chloro, or unsubstituted $C_{1-3}$ alkyl; more preferably hydrogen.

Preferably ring B represents phenyl or a 5- to 6-membered heterocyclyl group, preferably phenyl or a 5- to 6-membered heterocyclyl group containing 1, 2 or 3 nitrogen atoms, for example pyridinyl, pyridazinyl, pyrimidinyl, pyrazinyl or pyrazolyl, in particular pyridinyl, pyridazinyl, pyrimidinyl or pyrazinyl, said ring B group being unsubstituted or substituted by 1, 2 or 3 substituents which are the same or different and are selected from halogen atoms and unsubstituted $C_{1-4}$ alkyl, $C_{1-4}$ alkoxy, hydroxyl, $C_{1-4}$ haloalkyl, $C_{1-4}$ haloalkoxy, $C_{1-4}$ hydroxyalkyl, cyano, nitro, —SR$^3$ and —NR$^3$R$^4$ groups, wherein R$^3$ and R$^4$ are the same or different and represent hydrogen or unsubstituted $C_{1-2}$ alkyl.

More preferably, ring B represents a 1,4-phenylene group, 1,3-phenylene group, 1,3-pyrazolyl group or pyridinyl group, in particular a 1,4-phenylene group, 1,3-phenylene group or 1,3-pyrazolyl group, said ring B group being unsubstituted or substituted by 1, 2 or 3 substituents which are the same or different and are selected from halogen atoms and unsubstituted $C_{1-4}$ alkyl, $C_{1-4}$ alkoxy, hydroxyl and —NR$^3$R$^4$ groups, wherein R$^3$ and R$^4$ are the same or different and represent hydrogen or unsubstituted $C_{1-2}$ alkyl. For example, ring B may represent an unsubstituted 1,3-pyrazolyl group, or a 1,4-phenylene or 1,3-phenylene group which is unsubstituted or substituted by 1, 2 or 3 substituents which are the same or different and are selected from fluorine, chlorine, methyl and ethyl.

Typically, ring B represents a 1,4-phenylene group, 1,3-phenylene group or pyridinyl group, in particular a 1,4-phenylene group or 1,3-phenylene group, said ring B group being unsubstituted or substituted by 1, 2 or 3 substituents which are the same or different and are selected from halogen atoms and unsubstituted $C_{1-4}$ alkyl, $C_{1-4}$ alkoxy, hydroxyl and —NR$^3$R$^4$ groups, wherein R$^3$ and R$^4$ are the same or different and represent hydrogen or unsubstituted $C_{1-2}$ alkyl. For example, ring B may represent a 1,4-phenylene or 1,3-phenylene group which is unsubstituted or substituted by 1, 2 or 3 substituents which are the same or different and are selected from fluorine, chlorine, methyl and ethyl.

When B is as defined hereinabove, X is preferably NH.

[Linker] represents a group of formula —$(CH_2)_m$—$X^1$-$L^1$-$Y^1$—.

Preferably, m is 0, 1 or 2.

In some embodiments, $X^1$ may preferably represent a bond, —O—, —S—, —$NR^7$—, —C(=O)— or —C(=O)$NR^5$—, wherein $R^5$ is hydrogen or $C_{1-4}$ alkyl and $R^7$ represents hydrogen, unsubstituted $C_{1-4}$ alkyl or —C(=O)$CH_3$. More preferably, $X^1$ represents a bond or —C(=O)—.

$L^1$ represents a divalent radical of formula -$(Alk^1)_x$-$(Q)_y$-$(Het)_w$-$(Alk^2)_z$- or -$(Alk^1)_x$-$(Het)_w$-$(Q)_y$-$(Alk^2)_z$-.

Preferably Q represents phenyl or a 5- to 6-membered heterocyclyl group which is unsubstituted or substituted with 1, 2 or 3 substituents which are the same or different and are selected from halogen atoms and unsubstituted $C_{1-4}$ alkyl, $C_{1-4}$ alkoxy, hydroxyl and —$NR^3R^4$ groups, wherein $R^3$ and $R^4$ are the same or different and represent hydrogen or unsubstituted $C_{1-2}$ alkyl. Preferably Q is unsubstituted phenyl, preferably unsubstituted 1,4-phenylene.

Preferably $Alk^1$ and $Alk^2$ independently represent a $C_{1-3}$ alkylene, $C_{2-3}$ alkenylene or $C_{2-3}$ alkynylene group which is unsubstituted or unsubstituted with 1, 2 or 3 unsubstituted substituents which are the same or different and are selected from halogen atoms and $C_{1-2}$ alkoxy, hydroxyl and —$NR^3R^4$ groups, wherein $R^3$ and $R^4$ are the same or different and represent hydrogen or unsubstituted $C_{1-2}$ alkyl. More preferably, $Alk^1$ and $Alk^2$ independently represent unsubstituted $C_{1-3}$ alkylene.

Preferably Het is —O— or —$NR^7$—, preferably wherein $R^7$ is hydrogen, unsubstituted methyl, unsubstituted ethyl, unsubstituted isobutyl or —C(=O)$CH_3$. More preferably, Het is —O—.

In one embodiment, y and w are each 1 and at least one of x and z is 1, for example $L^1$ is -$Alk^1$-Het-Q- or -Q-Het-$Alk^2$-. Preferably, Q represents phenyl or a 5- to 6-membered heterocyclyl group as described above, preferably unsubstituted phenyl, preferably unsubstituted 1,4-phenylene; $Alk^1$ and $Alk^2$ independently represent a $C_{1-3}$ alkylene, $C_{2-3}$ alkenylene or $C_{2-3}$ alkynylene group as described above, preferably unsubstituted $C_{1-3}$ alkylene; and Het represents —O— or —$NR^7$— as described above, preferably —O—.

In one preferred embodiment, at least one of x and z is 1, y and w are each 0 and $Alk^1$ and $Alk^2$ independently represent unsubstituted $C_{1-3}$ alkylene. In another preferred embodiment, x, y and z are each 0.

In some embodiments, $Y^1$ may preferably represent a bond, —O—, —S—, —C(=O)— or —C(=O)$NR^5$—, wherein $R^5$ and is hydrogen or $C_{1-4}$ alkyl and $R^7$ represents hydrogen, unsubstituted $C_{1-4}$ alkyl or —C(=O)$CH_3$. More preferably, $Y^1$ represents a bond or —$NR^7$—, wherein $R^7$ represents hydrogen, unsubstituted $C_{1-4}$ alkyl or —C(=O)$CH_3$, preferably, hydrogen, unsubstituted methyl, unsubstituted ethyl, unsubstituted isobutyl or —C(=O)$CH_3$.

In one embodiment, [Linker] represents —$(CH_2)_m$—$X^1$-$(Alk^1)_x$-$Y^1$, wherein m, x, $X^1$, $Y^1$ and $Alk^1$ are as defined herein. Preferably, $Alk^1$ is an unsubstituted alkylene group, $X^1$ and $Y^1$ independently represent a bond, —O—, —S—, —C(=O)— or —C(=O)$NR^5$—, wherein $R^5$ is hydrogen or $C_{1-4}$ alkyl and $R^7$ represents hydrogen, unsubstituted $C_{1-4}$ alkyl or —C(=O)$CH_3$. More preferably, $X^1$ represents a bond or —C(=O)— and $Y^1$ represents a bond or —$NR^7$—, wherein $R^7$ represents hydrogen, unsubstituted $C_{1-4}$ alkyl or —C(=O)$CH_3$, preferably, hydrogen, unsubstituted methyl, unsubstituted ethyl, unsubstituted isobutyl or —C(=O)$CH_3$. Most preferred [Linker] groups are —$(CH_2)_v$—, —C(=O)$NR^7$—, —$CH_2NR^7$—, —$CH_2$C(=O)$NR^7$— and —C(=O)—, wherein v is 1 or 2 and $R^7$ represents hydrogen, unsubstituted methyl, unsubstituted ethyl, unsubstituted isobutyl or —C(=O)$CH_3$.

In one embodiment, R represents a group of formula (X). When R is (X), [Linker] is not connected to (X) via an O, S or N atom of the [Linker] moiety. Thus when R is (X) and x, y and z are each 0, $X^1$ and $Y^1$ are preferably independently chosen from a bond, —C(=O)—, —OC(=O)—, and —$NR^5$C(=O)—, wherein $R^5$ is hydrogen or $C_{1-6}$ alkyl; or when R is (X) and at least one of x, y and z is 1, $Y^1$ is preferably chosen from a bond, —C(=O)—, —OC(=O)—, and —$NR^5$C(=O)—, and $X^1$ is preferably chosen from a bond, —O—, —S—, —C(=O)— or —C(=O)$NR^5$—, wherein $R^5$ is hydrogen or $C_{1-4}$ alkyl and $R^7$ represents hydrogen, unsubstituted $C_{1-4}$ alkyl or —C(=O)$CH_3$. Preferably, when R is (X), [Linker] is —$(CH_2)_m$—$X^1$-$(Alk^1)$- or —$(CH_2)_v$—, wherein v is 1 or 2, m is 0, 1, 2 or 3; $Alk^1$ is an unsubstituted $C_{1-3}$ alkylene group and $X^1$ is a bond, —O—, —S—, —C(=O)— or —C(=O)$NR^5$—, wherein $R^5$ is hydrogen or $C_{1-4}$ alkyl and $R^7$ represents hydrogen, unsubstituted $C_{1-4}$ alkyl or —C(=O)$CH_3$. Most preferred [Linker] groups when R is (X) are groups —$(CH_2)_v$— wherein v is 1 or 2.

In another embodiment, R represents a group of formula (Y1):

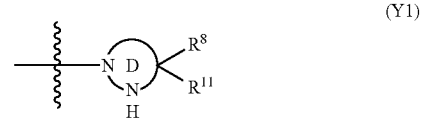

wherein ring D is a 5- to 7-membered saturated heterocyclyl group having at least two nitrogen atoms in the ring, wherein $R^8$ and $R^{11}$ are linked to a ring carbon adjacent to a ring nitrogen, and wherein the bond shown intersected by a wavy line is from a nitrogen atom in ring D.

When R is (Y1), [Linker] is preferably not connected to (Y1) via an O, S or N atom of the [Linker] moiety. Thus when R is (Y1) and x, y and z are each 0, $X^1$ and $Y^1$ are preferably chosen from a bond, —C(=O)—, —OC(=O)—, and —$NR^5$C(=O)—, wherein $R^5$ is hydrogen or $C_{1-6}$ alkyl, or when R is (Y1) and at least one of x, y and z is 1, $Y^1$ is preferably chosen from a bond, —C(=O)—, —OC(=O)—, and —$NR^5$C(=O)— and $X^1$ is preferably chosen from a bond, —O—, —S—, —$NR^7$—, —C(=O)— or —C(=O)$NR^5$—, wherein $R^5$ is hydrogen or $C_{1-4}$ alkyl and $R^7$ represents hydrogen, unsubstituted $C_{1-4}$ alkyl or —C(=O)$CH_3$. Preferably, when R is (Y1), [Linker] is —$(CH_2)_m$—$X^1$-$(Alk^1)_x$- or —$(CH_2)_v$—, wherein v is 1 or 2, m is 0, 1, 2 or 3; x is 0 or 1; $Alk^1$ is an unsubstituted alkylene group; and $X^1$ is a bond, —O—, —S—, —$NR^7$—, —C(=O)— or —C(=O)$NR^5$—, wherein $R^5$ is hydrogen or $C_{1-4}$ alkyl and $R^7$ represents hydrogen, unsubstituted $C_{1-4}$ alkyl or —C(=O)$CH_3$, wherein when x is 0, $X^1$ is a bond or C(=O). Most preferred [Linker] groups are —$(CH_2)_v$— and —C(=O)—, wherein v is 1 or 2.

Preferably the group of formula (Y1) is a group of formula (Y1'):

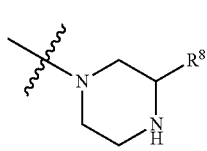

In another embodiment, R represents a group of formula (Y2):

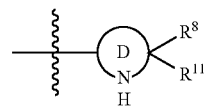

wherein ring D is a 5- to 7-membered saturated heterocyclyl group having at least one nitrogen atom in the ring, wherein $R^8$ and $R^{11}$ are linked to a ring carbon adjacent to a ring nitrogen, and wherein the bond shown intersected by a wavy line is from a carbon atom in ring D.

Typically, when R is Y2, ring D is a 5- to 7-membered saturated heterocyclyl group having at least one nitrogen atom in the ring, wherein $R^8$ and $R^{11}$ are linked to a ring carbon adjacent to a ring nitrogen, and wherein the bond shown intersected by a wavy line is from a carbon atom in ring D, with the proviso that D is not a pyrrolidinyl group. D may, for example, be a pyrrolyl, piperidinyl, imidazolyl, oxazolyl, isoxazolyl, thiazolyl, thiadiazolyl, pyrazolyl, pyridinyl, pyridazinyl, pyrimidinyl, pyrazinyl, morpholinyl, piperazinyl group, for instance a piperidinyl or piperazinyl group, for example a piperidinyl group.

When R is (Y2), $Y^1$ in [Linker] may preferably represent a bond, —O—, —S—, —$NR^7$—, —C(=O)— or —C(=O)$NR^5$—, wherein $R^5$ is hydrogen or $C_{1-4}$ alkyl and $R^7$ represents hydrogen, unsubstituted $C_{1-4}$ alkyl or —C(=O)$CH_3$. More preferably, $Y^1$ represents a bond or —$NR^7$—, wherein $R^7$ represents hydrogen, unsubstituted $C_{1-4}$ alkyl or —C(=O)$CH_3$, preferably, hydrogen, unsubstituted methyl, unsubstituted ethyl, unsubstituted isobutyl or —C(=O)$CH_3$. When R is (Y2), [Linker] is preferably connected to (Y2) via an N atom of the [Linker] moiety. Thus when R is (Y2), $Y^1$ is preferably —$NR^7$—, wherein $R^7$ represents hydrogen, unsubstituted $C_{1-4}$ alkyl or —C(=O)$CH_3$, preferably, hydrogen, unsubstituted methyl, unsubstituted ethyl, unsubstituted isobutyl or —C(=O)$CH_3$.

Thus, when R is (Y2), [Linker] typically represents —$(CH_2)_m$—$X^1$-$(Alk^1)_x$-$Y^1$—, wherein m is 0, 1, 2 or 3; x is 0 or 1; $X^1$ is a bond, —O—, —S—, —$NR^7$—, —C(=O)— or —C(=O)$NR^5$—, preferably a bond or —C(=O)—, wherein $R^5$ is hydrogen or $C_{1-4}$ alkyl and $R^7$ represents hydrogen, unsubstituted $C_{1-4}$ alkyl or —C(=O)$CH_3$; $Alk^1$ is an unsubstituted $C_{1-3}$ alkylene group; and $Y^1$ is a bond or —$NR^7$—, preferably —$NR^7$—, wherein $R^7$ represents hydrogen, unsubstituted $C_{1-4}$ alkyl or —C(=O)$CH_3$. Most preferred [Linker] groups are —C(=O)$NR^7$—, —$CH_2NR^7$—, —$CH_2CH_2NR^7$—, $NR^7$— and —$CH_2C$(=O)$NR^7$—, wherein $R^7$ represents hydrogen, unsubstituted methyl, unsubstituted ethyl, unsubstituted isobutyl or —C(=O)$CH_3$.

Preferably the group of formula (Y2) is a group of formula (Y2'):

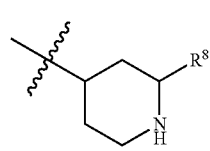

Preferably in the above formulae
$R^8$ is a group —COOH or an ester group of formula —(C=O)$OR^{14}$ wherein $R^{14}$ is $R^{15}R^{16}R^{17}C$— wherein
(i) $R^{15}$ is hydrogen, fluorine or optionally substituted $C_{1-3}$alkyl-$(Z^1)_a$—[$(C_1$-$C_3)$alkyl]$_b$- or $C_{2-3}$alkenyl-$(Z^1)_a$-[$C_{1-3}$ alkyl]$_b$- wherein a and b are independently 0 or 1 and $Z^1$ is —O—, —S—, or —$NR^{18}$— wherein $R^{18}$ is hydrogen or $C_{1-3}$ alkyl; and $R^{16}$ and $R^{17}$ are independently hydrogen or $C_{1-3}$ alkyl-;
(ii) $R^{15}$ is hydrogen or optionally substituted $R^{19}R^{20}N$—$C_{1-3}$alkyl- wherein $R^{19}$ is hydrogen or $C_{1-3}$alkyl and $R^{20}$ is hydrogen or $C_{1-3}$alkyl; or $R^{19}$ and $R^{20}$ together with the nitrogen to which they are attached form an optionally substituted monocyclic heterocyclic ring of 5- or 6- ring atoms or bicyclic heterocyclic ring system of 8 to 10 ring atoms, and $R^{16}$ and $R^{17}$ are independently hydrogen or $C_{1-3}$alkyl-; or
(iii) $R^{15}$ and $R^{16}$ taken together with the carbon to which they are attached form an optionally substituted monocyclic carbocyclic ring of from 3 to 7 ring atoms or bicyclic carbocyclic ring system of 8 to 10 ring atoms, and $R^{17}$ is hydrogen; or
(iv) $R^{15}$ and $R^{16}$ taken together with the carbon to which they are attached form an optionally substituted monocyclic heterocyclic ring of from 3 to 7 ring atoms wherein at least one ring atom is selected from —O—, —S—, or —$NR^{18}$— wherein $R^{18}$ is hydrogen or $C_{1-3}$alkyl, or a bicyclic heterocyclic ring system of 8 to 10 ring atoms wherein at least one ring atom is selected from —O—, —S—, or —$NR^{18}$— wherein $R^{18}$ is hydrogen or $C_{1-3}$alkyl, and $R^{17}$ is hydrogen.

Within these classes, $R^{14}$ may be, for example methyl, ethyl, n- or iso-propyl, n-, sec- or tert-butyl, dimethyl propyl, pentanyl, cyclopentyl, methyl-substituted cyclopentyl, cyclopentylmethyl, cyclohexyl, N-methylpiperidin-4-yl, N-methylpyrrolidin-3-yl, tetrahydrofuran-3-yl, methoxyethyl, indanyl, norbornyl, dimethylaminoethyl, or morpholinoethyl.

In one embodiment, either $R^{15}$ is hydrogen or $C_{1-3}$alkyl-$(Z^1)_a$—[$(C_1$-$C_3)$alkyl]$_b$- wherein a and b are independently 0 or 1 and $Z^1$ is —O—, —S—, or —NH— and $R^{16}$ and $R^{17}$ are independently hydrogen or $C_{1-3}$ alkyl-; or $R^{15}$ and $R^{16}$ taken together with the carbon to which they are attached form a 3- to 7-membered cycloalkyl ring and $R^{17}$ is hydrogen. Cyclopentyl and t-butyl are particularly preferred at $R^{14}$.

Preferably $R^9$ and $R^{10}$ are the same or different and each represents the side chain of a natural amino acid or:
(i) a hydrogen atom;
(ii) a $C_{1-6}$ alkyl group;
(iii) $R^9$ and $R^{10}$, taken together with the carbon to which they are attached, form a 3- to 6-membered saturated spiro cycloalkyl ring;

(iv) a group -L²-B¹, in which L² represents a bond or a C$_{1-6}$ alkylene group and B¹ represents a C$_{6-10}$ aryl or 5- to 10-membered heteroaryl group;

or (v) a group selected from indol-3-ylmethyl, —CH$_2$COOH, —CH$_2$CH$_2$COOH, —CH$_2$CONH$_2$, —CH$_2$CH$_2$CONH$_2$, —CH$_2$CH$_2$CH$_2$NHC(NH)NH$_2$, cyclohexyl, cyclohexylmethyl and 1-benzylthio-1-methylethyl;

said C$_{1-6}$ alkyl group in (ii) is unsubstituted or substituted with 1 or 2 substituents which are the same or different and represent halogen, C$_{1-4}$ alkoxy, C$_{1-2}$ haloalkyl, hydroxyl, —COOR³, —COONR³R⁴, —SR³ and —NR³R⁴ wherein R³ and R⁴ are the same or different and represent hydrogen or unsubstituted C$_{1-2}$ alkyl;

said C$_{1-6}$ alkylene group in (iv) is unsubstituted or substituted with 1, 2 or 3 unsubstituted substituents which are the same or different and are selected from halogen atoms and C$_{1-4}$ alkoxy, hydroxyl, C$_{1-2}$ haloalkyl and —NR³R⁴ groups where R³ and R⁴ are the same or different and represent hydrogen or unsubstituted C$_{1-2}$ alkyl; and said C$_{6-10}$ aryl or 5- to 10-membered heteroaryl group in (iv) is unsubstituted or substituted by 1, 2 or 3 substituents which are the same or different and are selected from halogen atoms and unsubstituted C$_{1-4}$ alkyl, C$_{1-4}$ alkoxy, hydroxyl, C$_{1-4}$ haloalkyl, C$_{1-4}$ haloalkoxy, C$_{1-4}$ hydroxyalkyl, cyano, nitro, —SR³ and —NR³R⁴ groups where R³ and R⁴ are the same or different and represent hydrogen or unsubstituted C$_{1-2}$ alkyl.

More preferably, R⁹ and R¹⁰ independently represent a hydrogen atom; a C$_{1-6}$ alkyl group which is unsubstituted or substituted with 1 or 2 substituents which are the same or different and represent halogen, C$_{1-4}$ alkoxy, hydroxyl, —COOR³, —COONR³R⁴, —SR³ and —NR³R⁴ wherein R³ and R⁴ are the same or different and represent hydrogen or unsubstituted C$_{1-2}$ alkyl; R⁹ and R¹⁰, taken together with the carbon to which they are attached, form a 3- to 6-membered saturated spiro cycloalkyl ring; or a group of formula -L²-B¹ wherein L² is a bond or an unsubstituted C$_{1-4}$ alkylene group and B¹ represents a phenyl or a 5- to 10-membered heteroaryl group which is unsubstituted or substituted with one, two or three unsubstituted substituents which are the same or different and represent halogen atoms, C$_{1-4}$ alkyl, C$_{1-2}$ alkoxy, C$_{1-2}$ alkylthio and hydroxyl. Preferably, (i) R⁹ and R¹⁰ are side chains of natural amino acids, (ii) one of R⁹ and R¹⁰ is hydrogen or unsubstituted C$_{1-4}$ alkyl and the other is an unsubstituted C$_{1-6}$ alkyl group or a C$_{1-6}$ alkyl group substituted with a C$_{1-4}$ alkoxy group, or (iii) R⁹ and R¹⁰, taken together with the carbon to which they are attached, form a saturated spiro cyclobutyl ring. (ii) or (iii) is preferred.

Preferably R¹¹ represents a hydrogen atom or an unsubstituted C$_{1-2}$ alkyl group, preferably a hydrogen atom.

In a preferred embodiment of the invention there is provided a compound of formula (I) or a pharmaceutically acceptable salt, N-oxide, hydrate or solvate thereof, in which:

ring A represents phenyl or a 5- to 6-membered heterocyclyl group, said ring A group being unsubstituted or substituted by 1, 2 or 3 substituents which are the same or different and are selected from halogen atoms and unsubstituted C$_{1-4}$ alkyl, C$_{1-4}$ alkoxy, hydroxyl, C$_{1-4}$ haloalkyl, C$_{1-4}$ haloalkoxy, C$_{1-4}$ hydroxyalkyl, cyano, nitro, —SR³ and —NR³R⁴ groups, wherein R³ and R⁴ are the same or different and represent hydrogen or unsubstituted C$_{1-2}$ alkyl;

R¹ and R² each represent hydrogen;

n is 1;

X is NH;

V is —N=;

W is —C(Z)=, wherein Z represents hydrogen, fluoro, chloro, or unsubstituted C$_{1-3}$ alkyl, preferably hydrogen; and ring B represents phenyl or 5- to 6-membered heterocyclyl group, said ring B group being unsubstituted or substituted by 1, 2 or 3 substituents which are the same or different and are selected from halogen atoms and unsubstituted C$_{1-4}$ alkyl, C$_{1-4}$ alkoxy, hydroxyl, C$_{1-4}$ haloalkyl, C$_{1-4}$ haloalkoxy, C$_{1-4}$ hydroxyalkyl, cyano, nitro, —SR³ and —NR³R⁴ groups, wherein R³ and R⁴ are the same or different and represent hydrogen or unsubstituted C$_{1-2}$ alkyl.

In this embodiment of the invention, the group [Linker]-R preferably corresponds to one of (a) to (c) set out below:

(a) R represents a group of formula (X);

R⁸ is as set out below;

R⁹ and R¹⁰ are side chains of natural amino acids, one of R⁹ and R¹⁰ is hydrogen or unsubstituted C$_{1-4}$ alkyl and the other is an unsubstituted C$_{1-6}$ alkyl group or a C$_{1-6}$ alkyl group substituted with a C$_{1-4}$ alkoxy group, or R⁹ and R¹⁰, taken together with the carbon to which they are attached, form a saturated spiro cyclobutyl ring;

R¹¹ represents a hydrogen atom or an unsubstituted C$_{1-2}$ alkyl group;

[Linker] represents —(CH$_2$)$_m$—X¹-(Alk¹)- or —(CH$_2$)$_v$—, wherein v is 1 or 2, m is 0, 1, 2 or 3; Alk¹ is an unsubstituted C$_{1-3}$ alkylene group and X¹ is a bond, —O—, —S—, —NR⁷—, —C(=O)— or —C(=O)NR⁵—, wherein R⁵ is hydrogen or C$_{1-4}$ alkyl and R⁷ represents hydrogen, unsubstituted C$_{1-4}$ alkyl or —C(=O)CH$_3$.

(b) R represents a group of formula (Y1);

R⁸ is as set out below;

R¹¹ represents a hydrogen atom or an unsubstituted C$_{1-2}$ alkyl group;

[Linker] is —(CH$_2$)$_m$—X¹-(Alk¹)$_x$- or —(CH$_2$)$_v$—, wherein v is 1 or 2, m is 0, 1, 2 or 3;

x is 0 or 1; Alk¹ is an unsubstituted C$_{1-3}$ alkylene group; and X¹ is a bond, —O—, —S—, —NR⁷—, —C(=O)— or —C(=O)NR⁵—, wherein R⁵ is hydrogen or C$_{1-4}$ alkyl and R⁷ represents hydrogen, unsubstituted C$_{1-4}$ alkyl or —C(=O)CH$_3$, wherein when x is 0, X¹ is a bond or C(=O).

(c) R represents a group of formula (Y2);

R⁸ is as set out below;

R¹¹ represents a hydrogen atom or an unsubstituted C$_{1-2}$ alkyl group;

[Linker] represents —(CH$_2$)$_m$—X¹-(Alk¹)$_x$-Y¹, wherein m is 0, 1, 2 or 3; x is 0 or 1;

X¹ is a bond or —C(=O); Alk¹ is an unsubstituted C$_{1-3}$ alkylene group; and Y¹ is a bond or —NR⁷—, preferably —NR⁷—, wherein R⁷ represents hydrogen, unsubstituted C$_{1-4}$ alkyl or —C(=O)CH$_3$.

Typically, in this embodiment, when R is Y2, ring D is a 5- to 7-membered saturated heterocyclyl group having at least one nitrogen atom in the ring, wherein R⁸ and R¹¹ are linked to a ring carbon adjacent to a ring nitrogen, and wherein the bond shown intersected by a wavy line is from a carbon atom in ring D, with the proviso that D is not a pyrrolidinyl group. D may, for example, be a pyrrolyl, piperidinyl, imidazolyl, oxazolyl, isoxazolyl, thiazolyl, thiadiazolyl, pyrazolyl, pyridinyl, pyridazinyl, pyrimidinyl, pyrazinyl, morpholinyl, piperazinyl group, for instance a piperidinyl or piperazinyl group, for example a piperidinyl group.

In this embodiment, preferably, ring B represents a 1,4-phenylene group, 1,3-phenylene group or pyridinyl group, in particular a 1,4-phenylene group or 1,3-phenylene group, said ring B group being unsubstituted or substituted by 1, 2 or 3 substituents which are the same or different and are selected from halogen atoms and unsubstituted $C_{1-4}$ alkyl, $C_{1-4}$ alkoxy, hydroxyl and —$NR^3R^4$ groups, wherein $R^3$ and $R^4$ are the same or different and represent hydrogen or unsubstituted $C_{1-2}$ alkyl. For example, ring B may represent a 1,4-phenylene or 1,3-phenylene group which is unsubstituted or substituted by 1, 2 or 3 substituents which are the same or different and are selected from fluorine, chlorine, methyl and ethyl.

In each of the above (a) to (c), $R^8$ is a group —COOH or an ester group of formula —(C=O)$OR^{14}$ wherein $R^{14}$ is $R^{15}R^{16}R^{17}C$— wherein either $R^{15}$ is hydrogen or $C_{1-3}$alkyl-$(Z^1)_a$-[$(C_1$-$C_3)$alkyl]$_b$- wherein a and b are independently 0 or 1 and $Z^1$ is —O—, —S—, or —NH— and $R^{16}$ and $R^{17}$ are independently hydrogen or $C_{1-3}$ alkyl-; or $R^{15}$ and $R^{16}$ taken together with the carbon to which they are attached form a 3- to 7-membered cycloalkyl ring and $R^{17}$ is hydrogen.

Preferably, the group [Linker]-R corresponds to (b) or (c) above.

More preferably, the present invention provides a compound of formula (I) or a pharmaceutically acceptable salt, N-oxide, hydrate or solvate thereof, in which:

ring A represents a phenyl group, said ring A group being unsubstituted or substituted by 1, 2 or 3 substituents which are the same or different and are selected from halogen atoms and unsubstituted $C_{1-4}$ alkyl, $C_{1-4}$ alkoxy, hydroxyl and —$NR^3R^4$ groups, wherein $R^3$ and $R^4$ are the same or different and represent hydrogen or unsubstituted $C_{1-2}$ alkyl;

$R^1$ and $R^2$ each represent hydrogen;

n is 1;

X is NH;

V is —N=;

W is —C(H)=; and ring B represents a 1,4-phenylene group, 1,3-phenylene group, 1,3-pyrazolyl group or pyridinyl group, in particular a 1,4-phenylene group, 1,3-phenylene group or 1,3-pyrazolyl group, said ring B group being unsubstituted or substituted by 1, 2 or 3 substituents which are the same or different and are selected from halogen atoms and unsubstituted $C_{1-4}$ alkyl, $C_{1-4}$ alkoxy, hydroxyl and —$NR^3R^4$ groups, wherein $R^3$ and $R^4$ are the same or different and represent hydrogen or unsubstituted $C_{1-2}$ alkyl.

In this embodiment of the invention, the group [Linker]-R preferably corresponds to one of (a) to (c) as set out above, preferably (b) or (c). More preferably, the group [Linker]-R corresponds to (a'), (b') or (c') set out below:

(a') R represents a group of formula (X);
$R^8$ is as set out below;
one of $R^9$ and $R^{10}$ is hydrogen or unsubstituted $C_{1-4}$ alkyl and the other is an unsubstituted $C_{1-6}$ alkyl group;
$R^{11}$ represents a hydrogen atom or an unsubstituted $C_{1-2}$ alkyl group;
[Linker] represents —(CH$_2$)$_v$—, wherein v is 1 or 2.

(b') R represents a group of formula (Y1');
$R^8$ is as set out below;
[Linker] is —(CH$_2$)$_v$— or —C(=O)—, wherein v is 1 or 2.

(c') R represents a group of formula (Y2);
$R^8$ is as set out below;
[Linker] is —C(=O)$NR^7$—, —CH$_2NR^7$— or —CH$_2$C(=O)$NR^7$—, wherein $R^7$ represents hydrogen, unsubstituted methyl, unsubstituted ethyl, unsubstituted isobutyl or —C(=O)CH$_3$.

Typically, in this embodiment, when R is Y2, ring D is a 5- to 7-membered saturated heterocyclyl group having at least one nitrogen atom in the ring, wherein $R^8$ and $R^{11}$ are linked to a ring carbon adjacent to a ring nitrogen, and wherein the bond shown intersected by a wavy line is from a carbon atom in ring D, with the proviso that D is not a pyrrolidinyl group. D may, for example, be a pyrrolyl, piperidinyl, imidazolyl, oxazolyl, isoxazolyl, thiazolyl, thiadiazolyl, pyrazolyl, pyridinyl, pyridazinyl, pyrimidinyl, pyrazinyl, morpholinyl, piperazinyl group, for instance a piperidinyl or piperazinyl group, for example a piperidinyl group.

In this embodiment, preferably, ring B represents a 1,4-phenylene group, 1,3-phenylene group or pyridinyl group, in particular a 1,4-phenylene or 1,3-phenylene group, said ring B group being unsubstituted or substituted by 1, 2 or 3 substituents which are the same or different and are selected from halogen atoms and unsubstituted $C_{1-4}$ alkyl, $C_{1-4}$ alkoxy, hydroxyl and —$NR^3R^4$ groups, wherein $R^3$ and $R^4$ are the same or different and represent hydrogen or unsubstituted $C_{1-2}$ alkyl. For example, ring B may represent a 1,4-phenylene or 1,3-phenylene group which is unsubstituted or substituted by 1, 2 or 3 substituents which are the same or different and are selected from fluorine, chlorine, methyl and ethyl.

In each of the above (a') to (c'), $R^8$ is a group —COOH or an ester group of formula —(C=O)$OR^{14}$ wherein $R^{14}$ is $R^{15}R^{16}R^{17}C$— wherein either $R^{15}$ is hydrogen or $C_{1-3}$ alkyl -$(Z^1)_a$-[$(C_1$-$C_3)$alkyl]$_b$- wherein a and b are independently 0 or 1 and $Z^1$ is —O—, —S—, or —NH— and $R^{16}$ and $R^{17}$ are independently hydrogen or $C_{1-3}$ alkyl-; or $R^{15}$ and $R^{16}$ taken together with the carbon to which they are attached form a 3- to 7-membered cycloalkyl ring and $R^{17}$ is hydrogen. Preferably $R^8$ is a group —COOH or an ester group of formula —(C=O)$OR^{14}$ wherein $R^{14}$ is cyclopentyl or t-butyl.

Preferably, the group [Linker]-R corresponds to (b') or (c') above.

Particularly preferred compounds of the invention are:

Cyclopentyl (2R)-4-[(4-{5-amino-6-[(2,6-dichlorobenzyl)amino]pyrazin-2-yl}benzyl)amino]piperidine-2-carboxylate Cyclopentyl 4-(4-{5-amino-6-[(2,6-dichlorobenzyl)amino]pyrazin-2-yl}benzyl)piperazine-2-carboxylate Cyclopentyl (2S)-4-(4-{5-amino-6-[(2,6-dichlorobenzyl)amino]pyrazin-2-yl}benzyl)piperazine-2-carboxylate Cyclopentyl (2R)-4-(4-{5-amino-6-[(2,6-dichlorobenzyl)amino]pyrazin-2-yl}benzyl)piperazine-2-carboxylate Cyclopentyl (2R)-4-[(4-{5-amino-6-[(2,6-dichlorobenzyl)amino]pyrazin-2-yl}-2-chlorobenzyl)amino]piperidine-2-carboxylate Cyclopentyl (2R)-4-[(4-{5-amino-6-[(2,6-dichlorobenzyl)amino]pyrazin-2-yl}benzyl)(ethyl)amino]piperidine-2-carboxylate Cyclopentyl (2R)-4-[(4-{5-amino-6-[(2,6-dichlorobenzyl)amino]pyrazin-2-yl}benzyl)(methyl)amino]piperidine-2-carboxylate tert-Butyl (2R)-4-[(4-{5-amino-6-[(2,6-dichlorobenzyl)amino]pyrazin-2-yl}benzyl)(ethyl)amino]piperidine-2-carboxylate
Cyclopentyl (2R)-4-[acetyl(4-{5-amino-6-[(2,6-dichlorobenzyl)amino]pyrazin-2-yl}benzyl)amino]piperidine-2-carboxylate
Cyclopentyl (2R)-4-(3-{5-amino-6-[(2,6-dichlorobenzyl)amino]pyrazin-2-yl}benzyl)piperazine-2-carboxylate
Cyclopentyl 1-[(3-{5-amino-6-[(2,6-dichlorobenzyl)amino]pyrazin-2-yl}benzyl)amino]cyclobutanecarboxylate
Cyclopentyl N-[2-(3-{5-amino-6-[(2,6-dichlorobenzyl)amino]pyrazin-2-yl}phenyl)ethyl]-2-methylalaninate
Cyclopentyl (2S)-4-(3-{5-amino-6-[(2,6-dichlorobenzyl)amino]pyrazin-2-yl}benzyl)piperazine-2-carboxylate
Cyclopentyl 4-(4-{5-amino-6-[(2,6-dichlorobenzyl)amino]pyrazin-2-yl}-2-ethylbenzyl)piperazine-2-carboxylate Utilities As mentioned above, the compounds with which the invention is concerned are inhibitors of CSF-1R kinase, and are therefore of use in the treatment of a variety of diseases. Accordingly, the present invention provides a compound as defined herein for use in a method of treatment of the human or animal body.

In particular, the present invention provides a compound as defined herein for use in the treatment of a disease or disorder mediated by CSF-1R kinase, including cell proliferative disease such as cancer and psoriasis, polyglutamine disease such as Huntingdon's disease, neurodegenerative disease such as Alzheimers disease, autoimmune disease such as rheumatoid arthritis, diabetes, haematological disease, inflammatory disease, cardiovascular disease, atherosclerosis, and the inflammatory sequelia of infection.

The present invention also provides a method of treating or preventing a disease or disorder mediated by CSF-1R kinase in a subject, which method comprises administering to said subject an effective amount of a compound as defined herein, and use of a compound as defined herein in the manufacture of a medicament for use in the treatment or prevention of a disease or disorder mediated by CSF-1R kinase. In particular, there is provided a method of treating or preventing cell proliferative disease such as cancer and psoriasis, polyglutamine disease such as Huntingdon's disease, neurodegenerative disease such as Alzheimers disease, autoimmune disease such as rheumatoid arthritis, diabetes, haematological disease, inflammatory disease, cardiovascular disease, atherosclerosis, and the inflammatory sequelia of infection, by administering an effective amount of a compound of formula (I) as defined herein. Also provided is use of a compound of formula (I) as defined herein in the manufacture of a medicament for use in the treatment or prevention of cell proliferative disease such as cancer and psoriasis, polyglutamine disease such as Huntingdon's disease, neurodegenerative disease such as Alzheimers disease, autoimmune disease such as rheumatoid arthritis, diabetes, haematological disease, inflammatory disease, cardiovascular disease, atherosclerosis, and the inflammatory sequelia of infection.

Autoimmune disease often has an inflammatory component. Such conditions include acute disseminated alopecia universalise, ANCA positive diseases, Behcet's disease, Chagas' disease, chronic fatigue syndrome, dysautonomia, encephalomyelitis, ankylosing spondylitis, aplastic anemia, hidradenitis suppurativa, autoimmune hepatitis, autoimmune oophoritis, celiac disease, inflammatory bowel disease, Crohn's disease, diabetes mellitus type 1, Fanconi syndrome, giant cell arteritis, glomerulonephritis, Goodpasture's syndrome, Grave's disease, Guillain-Barre syndrome, Hashimoto's disease, Henoch-Schönlein purpura, Kawasaki's disease, systemic lupus erythematosus, microscopic colitis, microscopic polyarteritis, mixed connective tissue disease, multiple sclerosis, myasthenia gravis, opsocionus myoclonus syndrome, optic neuritis, Ord's thyroiditis, pemphigus, polyarteritis nodosa, polymyalgia, rheumatoid arthritis, Reiter's syndrome, Sjogren's syndrome, temporal arteritis, Wegener's granulomatosis, warm autoimmune haemolytic anemia, interstitial cystitis, lyme disease, morphea, psoriasis, sarcoidosis, scleroderma, ulcerative colitis, and vitiligo.

Other inflammatory conditions which may be treated with the compounds of the invention include, for example, appendicitis, dermatitis, dermatomyositis, endocarditis, fibrositis, gingivitis, glossitis, hepatitis, hidradenitis suppurativa, iritis, laryngitis, mastitis, myocarditis, nephritis, otitis, pancreatitis, parotitis, percarditis, peritonoitis, pharyngitis, pleuritis, pneumonitis, prostatistis, pyelonephritis, and stomatisi, transplant rejection (involving organs such as kidney, liver, heart, lung, pancreas (e.g., islet cells), bone marrow, cornea, small bowel, skin allografts, skin homografts, and heart valve xengrafts, sewrum sickness, and graft vs host disease), acute pancreatitis, chronic pancreatitis, acute respiratory distress syndrome, Sexary's syndrome, congenital adrenal hyperplasia, nonsuppurative thyroiditis, hypercalcemia associated with cancer, pemphigus, bullous dermatitis herpetiformis, severe erythema multiforme, exfoliative dermatitis, seborrheic dermatitis, seasonal or perennial allergic rhinitis, bronchial asthma, contact dermatitis, astopic dermatitis, drug hypersensistivity reactions, allergic conjunctivitis, keratitis, herpes zoster ophthalmicus, iritis and oiridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) haemolytic anemia, leukaemia and lymphomas in adults, acute leukaemia of childhood, regional enteritis, autoimmune vasculitis, multiple sclerosis, chronic obstructive pulmonary disease, solid organ transplant rejection, sepsis, primary biliary cirrhosis and primary sclerosing cholangitis.

Preferred treatments using compounds of the invention include treatment of rheumatoid arthritis, psoriatic arthritis, Type 1 diabetes, asthma, inflammatory bowel disease, systemic lupus erythematosis, and inflammation accompanying infectious conditions (e.g., sepsis), psoriasis, Crohns disease, ulcerative colitis, chronic obstructive pulmonary disease, multiple sclerosis, atopic dermatitis, and graft versus host disease.

Another preferred use of the compounds of the invention is in the treatment of cancers.

The present invention also provides a pharmaceutical composition which comprises a compound of formula (I) as defined herein and one or more pharmaceutically acceptable carrier(s) and/or excipients.

It will be understood that the specific dose level for any particular subject will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial. However, it is expected that a typical dose will be in the range from about 0.001 to 50 mg per kg of body weight.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers for example lactose, sugar, maize-starch, calcium phosphate, sorbitol or glycine; tabletting lubricant, for example magnesium stearate, talc, polyethylene glycol or silica; disintegrants for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application by inhalation, the drug may be formulated for aerosol delivery for example, by pressure-driven jet atomizers or ultrasonic atomizers, or preferably by propellant-driven metered aerosols or propellant-free administration of micronized powders, for example, inhalation capsules or other "dry powder" delivery systems. Excipients, such as, for example, propellants (e.g. Frigen in the case of metered aerosols), surface-active substances, emulsifiers, stabilizers, preservatives, flavorings, and fillers (e.g. lactose in the case of powder inhalers) may be present in such inhaled formulations. For the purposes of inhalation, a large number of apparata are available with which aerosols of optimum particle size can be generated and administered, using an inhalation technique which is appropriate for the subject. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described in European Patent Application EP 0 505 321).

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agent can be dissolved in the vehicle.

The compounds of the invention may be administered as part of a pharmaceutical combination, which combination comprises compounds of the invention and a second inhibitor. If administered as part of a pharmaceutical combination, the compounds can either be administered simultaneously or by any manner of separate sequential administration of therapeutically effective amounts. It does not matter if the compounds are administered in the same dosage form, e.g., one compound may be administered topically and the other compound may be administered orally. The administration of a therapeutically effective amount of combinations of inhibitors may be advantageous over the administration of a single inhibitor in that the combination may provide one or more of the following improved properties when compared to the individual administration of a therapeutically effective amount of a component compound: i) a greater therapeutic effect that the most active single agent, ii) synergistic or highly synergistic activity, iii) a dosing protocol that provides a reduced side effect profile, iv) a reduction in the toxic effect profile, v) an increase in the therapeutic window, or vi) an increase in the bioavailability of one or both of the component compounds.

Examples of suitable pharmaceutical combinations include the combination of compounds of the present invention with mTor inhibitors, B-Raf inhibitors, AKT inhibitors or PI3 kinase inhibitors.

Synthesis

There are multiple synthetic strategies for the synthesis of the compounds (I) with which the present invention is concerned, but all rely on known chemistry, known to the synthetic organic chemist. Thus, compounds according to formula (I) can be synthesised according to procedures described in the standard literature and are well-known to those skilled in the art. Typical literature sources are "Advanced organic chemistry", $4^{th}$ Edition (Wiley), J March, "Comprehensive Organic Transformation", $2^{nd}$ Edition (Wiley), R. C. Larock, "Handbook of Heterocyclic Chemistry", $2^{nd}$ Edition (Pergamon), A. R. Katritzky), review articles such as found in "Synthesis", "Acc. Chem. Res.", "Chem. Rev", or primary literature sources identified by standard literature searches online or from secondary sources such as "Chemical Abstracts" or "Beilstein".

The compounds of the invention may be prepared by a number of processes generally described below and more specifically in the Examples hereinafter. In the reactions described below, it may be necessary to protect reactive functional groups, for example hydroxyl, amino and carboxy groups, where these are desired in the final product, to avoid their unwanted participation in the reactions [see for example Greene, T. W., "Protecting Groups in Organic Synthesis", John Wiley and Sons, 1999]. Conventional protecting groups may be used in conjunction with standard practice. In some instances deprotection may be the final step in the synthesis of a compound of general formula (I), and the processes according to the invention described herein after are understood to extend to such removal of protecting groups.

The schemes detailed below show general schemes for synthesizing compounds of formula (I). It is recognised that the compounds corresponding to Roman numerals in the schemes below do not correspond to Roman numerals of claimed compounds employed in other sections of this application.

Compounds of general formula (VII) may be prepared by, but not limited to, the reactions set out in Scheme A.

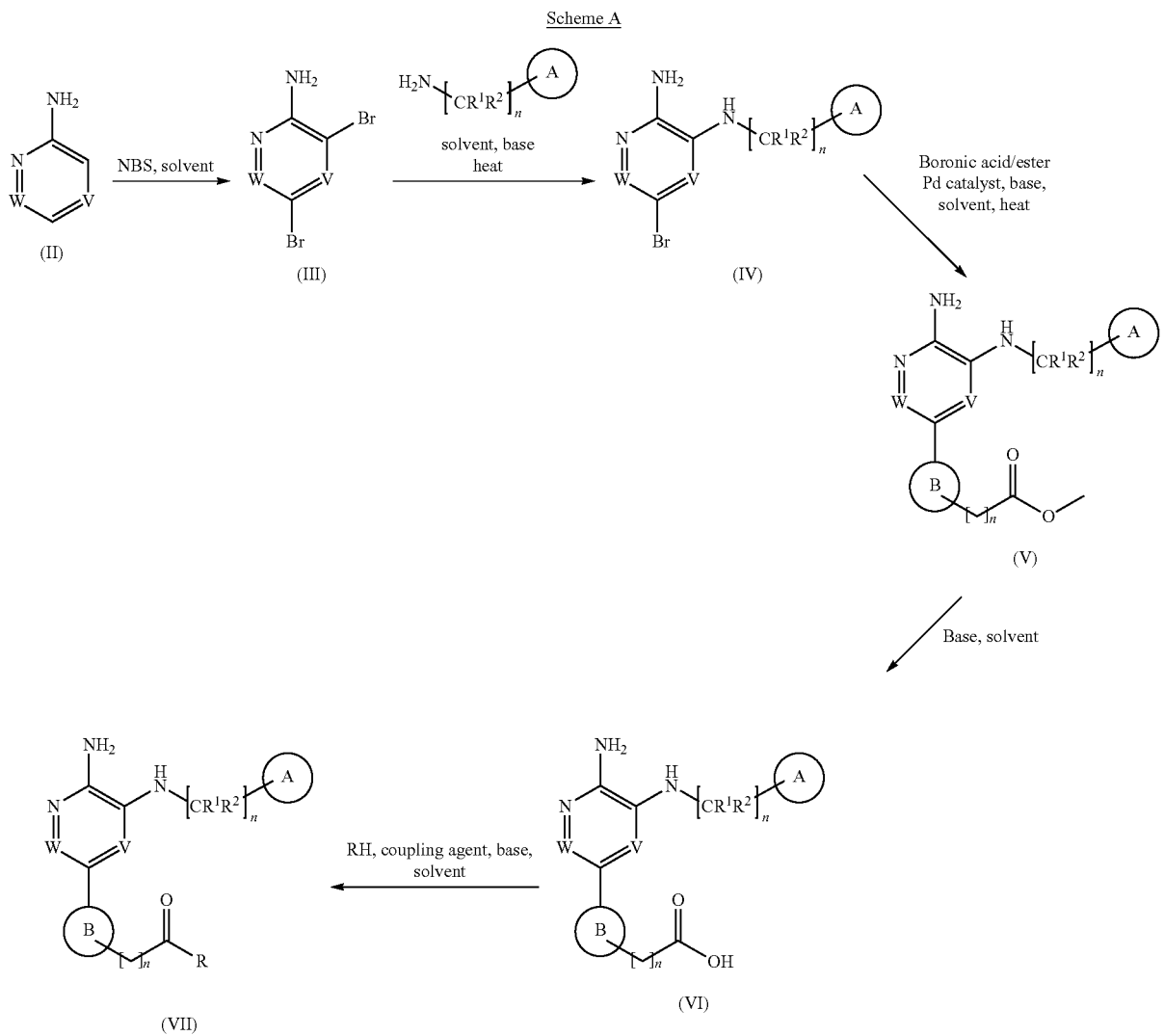

where R = X, Y1', NR⁷Y2'
n = 0, 1

The compound with formula (II), 2-aminopyrazine, is commercially available. 2-Aminopyrazine may be converted into the compound of formula (III) by reaction with a brominating agent such as N-bromosuccinimide in a suitable solvent such as DCM, at a temperature of 0° C.

Compounds of formula (IV) may be obtained from the compound of formula (III) by selective nucleophilic aromatic substitution by attack with benzylic amines. The reaction may be performed in a suitable solvent such as n-butanol and in the presence of a base such as DIPEA under microwave irradiation at a temperature of 150° C.

Compounds of formula (V) can be obtained from compounds of formula (IV) by reaction with appropriate aromatic boronic esters or acids, using Suzuki coupling conditions. The Suzuki couplings may be performed in the presence of a catalyst such as dichlorobis(triphenylphosphine) palladium (II), a base such as $Na_2CO_3$ and in a solvent such as DME at a temperature of 80° C. It will be appreciated that to those skilled in the art, various substituted heterocyclic and substituted aromatic boronic esters and acids can be reacted with compounds of formula (IV) under Suzuki coupling conditions to synthesise ring B analogues of compounds of formula (V). Compounds of formula (VI) can be obtained from compounds of formula (V) by reaction with a base such as lithium hydroxide or sodium hydroxide in a solvent such as ethanol, methanol, or THF and water at temperatures ranging from RT to reflux. Compounds of formula (VI) can be treated with an appropriate amine functionality and a suitable coupling agent, such as 1-ethyl-3-(3-dimethylaminopropyl) carbodiimide in a presence of N-hydroxybenzotriazole, in an aprotic solvent such as N,N-dimethylformamide at room temperature.

Compounds of general formula (IX) may be prepared by, but not limited to, the reactions set out in Scheme B.

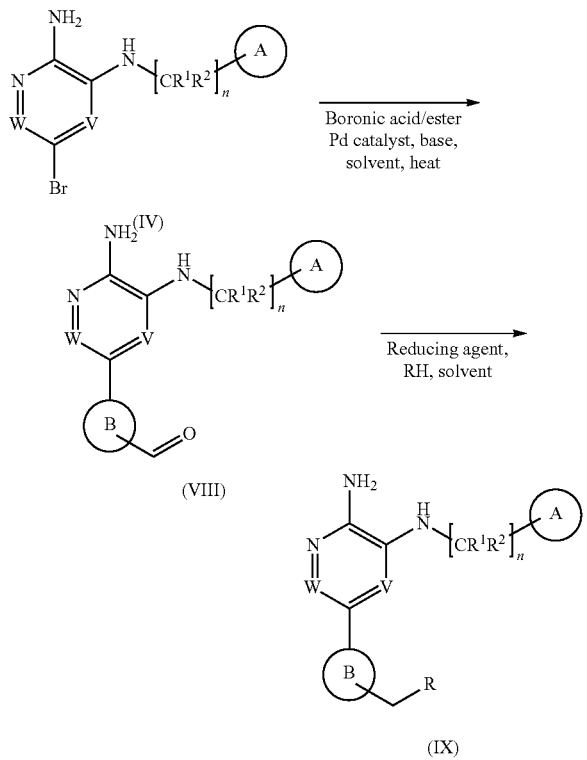

where R = X, Y1', NR⁷Y2'

Compounds of formula (IV) can be converted into compounds of formula (VIII) using the conditions as described for the preparation of compounds of formula (V) (Scheme A).

Compounds of formula (IX) may be prepared from compounds of formula (VIII) under reductive amination conditions with a suitable amine using an appropriate reducing agent such as sodium triacetoxyborohydride in a suitable solvent such as DCE.

In the above Schemes A and B, the amino groups in the compound of formula (VI) may first be protected by an appropriate method for the protection of an amino group, known to those skilled in the art. A suitable protecting group for an amino group is, but not limited to, for example an acyl group, an alkanoyl group such as acetyl, an alkoxycarbonyl group such as a methoxycarbonyl, ethoxycarbonyl or tert-butoxycarbonyl group, an arylmethoxycarbonyl group, such as benzyloxycarbonyl or an aroyl group, such as benzoyl. The final stage of the reaction may then be an amino group deprotection, using the necessary deprotection conditions which vary depending with the choice of protecting group used. Thus, for example, an acyl group such as alkanoyl, an alkoxycarbonyl group or an aroyl group may be removed by hydrolysis with a suitable base such as an alkali metal hydroxide, for example lithium hydroxide or sodium hydroxide. Alternatively an acyl group such as a tert-butoxycarbonyl group may be removed, for example, by treatment with a suitable acid such as hydrochloride, sulphuric or trifluoroacetic acid and an arylmethoxycarbonyl group such as a benzyloxycarbonyl group may be removed, for example, by hydrogenation over a catalyst such as palladium on carbon.

Compounds of general formula (X) and (XI) may be prepared by, but not limited to, the reactions set out in Scheme C.

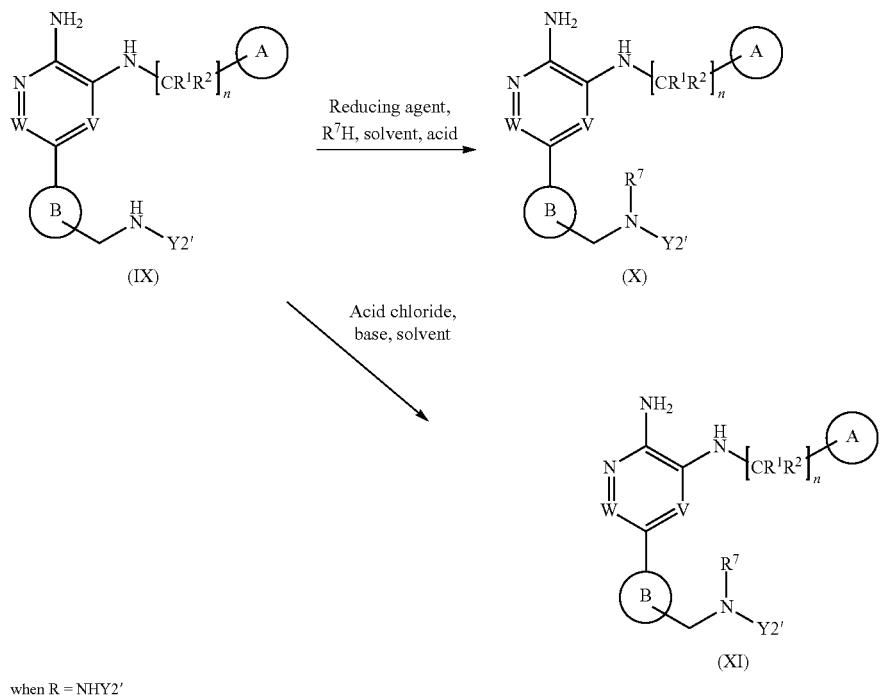

when R = NHY2'

Compounds of formula (IX), when R=NHY2' can be converted into compounds of formula (X) using the conditions as described for the preparation of compounds of formula (IX) (Scheme B) with or without the addition of an acid such as acetic acid. Alternatively compounds of formula (IX), where R=NHY2', can be converted into compounds of formula (XI) by an amide bond formation, by reaction with acid chlorides in a suitable solvent such as DCM at temperatures ranging of 0° C.-room temperature.

Compounds of general formula (XVI) may be prepared by, but not limited to, the reactions set out in Scheme D.

the necessary deprotection conditions which vary depending with the choice of protecting group used, for example using one of the methods described above.

A compound of formula (VII), (IX) or (XVI) in which R is Y1' or NR$^7$Y2'/NHY2' may be formed by (i) reacting a compound of formula (VI), (VIII) or (XIV) according to Schemes A, B and D respectively with an amino functionality in which the ring nitrogen is substituted by a group R', for example tert-butoxycarbonyl, and (ii) treating the resulting compound with a suitable acid such as hydrochloric acid or trifluoroacetic acid.

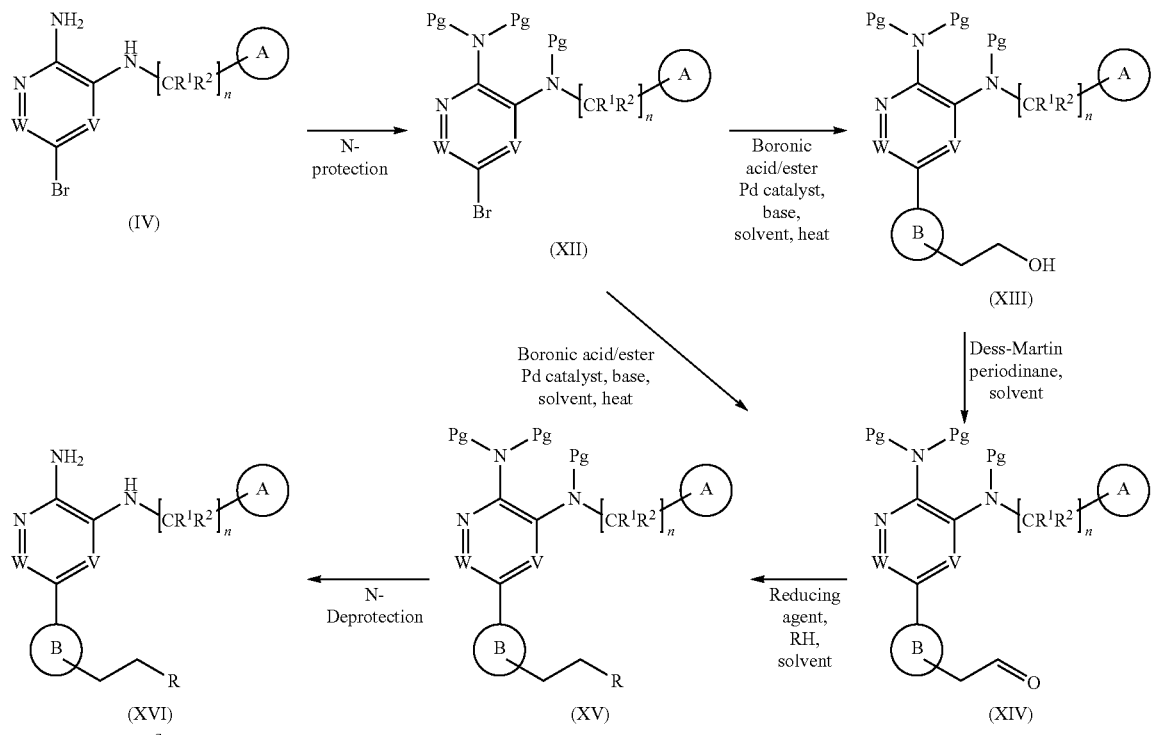

Scheme D

Compounds of formula (IV) can be converted to compounds of formula (XII) by an appropriate method for the protection of an amino group, known to those skilled in the art. Suitable protecting groups (Pg) are those described above.

Compounds as formula (XIII) may be obtained from compounds of formula (XII) using the conditions as described for the preparation of compounds of formula (V) (Scheme A). Compounds of formula (XIII) may be transformed to compounds of formula (XIV) by oxidation using an oxidising agent such as Dess-Martin periodinane in an appropriate solvent such as DCM. Alternatively compounds of formula (XIV) can be obtained directly from compounds of formula (XII) by reaction with the appropriate substituted boronic acid or ester using the conditions as described for the preparation of compounds of formula (V) (Scheme A).

Compounds of formula (XV) may be prepared from compounds of formula (XIV) by reductive amination using the conditions as described for the preparation of compounds of formula (IX) (Scheme B).

Compounds of formula (XVI) can be prepared by amino group deprotection of the compounds of formula (XV) using A number of examples illustrative of the present invention are described below. In most cases, alternative techniques could also be used. In the following examples, it is understood that the solvents and reagents used or suggested are not limiting and can be substituted appropriately with solvents and reagents known to those of skill in the art. Reaction products may be isolated by means known in the art, such as extraction with a suitable solvent, precipitation from a suitable solvent, chromatography using a suitable solvent system, including silica gel column chromatography, HPLC and the like.

The compounds of the invention may be synthesised by a number of processes generally described above and more specifically in the Examples hereinafter. Thus compounds of general formula (I) may be prepared by, but not restricted to methods set out in Schemes 1-30.

EXAMPLES

Abbreviations
Boc=tert-butoxycarbonyl
Cs$_2$CO$_3$=cesium carbonate

DCE=1,2-dichloroethane
DCM=dichloromethane
DIPEA=diisopropylethylamine
DMAP=dimethylamino pyridine
DMF=dimethylformamide
DMSO=dimethyl sulfoxide
EDC=1-(3-dimethylaminopropyl)-3-ethylcarbodiimide hydrochloride
EtOAc=ethyl acetate
HCl=hydrochloric acid
HOBt=1-hydroxybenzotriazole
HPLC=high performance liquid chromatography
KOAc=potassium acetate
LCMS=high performance liquid chromatography/mass spectrometry
MeCN=acetonitrile
MeOH=methanol
$MgSO_4$=magnesium sulphate
$Na_2CO_3$=sodium carbonate
$NaHCO_3$=sodium hydrogen carbonate
NaOH=sodium hydroxide
NMR=nuclear magnetic resonance
$PdCl_2(dppf)_2$=1,1'-Bis(diphenylphosphino)ferrocene-palladium(II)dichloride
ppm=parts per million
RT=room temperature
STAB=sodium triacetoxyborohydride
TBME=tert-butyl methyl ether
THF=tetrahydrofuran
hrs=hours
mins=minutes
g=gram(s)
mg=milligram(s)
L=liter(s)
mL=milliliter(s)
μL=microliter(s)
mol=mole(s)
mmol=millimole(s)
sat=saturated Commercially available reagents and solvents (HPLC grade) were used without further purification. Solvents were removed using a Buchi rotary evaporator. Microwave irradiation was carried out using a Biotage Initiator™ Eight microwave synthesiser. Purification of compounds by flash chromatography column was performed using silica gel, particle size 40-63 μm (230-400 mesh) obtained from Fluorochem. Automated flash column chromatography was performed on Combiflash® or Companion® systems equipped with Telos, Biotage® or GraceResolv cartridges. Purification of compounds by preparative HPLC was performed on Gilson systems using reverse phase Waters XSelect C18 column (5 u, 50×19 mm) using the gradient method described below.

Gradient 10-100% B (A=water/0.1% formic acid, B=acetonitrile) over 10 min, flow =20 mL/min, UV detection at 254 nm. Alternatively, the formic acid can be replaced with $(NH_4)_2CO_3$ in the aqueous buffer.

$^1$H NMR spectra were recorded on a Bruker 300 MHz AV spectrometer in deuterated solvents. Chemical shifts (δ) are in parts per million. Thin-layer chromatography (TLC) analysis was performed with Kieselgel 60 $F_{254}$ (Merck) plates and visualized using UV light.

Analytical HPLC/MS was performed on an Agilent HP1100 LC system using reverse phase Luna C18 columns (3 μm, 50×4.6 mm), gradient 5-95% B (A=water/0.1% Formic acid, B=acetonitrile/0.1% Formic acid) over 2.25 min, flow=2.25 mL/min. UV spectra were recorded at 220 and 254 nm using a G1315B DAD detector. Mass spectra were obtained over the range m/z 150 to 800 on a LC/MSD SL G1956B detector. Data were integrated and reported using ChemStation and ChemStation Data Browser software.

INTERMEDIATES

Intermediate 1

5-Bromo-$N^3$-(2,6-dichlorobenzyl)pyrazine-2,3-diamine

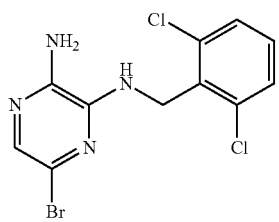 [SMILES: Nc1ncc(Br)nc1NCc1c(Cl)cccc1Cl]

5-Bromo-$N^3$-(2,6-dichlorobenzyl)pyrazine-2,3-diamine was synthesised using the route shown in Scheme 1.

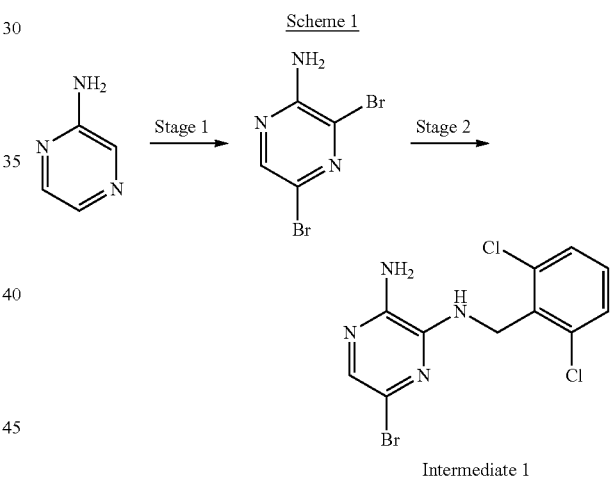

Intermediate 1

Stage 1. 3,5-Dibromopyrazin-2-amine

To a solution of aminopyrazine (11.36 g, 0.12 mol) in DCM (700 mL) at 0° C. was added N-bromosuccinimide (44.64 g, 0.25 mol) portion-wise. The reaction was stirred for 2 hrs. The reaction was washed with sat $Na_2CO_3$ (3×200 mL), dried over $MgSO_4$, filtered and concentrated in vacuo before purification by column chromatography (20% EtOAc/heptane) to give the title compound as a yellow solid (15.9 g, 53%). LCMS: m/z 252/254/256 [M+H]$^+$.

Stage 2. 5-Bromo-$N^3$-(2,6-dichlorobenzyl)pyrazine-2,3-diamine

To a solution of 3,5-dibromopyrazin-2-amine (5.01 g, 19.8 mmol) in n-butanol (5 mL) was added 2,6-dichlorobenzylamine (10.47 g, 59.4 mmol) and DIPEA (3.8 mL, 21.8 mmol). The reaction was heated with microwaves at 150° C.

for 4 hrs. The reaction was poured onto EtOAc (100 mL) and washed with water (50 mL), brine (50 mL), dried over MgSO$_4$, filtered and concentrated in vacuo. The resulting solid was triturated with heptane and then DCM (40 mL) was added and the suspension was vigorously stirred for 15 mins. The solid was collected by filtration to give the title compound as an off-white solid (5.14 g, 75%).

LCMS: m/z 347/349/381 [M+H]$^+$.

$^1$H NMR (300 MHz, CD$_3$OD) δ ppm: 7.45-7.43 (2H, m), 7.32 (1H, dd, J=7.2, 8.9 Hz), 7.21 (1H, s), 4.81 (2H, s).

Intermediate 2

5-Bromo-N$^3$-(2,6-difluorobenzyl)pyrazine-2,3-diamine

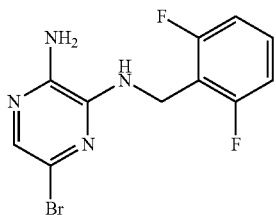 [SMILES: Nc1ncc(Br)nc1NCc1c(F)cccc1F]

5-Bromo-N$^3$-(2,6-difluorobenzyl)pyrazine-2,3-diamine was synthesised in a similar manner to Intermediate 1 using 2,6-difluorobenzylamine as the reactant in Stage 2 of the route shown in Scheme 1. The product was purified by automated column chromatography using EtOAc in heptane (gradient 0-40%).

LCMS: m/z 315/317 [M+H]$^+$.

$^1$H NMR (300 MHz, CDCl$_3$) δ ppm: 7.49 (1H, s), 7.4-7.2 (1H, m), 7.07-6.85 (2H, m), 4.71 (2H, d, J=1.8 Hz), 4.70-4.55 (1H, m), 4.30 (2H, br, s).

Intermediate 3

5-Bromo-N$^3$-(2-chloro-6-fluorobenzyl)pyrazine-2,3-diamine

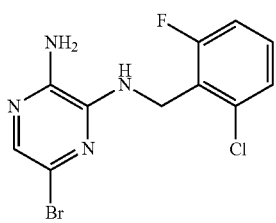 [SMILES: Nc1ncc(Br)nc1NCc1c(F)cccc1Cl]

5-Bromo-N$^3$-(2-chloro-6-fluorobenzyl)pyrazine-2,3-diamine was synthesised in a similar manner to Intermediate 1 using 2-fluoro-6-chlorobenzylamine as the reactant in Stage 2 of the route shown in Scheme 1. The product was purified by automated column chromatography using EtOAc in heptane (gradient 0-70%).

LCMS: m/z 331/333 [M+H]$^+$.

$^1$H NMR (300 MHz, CDCl$_3$) δ ppm: 7.6-7.47 (1H, m), 7.42-7.17 (2H, m), 7.15-6.95 (1H, m), 4.78 (2H, dd, J=1.8, 0.5 Hz), 4.63-4.95 (1H, m), 4.06 (2H, br, s).

Intermediate 4

Di-tert-butyl {5-bromo-3-[(tert-butoxycarbonyl)(2,6-dichloro benzyl)amino]pyrazin-2-yl}imidodicarbonate

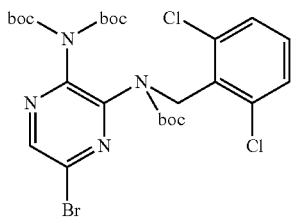

boc = tert-butoxycarbonyl

Di-tert-butyl {5-bromo-3-[(tert-butoxycarbonyl)(2,6-dichlorobenzyl)amino]pyrazin-2-yl}imidodicarbonate was prepared by the route shown in Scheme 2.

Scheme 2

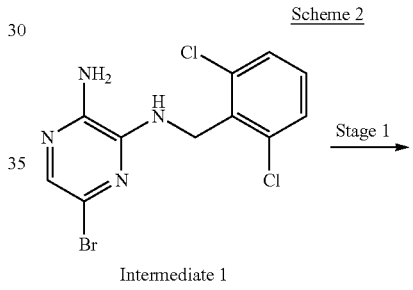

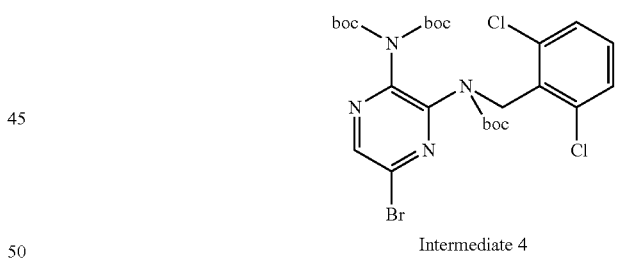

Stage 1: Di-tert-butyl {5-bromo-3-[(tert-butoxycarbonyl)(2,6-dichlorobenzyl) amino]pyrazin-2-yl}imidodicarbonate To a solution of Intermediate 1 (3.76 g, 10.8 mmol) in DCE (60 mL) at 60° C. was added DMAP (0.13 g, 1.08 mmol) followed by di-tert-butyl dicarbonate (14.1 g, 65.0 mmol) dissolved in DCE (5 mL). The reaction mixture was stirred at 60° C. for 4 hrs for complete reaction. The reaction was allowed to cool to RT before water (60 mL) was added. The organic layer was separated and the aqueous layer was extracted with DCM (2×60 mL). The combined organics were dried over MgSO$_4$, filtered and concentrated in vacuo to an orange oil which was purified by column chromatography (10% EtOAc/heptane) to give the title compound as a yellow solid (3.98 g, 57%).

¹H NMR (300 MHz, CDCl₃) δ ppm: 8.40 (1H, s), 7.32 (1H, m), 7.29 (1H, s), 7.18 (1H, dd, J=8.7, 6.9 Hz), 5.12 (2H, s), 1.56 (18H, s), 1.47 (9H, s).

Intermediate 5

3-(4,4,5,5-Tetramethyl-1,3,2-dioxaborolan-2-yl)benzaldehyde

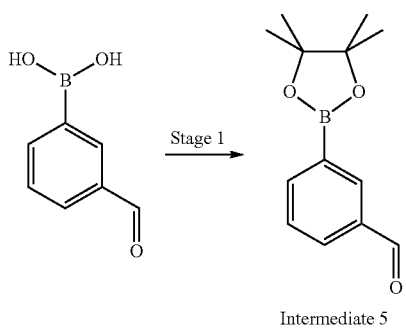

3-(4,4,5,5-Tetramethyl-1,3,2-dioxaborolan-2-yl)benzaldehyde was prepared by the route shown in Scheme 3 below.

Scheme 3

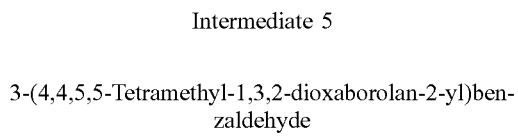

Intermediate 5

Stage 1. 3-(4,4,5,5-Tetramethyl-1,3,2-dioxaborolan-2-yl)benzaldehyde

To a solution of 3-formyl phenylboronic acid (5 g, 33 mmol) in anhydrous THF (50 mL) was added pinacol (4.34 g, 37 mmol). The reaction mixture was allowed to stir at RT under nitrogen for 18 hrs before concentration in vacuo. The crude residue was dissolved in DCM (150 mL) and washed with water (3×100 mL). The organic layer was dried over MgSO₄ and evaporated in vacuo to give the title compound as a yellow oil (7.73 g, 100%).

¹H NMR (300 MHz, CDCl₃) δ ppm: 10.06 (1H, s), 8.31 (1H, s), 8.07 (1H, d, J=7.4 Hz), 7.99 (1H, dt, J=1.5, 7.4 Hz), 7.54 (1H, t, J=7.4 Hz), 1.38 (12H, s).

Intermediate 6

4-(4,4,5,5-Tetramethyl-1,3,2-dioxaborolan-2-yl)benzaldehyde

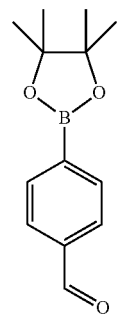

4-(4,4,5,5-Tetramethyl-1,3,2-dioxaborolan-2-yl)benzaldehyde was synthesised in a similar manner to Intermediate 5 using (4-formylphenyl)boronic acid as the starting material in Scheme 3.

¹H NMR (300 MHz, CDCl₃) δ ppm: 10.06 (1H, s), 7.97 (2H, d, J=8.1 Hz), 7.87 (2H, d, J=8.1 Hz), 1.37 (12H, s).

Intermediate 7

2-Ethyl-4-(4,4,5,5-tetramethyl-1,3,2-dioxaborolan-2-yl)benzaldehyde

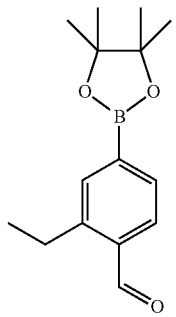 [SMILES: CCc1cc(B2OC(C)(C)C(C)(C)O2)ccc1C=O]

2-Ethyl-4-(4,4,5,5-tetramethyl-1,3,2-dioxaborolan-2-yl)benzaldehyde was synthesised in a similar manner to Intermediate 5 using 3-ethyl-4-formylphenylboronic acid as the starting material in Scheme 3.

¹H NMR (300 MHz, CDCl₃) δ ppm: 10.34 (1H, s), 7.85-7.74 (3H, m), 3.09 (2H, q, J=7.5 Hz), 1.38 (12H, s), 1.29 (3H, t, J=7.5 Hz).

Intermediate 8

2-[3-(4,4,5,5-Tetramethyl-1,3,2-dioxaborolan-2-yl)phenyl]ethanol

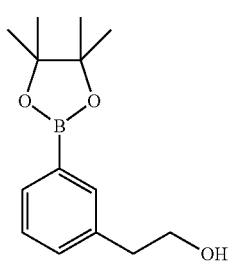 [SMILES: CC1(C)OB(c2cccc(CCO)c2)OC1(C)C]

2-[3-(4,4,5,5-Tetramethyl-1,3,2-dioxaborolan-2-yl)phenyl]ethanol was prepared by the route shown in Scheme 4 below.

Scheme 4

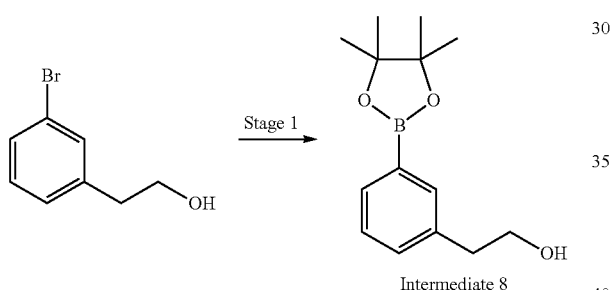

Intermediate 8

Stage 1: 2-[3-(4,4,5,5-Tetramethyl-1,3,2-dioxaborolan-2-yl)phenyl]ethanol

To a solution of 2-(3-bromophenyl)-ethanol (3.0 g, 15 mmol) in anhydrous DMSO (30 mL) were added KOAc (4.39 g, 45 mmol), bis(pinacolato)diboron (5.68 g, 22 mmol) and $PdCl_2(dppf)_2$ (0.61 g, 0.74 mmol) and the reaction mixture was heated at 120° C. under a nitrogen atmosphere for 18 hrs. The reaction was cooled to RT and EtOAc (60 mL) was added. The reaction mixture was filtered through Celite®, washing with EtOAc (500 mL). The filtrate was washed with sat $NaHCO_3$ (150 mL), water (150 mL), brine (150 mL), dried over $MgSO_4$, filtered and concentrated in vacuo. The crude material was purified by automated column chromatography using EtOAc in heptane (gradient 0-100%) and then column chromatography (33% EtOAc/heptane) to give the title compound as a pale yellow oil (3.30 g, 89%).

$^1$H NMR (300 MHz, $CDCl_3$) δ ppm: 7.70 (2H, m), 7.35 (2H, m), 3.89 (2H, t, J=6.6 Hz), 2.90 (2H, t, J=6.6 Hz), 1.51 (1H, s), 1.37 (12H, s).

Intermediate 9

2-Methyl-4-(4,4,5,5-tetramethyl-1,3,2-dioxaborolan-2-yl) benzaldehyde

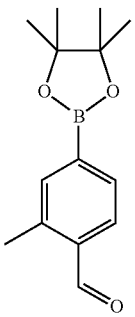

2-Methyl-4-(4,4,5,5-tetramethyl-1,3,2-dioxaborolan-2-yl)benzaldehyde was synthesised in a similar manner to Intermediate 8 using 4-bromo-2-methyl benzaldehyde as starting material in Scheme 4.

LCMS: m/z 430.2 $[2M]^+$.

$^1$H NMR (300 MHz, $CDCl_3$) δ ppm: 10.32 (1H, s), 7.85-7.75 (2H, m), 7.72 (1H, s), 2.69 (3H, s), 1.38 (12H, s).

Intermediate 10

Methyl[4-(4,4,5,5-tetramethyl-1,3,2-dioxaborolan-2-yl)-1H-pyrazol-1-yl]acetate

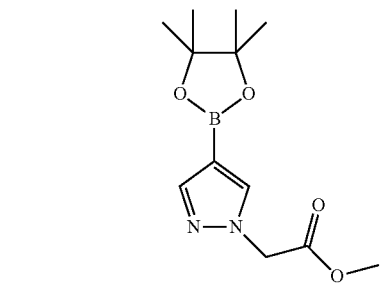

Methyl[4-(4,4,5,5-tetramethyl-1,3,2-dioxaborolan-2-yl)-1H-pyrazol-1-yl]acetate was prepared according to the synthetic route shown in Scheme 5.

Scheme 5

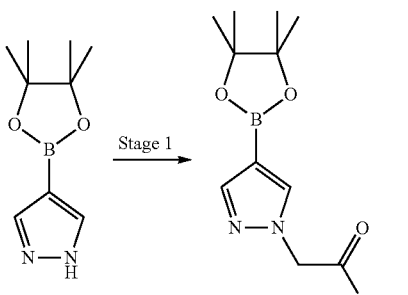

Intermediate 10

To a solution of 4-(4,4,5,5-tetramethyl-1,3,2-dioxaborolan-2-yl)-1H-pyrazole (560 mg, 2.9 mmol) in anhydrous DMF (10 mL) was added $Cs_2CO_3$ (1.03 g, 3.16 mmol) and methyl bromoacetate (0.30 mL, 3.16 mmol) and the reaction was stirred at 90° C. under a nitrogen atmosphere for 18 hrs. The reaction was cooled, diluted with EtOAc (50 mL), washed with water (2×25 mL), brine (25 mL), dried over $MgSO_4$, filtered and concentrated in vacuo. The crude material was purified by column chromatography (50% EtOAc/heptane) to give the title compound as a colourless oil (360 mg, 47%).

LCMS: m/z 267 $[M+H]^+$.

Intermediate 11

2-[4-(4,4,5,5-Tetramethyl-1,3,2-dioxaborolan-2-yl)-1H-pyrazol-1-yl]ethanol

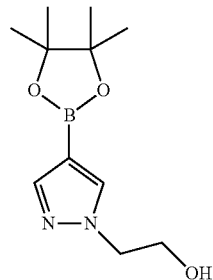 [SMILES: CC1(C)OB(c2cnn(CCO)c2)OC1(C)C]

2-[4-(4,4,5,5-Tetramethyl-1,3,2-dioxaborolan-2-yl)-1H-pyrazol-1-yl]ethanol was synthesised in a similar manner to Intermediate 10 using bromoethanol as the starting material in the route shown in Scheme 5. The crude material was purified by column chromatography (80-100% EtOAc/heptane) to give the title compound as a colourless oil (528 mg, 49%).

LCMS: m/z 239 $[M+H]^+$.

Intermediate 12

4-{5-Amino-6-[(2,6-dichlorobenzyl)amino]pyrazin-2-yl}benzoic acid

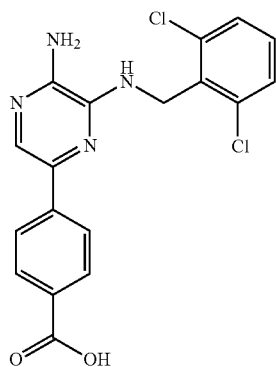 [SMILES: Nc1ncc(-c2ccc(C(=O)O)cc2)nc1NCc1c(Cl)cccc1Cl]

{5-Amino-6-[(2,6-dichlorobenzyl)amino]pyrazin-2-yl}benzoic acid was synthesised using the route shown in Scheme 6.

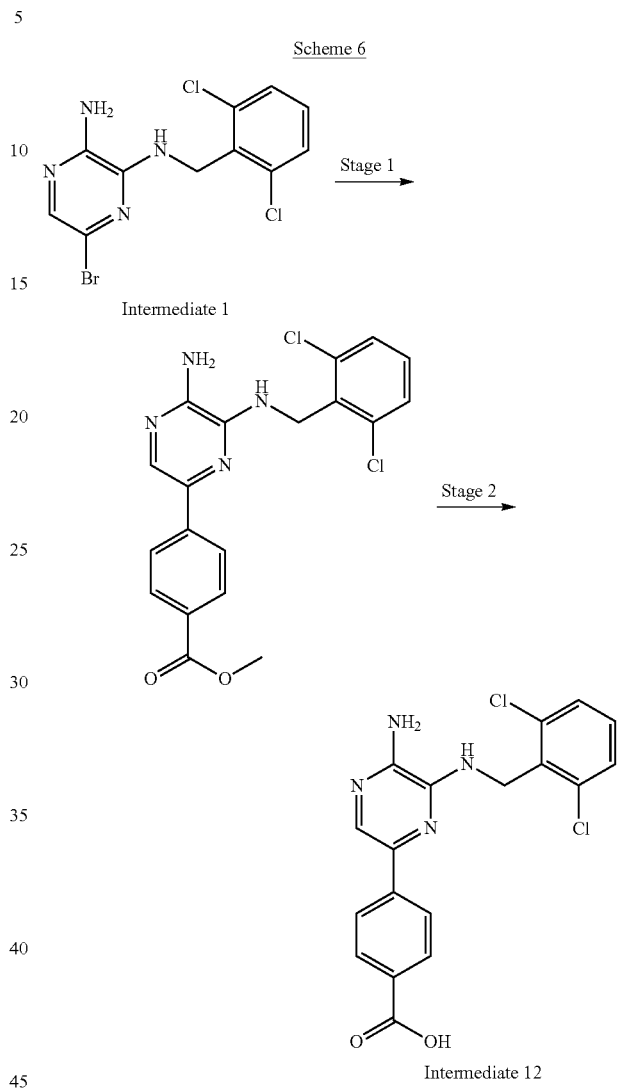

Scheme 6

Stage 1. Methyl 4-{5-amino-6-[(2,6-dichlorobenzyl)amino]pyrazin-2-yl}benzoate

To a solution of Intermediate 1 (3.82 g, 11.0 mmol) in DME (75 mL) was added methyl 4-(4,4,5,5-tetramethyl-1,3,2-dioxaborolan-2-yl)benzoate (4.48 g, 16.5 mmol) and 2N $Na_2CO_3$ (13.7 mL, 27.4 mmol) and the solution was degassed by bubbling nitrogen through the reaction mixture. Dichlorobis (triphenylphosphine) palladium (II) (385 mg, 0.5 mmol) was added and the reaction was stirred at 80° C. under a nitrogen atmosphere for 18 hrs. Another 0.05 eq of dichlorobis (triphenylphosphine) palladium (II) (385 mg, 0.5 mmol) was added and the reaction was stirred at 80° C. under a nitrogen atmosphere for 24 hrs for complete reaction. The reaction mixture was filtered through Celite® and the filter cake was washed with EtOAc (2×50 mL). The combined filtrates were washed with water (50 mL), brine (50 mL), dried over $MgSO_4$, filtered and concentrated in vacuo before purification by column chromatography (60% EtOAc/heptane) to give the title compound as a yellow/green solid (3.88 g, 88%).

LCMS: m/z 403/405 [M+H]+.

$^1$H NMR (300 MHz, CD$_3$OD) δ ppm: 8.09-8.02 (4H, m), 7.82 (1H, s), 7.47-7.44 (2H, m), 7.36-7.29 (1H, m), 5.00 (2H, s), 3.92 (3H, s).

Stage 2. 4-{5-Amino-6-[(2,6-dichlorobenzyl)amino]pyrazin-2-yl}benzoic acid

To a suspension of methyl 4-{5-amino-6-[(2,6-dichlorobenzyl)amino]pyrazin-2-yl}benzoate (2.31 g, 5.7 mmol) in a 1:1:1 mixture of THF, MeOH and water (30 mL) was added lithium hydroxide monohydrate (1.20 g, 28.6 mmol). The reaction was stirred at RT for 20 hrs for complete reaction. The solvent was removed under reduced pressure and the crude residue was partitioned between water (100 mL) and EtOAc (50 mL). The aqueous layer was separated and acidified to pH3 using 1N HCl. The resulting solid was collected by filtration, washed with water and dried in a vacuum oven at 40° C. to give the title compound as a yellow solid (1.43 g, 64%). LCMS: m/z 389/391 [M+H]+.

$^1$H NMR (300 MHz, DMSO-d$_6$) δ ppm: 12.81 (1H, br, s), 8.07-8.04 (2H, m), 7.95-7.93 (3H, m), 7.56-7.54 (2H, m), 7.41 (1H, dd, J=7.2, 8.9 Hz), 6.44 (1H, t, J=4.1 Hz), 6.40 (2H, br s), 4.83 (2H, d, J=4.1 Hz).

Intermediate 13

4-{5-Amino-6-[(2,6-dichlorobenzyl)amino]pyrazin-2-yl}benzoic acid

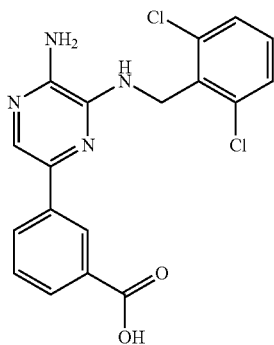 [SMILES: Nc1ncc(-c2cccc(C(=O)O)c2)nc1NCc1c(Cl)cccc1Cl]

3-{5-Amino-6-[(2,6-dichlorobenzyl)amino]pyrazin-2-yl}benzoic acid was synthesised in a similar manner to Intermediate 12 using the route shown in Scheme 6, reacting Intermediate 1 with 3-methoxycarbonylphenylboronic acid pinacol ester.

LCMS: m/z 389/391 [M+H]+.

$^1$H NMR (300 MHz, CD$_3$OD) δ ppm: 8.68-8.55 (1H, m), 8.12-8.05 (1H, m), 7.95-7.85 (1H, m), 7.78 (1H, m), 7.77-7.37 (3H, m), 7.35-7.29 (1H, m), 5.04 (2H, s).

Intermediate 14

4-{5-Amino-6-[(2,6-dichlorobenzyl)amino]pyrazin-2-yl}benzaldehyde

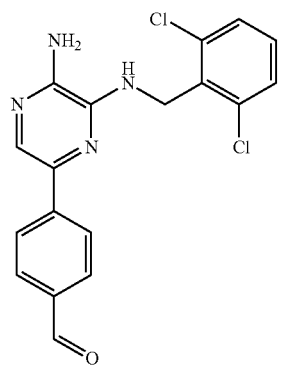 [SMILES: Nc1ncc(-c2ccc(C=O)cc2)nc1NCc1c(Cl)cccc1Cl]

4-{5-Amino-6-[(2,6-dichlorobenzyl)amino]pyrazin-2-yl}benzaldehyde was synthesised in a similar manner to Intermediate 12 using Stage 1 of the route shown in Scheme 6, reacting Intermediate 1 with Intermediate 6.

LCMS: m/z 373/375 [M+H]+.

$^1$H NMR (300 MHz, DMSO-d$_6$, δ ppm: 9.99 (1H, s), 8.17 (2H, d, J=8.4 Hz), 9.01 (1H, s), 7.91 (2H, d, J=8.4 Hz), 7.57-7.54 (2H, m), 7.42 (1H, dd, J=7.1, 8.6 Hz), 6.49 (3H, br, s), 4.85 (2H, d, J=4.1 Hz).

Intermediate 15

4-{5-Amino-6-[(2,6-difluorobenzyl)amino]pyrazin-2-yl}benzaldehyde

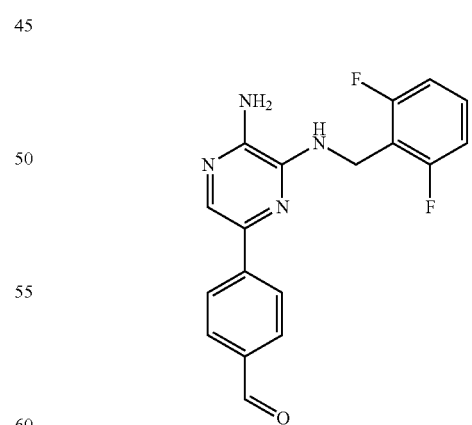

4-{5-Amino-6-[(2,6-difluorobenzyl)amino]pyrazin-2-yl}benzaldehyde was synthesised in a similar manner to Intermediate 12 according to Stage 1 of the route shown in Scheme 6, reacting Intermediate 2 with Intermediate 6.

LCMS: m/z 341 [M+H]+.

Intermediate 16

4-{5-Amino-6-[(2-chloro-6-fluorobenzyl)amino]pyrazin-2-yl}benzaldehyde

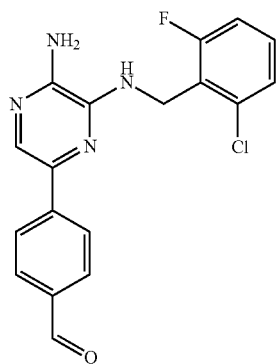 [SMILES: Nc1ncc(-c2ccc(C=O)cc2)nc1NCc1c(F)cccc1Cl]

4-{5-Amino-6-[(2-chloro-6-fluorobenzyl)amino]pyrazin-2-yl}benzaldehyde was synthesised in a similar manner to Intermediate 12 according to Stage 1 of the route shown in Scheme 6, reacting Intermediate 3 with Intermediate 6.

LCMS: m/z 357/359 [M+H]$^+$.

$^1$H NMR (300 MHz, CDCl$_3$) δ ppm: 10.08 (1H, s), 8.3-7.85 (5H, m), 4.95 (2H, d J=1.6 Hz), 4.90-4.7 (1H, m), 4.69-4.40 (2H, m).

Intermediate 17

4-{5-Amino-6-[(2,6-dichlorobenzyl)amino]pyrazin-2-yl}-2-chlorobenzaldehyde

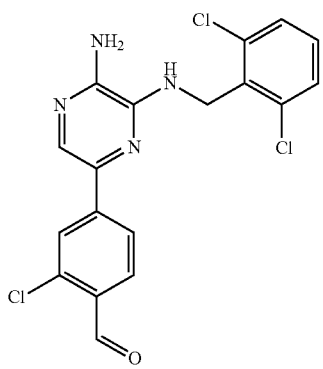 [SMILES: Nc1ncc(-c2ccc(C=O)c(Cl)c2)nc1NCc1c(Cl)cccc1Cl]

4-{5-Amino-6-[(2,6-dichlorobenzyl)amino]pyrazin-2-yl}-2-chlorobenzaldehyde was synthesised in a similar manner to Intermediate 12 according to Stage 1 of the route shown in Scheme 6, reacting Intermediate 1 and 3-chloro-4-formyl phenylboronic acid.

LCMS: m/z 407/409 [M+H]$^+$.

$^1$H NMR (300 MHz, CDCl$_3$) δ ppm: 10.51 (1H, s), 8.12-7.94 (2H, m), 7.9-7.8 (1H, m), 7.48-7.0 (4H, m), 5.03 (2H, d, J=1.6 Hz).

Intermediate 18

4-{5-Amino-6-[(2,6-dichlorobenzyl)amino]pyrazin-2-yl}-2-methylbenzaldehyde

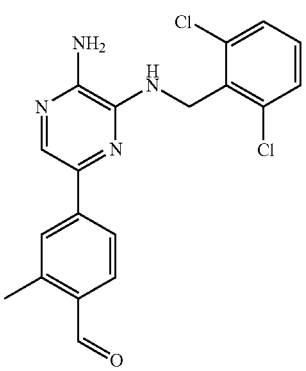 [SMILES: Cc1cc(-c2cnc(N)c(NCc3c(Cl)cccc3Cl)n2)ccc1C=O]

4-{5-Amino-6-[(2,6-dichlorobenzyl)amino]pyrazin-2-yl}-2-methylbenzaldehyde was synthesised in a similar manner to Intermediate 12 according to Stage 1 of the route shown in Scheme 6, reacting Intermediate 1 with Intermediate 9.

LCMS: m/z 387/389 [M+H]$^+$.

Intermediate 19

4-{5-Amino-6-[(2,6-dichlorobenzyl)amino]pyrazin-2-yl}-2-ethylbenzaldehyde

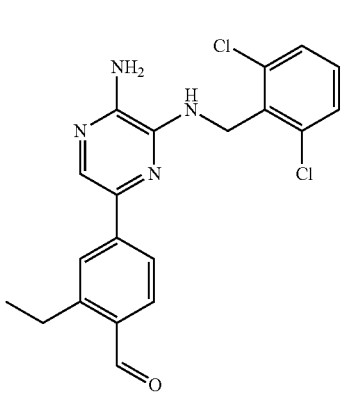 [SMILES: CCc1cc(-c2cnc(N)c(NCc3c(Cl)cccc3Cl)n2)ccc1C=O]

4-{5-Amino-6-[(2,6-dichlorobenzyl)amino]pyrazin-2-yl}-2-ethylbenzaldehyde was synthesised in a similar manner to Intermediate 12 according to Stage 1 of the route shown in Scheme 6, reacting Intermediate 1 with Intermediate 7.

LCMS: m/z 401/402 [M+H]$^+$.

Intermediate 20

3-{5-Amino-6-[(2,6-dichlorobenzyl)amino]pyrazin-2-yl}benzaldehyde

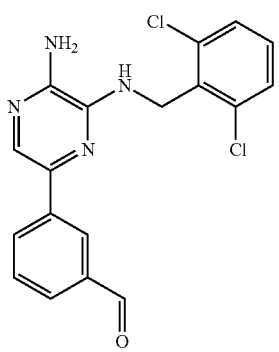 [SMILES: Nc1ncc(-c2cccc(C=O)c2)nc1NCc1c(Cl)cccc1Cl]

3-{5-amino-6-[(2,6-dichlorobenzyl)amino]pyrazin-2-yl}benzaldehyde was synthesised in a similar manner to Intermediate 12 using Stage 1 of the route shown in Scheme 6, reacting Intermediate 1 with Intermediate 5.

LCMS: m/z 373/375 [M+H]$^+$.

$^1$H NMR (300 MHz, CDCl$_3$) δ ppm: 10.13 (1H, s), 8.6-8.5 (1H, m), 8.33-8.2 (1H, m), 8.03 (1H, m), 7.95-7.85 (1H, m), 7.7-7.58 (1H, m), 7.49-73 (3H, m), 5.15-5.0 (2H, m), 4.6-4.4 (1H, m), 4.3-4.15 (2H, m).

Intermediate 21

Di-tert-butyl {3-[(tert-butoxycarbonyl)(2,6-dichlorobenzyl) amino]-5-[3-(2-oxoethyl)phenyl]pyrazin-2-yl}imidodicarbonate

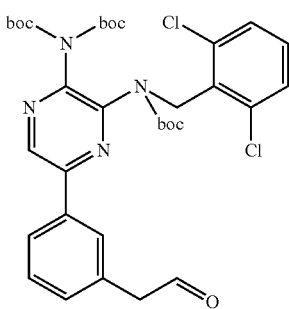

Di-tert-butyl {3-[(tert-butoxycarbonyl)(2,6-dichlorobenzyl)amino]-5-[3-(2-oxoethyl) phenyl]pyrazin-2-yl}imidodicarbonate was synthesised as shown in Scheme 7 below.

Scheme 7

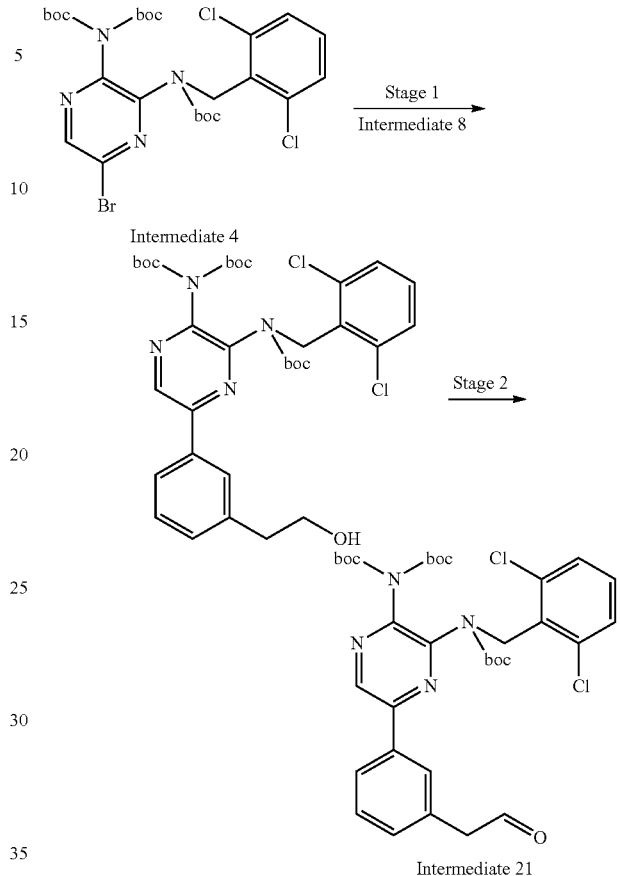

Stage 1: Di-tert-butyl {3-[(tert-butoxycarbonyl)(2,6-dichlorobenzyl)amino]-5-[3-(2-hydroxyethyl)phenyl]pyrazin-2-yl}imidodicarbonate To a solution of Intermediate 4 (175 mg, 0.27 mmol) in DME (2.6 mL), was added Intermediate 8 (100 mg, 0.40 mmol) and 2N Na$_2$CO$_3$ (0.34 mL, 0.67 mmol). The solution was degassed by bubbling nitrogen through the reaction mixture. Dichlorobis (triphenylphosphine) palladium (II) (19 mg, 0.02 mmol) was added and the reaction was stirred at 80° C. under nitrogen for 18 hrs for complete reaction. The reaction mixture was filtered through Celite® and the filter cake was washed with EtOAc (60 mL). The combined filtrates were washed with water (2×30 mL), brine (30 mL), dried over MgSO$_4$, filtered and concentrated in vacuo before purification by automated column chromatography using EtOAc in heptane (gradient 0-70%) to give the title compound as a white solid (192 mg, 103%).

LCMS: m/z 695/697/699 [M+Na]$^+$.

Stage 2: Di-tert-butyl {3-[(tert-butoxycarbonyl)(2,6-dichlorobenzyl)amino]-5-[3-(2-oxoethyl)phenyl]pyrazin-2-yl}imidodicarbonate Di-tert-butyl {3-[(tert-butoxycarbonyl)(2,6-dichlorobenzyl)amino]-5-[3-(2-hydroxyethyl) phenyl]pyrazin-2-yl}imidodicarbonate (169 mg, 0.25 mmol) was dissolved in anhydrous DCM (4 mL) and Dess-Martin periodinone (125 mg, 0.29 mmol) was added. The reaction mixture was stirred at RT under nitrogen for 1.5 hrs. The reaction was quenched with sat NaHCO$_3$ (2 mL) and sat sodium thiosulfate solution (2 mL) and vigorously stirred for 50 min. The aqueous was separated and washed with DCM (3×10 mL). The combined organics were dried over MgSO$_4$, filtered and concentrated in vacuo to give the title compound as a pale yellow oil (174 mg, >100%). The material was not purified further.

LCMS: m/z 709/711/713 [M+H]$^+$.

Intermediate 22

1-tert-Butyl 2-cyclopentyl (2R)-4-aminopiperidine-1,2-dicarboxylate

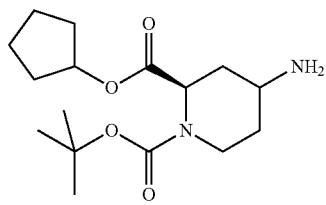 [SMILES: CC(C)(C)OC(=O)N1CCC(N)C[C@@H]1C(=O)OC1CCCC1]

1-tert-Butyl 2-cyclopentyl (2R)-4-aminopiperidine-1,2-dicarboxylate was synthesised by the route shown in Scheme 8.

Scheme 8

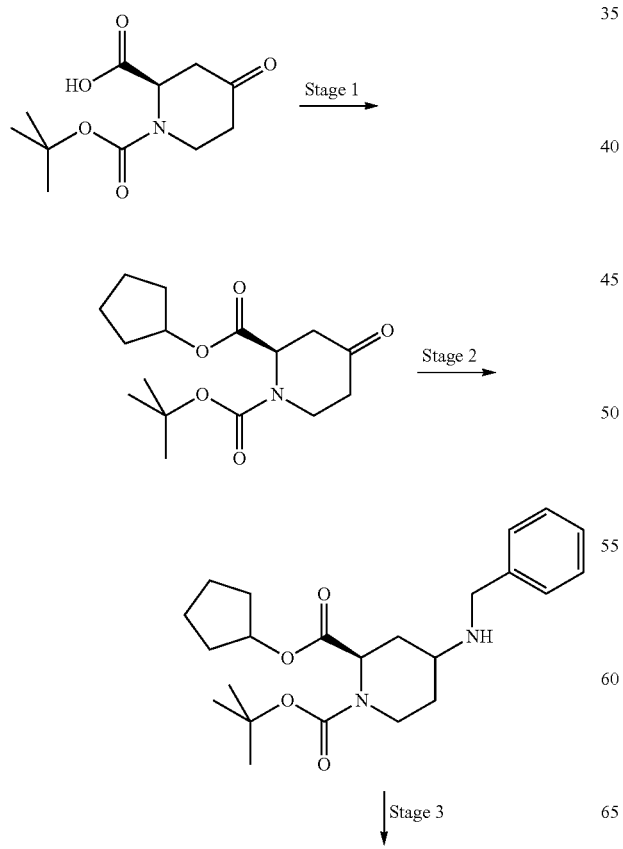

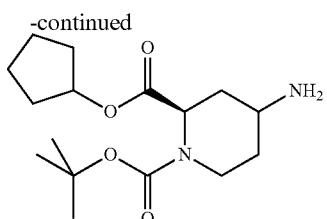

Intermediate 22

Stage 1. 1-tert-Butyl 2-cyclopentyl (2R)-4-oxopiperidine-1,2-dicarboxylate (2R)-1-(tert-Butoxycarbonyl)-4-oxopiperidine-2-carboxylic acid (6 g, 24.7 mmol) was dissolved in DCM (100 mL) and cooled to 0° C. Cyclopentanol (6.7 mL, 74 mmol), EDC (7.1 g, 37 mmol) and DMAP (0.30 g, 2.5 mmol) added. The reaction was allowed to warm to RT and stirred for 18 hrs. Saturated Na$_2$CO$_3$ was added and the organic layer separated. The aqueous layer was extracted with DCM (3×30 mL) and the combined organic layers were dried over Na$_2$SO$_4$. The solvent was removed in vacuo and the residue purified by automated column chromatography using EtOAc in DCM (gradient 0-30%) to give the title compound (3.83 g, 97%).

LCMS: m/z 334 [M+H]$^+$.

Stage 2. 1-tert-Butyl 2-cyclopentyl (2R)-4-(benzylamino)piperidine-1,2-dicarboxylate 1-tert-Butyl 2-cyclopentyl (2R)-4-oxopiperidine-1,2-dicarboxylate (3.82 g, 12.3 mmol) was dissolved in DCM (40 mL) and benzylamine (1.4 mL, 12.9 mmol) was added. To the reaction mixture was added acetic acid (0.84 mL, 14.7 mmol) and STAB (3.9 g, 18.4 mmol) and the reaction allowed to stir at RT for 1 hr. The mixture was diluted with DCM (20 mL) and sat NaHCO$_3$ (100 mL) was added. The aqueous layer was extracted with DCM (2×50 mL) and the combined organic layers were dried over MgSO$_4$, concentrated in vacuo and purified by automated column chromatography using EtOAc in DCM (gradient 0-35%) to give the title compound as a colourless oil (4.38 g, 84%).

LCMS: m/z 403.2 [M+H]$^+$.

Stage 3. 1-tert-Butyl 2-cyclopentyl (2R)-4-aminopiperidine-1,2-dicarboxylate 1-tert-Butyl 2-cyclopentyl (2R)-4-(benzylamino)piperidine-1,2-dicarboxylate (4.38 g, 10 mmol) was dissolved in methanol (40 mL) and charged with 10% Pd/C catalyst (1.4 g) under a nitrogen atmosphere. The reaction was stirred under a hydrogen balloon for 72 hrs for complete reaction. The solution was filtered through Celite® and the filtrates evaporated to dryness to give a colourless oil (3.7 g, 100%).

LCMS: m/z 313 [M+H]$^+$.

$^1$H NMR (300 MHz, CDCl$_3$) δ ppm: 8.58 (2H, br, s), 5.3-5.2 (1H, m), 4.65-4.52 (1H, m), 4.0-3.6 (2H, m), 3.42-3.15 (1H, m), 2.43-1.52 (12H, m), 1.46 (9H, s).

Intermediate 23

1-tert-Butyl 2-cyclopentyl (2S)-4-aminopiperidine-1,2-dicarboxylate

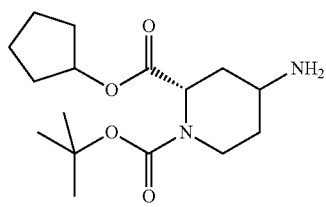 [SMILES: CC(C)(C)OC(=O)N1CCC(N)C[C@H]1C(=O)OC1CCCC1]

1-tert-Butyl 2-cyclopentyl (2S)-4-aminopiperidine-1,2-dicarboxylate was synthesised in a similar manner to Intermediate 22 using (2S)-1-(tert-Butoxycarbonyl)-4-oxopiperidine-2-carboxylic acid as the starting material in Scheme 8.
LCMS: m/z 313 [M+H]$^+$.

Intermediate 24

1-tert-Butyl 2-cyclopentyl (2R)-4-(methylamino)piperidine-1,2-dicarboxylate

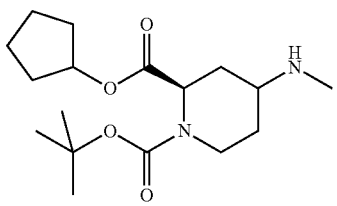 [SMILES: CNC1CCN(C(=O)OC(C)(C)C)[C@@H](C(=O)OC2CCCC2)C1]

1-tert-Butyl 2-cyclopentyl (2R)-4-(methylamino)piperidine-1,2-dicarboxylate was synthesised in a similar manner to Intermediate 22 using methylbenzylamine at Stage 2 of the route shown in Scheme 8.
LCMS: m/z 327 [M+H]$^+$.

Intermediate 25

Di-tert-butyl (2R)-4-aminopiperidine-1,2-dicarboxylate

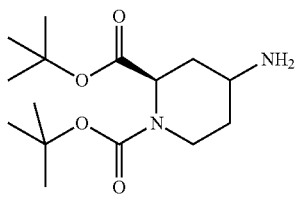 [SMILES: CC(C)(C)OC(=O)[C@H]1CC(N)CCN1C(=O)OC(C)(C)C]

Di-tert-butyl (2R)-4-aminopiperidine-1,2-dicarboxylate was synthesised in a similar manner to Intermediate 22 above starting with di-tert-butyl (2R)-4-oxopiperidine-1,2-dicarboxylate at Stage 2 of Scheme 8. The synthesis of di-tert-butyl (2R)-4-oxopiperidine-1,2-dicarboxylate is shown below in Scheme 9.

Scheme 9

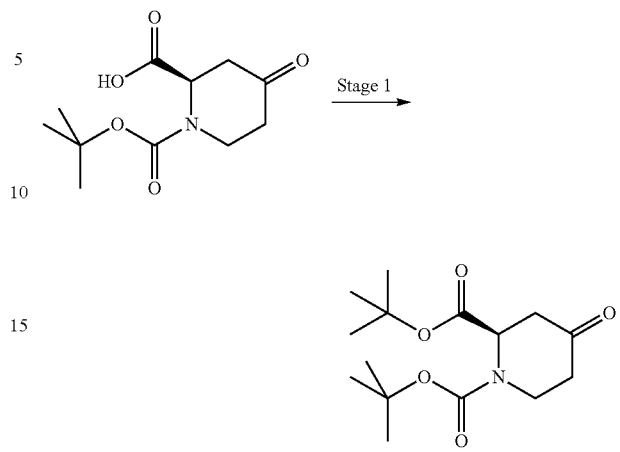

Stage 1. Di-tert-butyl (2R)-4-oxopiperidine-1,2-dicarboxylate (2R)-1-(tert-Butoxycarbonyl)-4-oxopiperidine-2-carboxylic acid (10 g, 41.1 mmol) was dissolved in anhydrous toluene (100 mL) and heated to 80° C. under nitrogen. N,N-dimethylformamide di-tert-butyl acetal (33.4 g, 164 mmol) was then added dropwise and the reaction allowed to stir at 80° C. for 2 hrs. The reaction mixture was then cooled to RT and EtOAc (150 mL) and water (150 mL) were added. The aqueous layer was extracted with EtOAc (2×150 mL) and the combined organic layers purified by flash column chromatography (20% EtOAc/heptane) to give the title compound (8.82 g, 72%).
LCMS: m/z 322 [M+Na]$^+$.

Intermediate 26

Di-tert-butyl (2S)-4-aminopiperidine-1,2-dicarboxylate

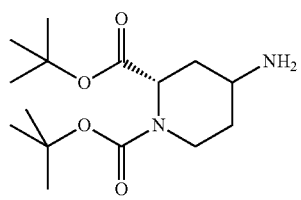 [SMILES: CC(C)(C)OC(=O)[C@@H]1CC(N)CCN1C(=O)OC(C)(C)C]

Di-tert-butyl (2S)-4-aminopiperidine-1,2-dicarboxylate was synthesised in a similar manner to Intermediate 22 above starting with di-tert-butyl (2S)-4-oxopiperidine-1,2-dicarboxylate at Stage 2 of Scheme 8. Di-tert-butyl (2S)-4-oxopiperidine-1,2-dicarboxylate was synthesised in a similar manner to di-tert-butyl (2R)-4-oxopiperidine-1,2-dicarboxylate shown in Scheme 9.
LCMS: m/z 322 [M+Na]$^+$.

Intermediate 27

Di-tert-butyl (2R)-4-(methylamino)piperidine-1,2-dicarboxylate

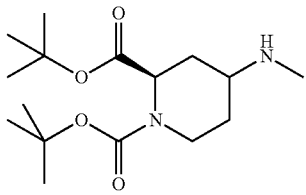 [SMILES: CNC1CCN(C(=O)OC(C)(C)C)[C@@H](C(=O)OC(C)(C)C)C1]

Di-tert-butyl (2R)-4-(methylamino)piperidine-1,2-dicarboxylate was synthesised in a similar manner to Intermediate 22 starting at Stage 2 of the route shown in Scheme 8 with di-tert-butyl (2R)-4-oxopiperidine-1,2-dicarboxylate and reacting with methylbenzylamine.

LCMS: m/z 315 [M+H]$^+$.

Intermediate 28

1-tert-Butyl 2-cyclopentyl piperazine-1,2-dicarboxylate

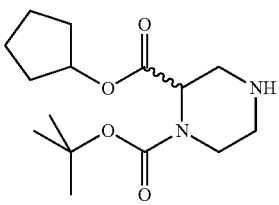 [SMILES: CC(C)(C)OC(=O)N1CCNCC1C(=O)OC1CCCC1]

1-tert-Butyl 2-cyclopentyl piperazine-1,2-dicarboxylate was synthesised using the route shown in Scheme 10.

Scheme 10

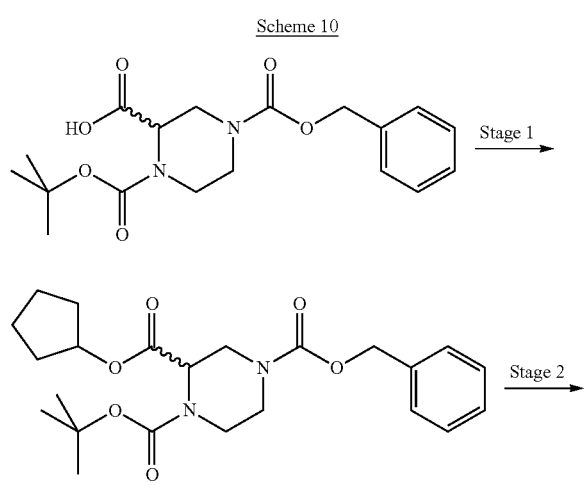

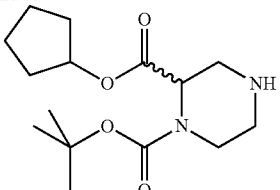

Intermediate 28

Stage 1: 4-Benzyl 1-tert-butyl 2-cyclopentyl piperazine-1,2,4-tricarboxylate 4-[(Benzyloxy)carbonyl]-1-(tert-butoxycarbonyl)piperazine-2-carboxylic acid (9.96 g, 27 mmol) was dissolved in DCM (50 mL) and cooled to 0° C. Cyclopentanol (7.4 mL, 82 mmol), EDC (7.86 g, 41 mmol) and DMAP (0.33 g, 2.7 mmol) were then added and the reaction allowed to warm to RT, and stirred for 24 hrs. Water (100 mL) and DCM (50 mL) were then added and the layers separated. The aqueous layer was re-extracted with DCM (2×50 mL) and the combined organic layers were then dried over MgSO$_4$ and concentrated in vacuo. Purification by column chromatography (40% EtOAc/heptane) afforded the title compound as a colourless oil (10.4 g, 88%). LCMS: m/z 455 [M+Na]$^+$.

Stage 2. 1-tert-Butyl 2-cyclopentyl piperazine-1,2-dicarboxylate

4-Benzyl 1-tert-butyl 2-cyclopentyl piperazine-1,2,4-tricarboxylate (10.4 g) was dissolved in EtOAc (100 mL), and stirred with 10% palladium on carbon (2 g, 20% w/w) under hydrogen at atmospheric pressure for 18 hrs. The reaction mixture was then filtered through Celite® and the solvent removed in vacuo to give the title compound as a white solid (6.62 g, 92%).

$^1$H NMR (300 MHz, CDCl$_3$) δ ppm: 5.27 (1H, m), 4.50 (1H, m), 3.81 (1H, m), 3.50 (1H, m), 2.82-3.2 (3H, m), 2.72 (1H, m), 1.55-1.95 (8H, br m), 1.45 (9H, s).

Intermediate 29

1-tert-Butyl 2-cyclopentyl (2S)-piperazine-1,2-dicarboxylate

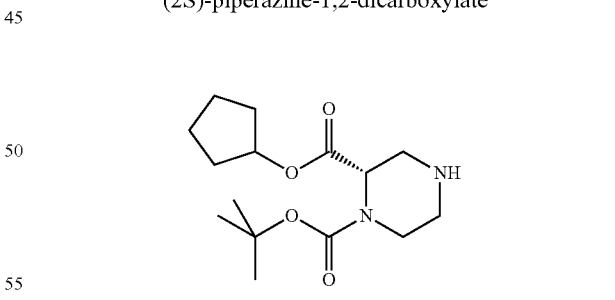

1-tert-Butyl 2-cyclopentyl (2S)-piperazine-1,2-dicarboxylate was synthesised in a similar manner to Intermediate 28 using (2S)-4-[(benzyloxy)carbonyl]-1-(tert-butoxycarbonyl)piperazine-2-carboxylic acid as the starting material in Scheme 10.

Stage 1. 4-Benzyl 1-tert-butyl 2-cyclopentyl (2S)-piperazine-1,2,4-tricarboxylate (2S)-4-[(Benzyloxy)carbonyl]-1-(tert-butoxycarbonyl) piperazine-2-carboxylic acid (0.5 g, 1.37 mmol) was dissolved in dimethylformamide (7 mL) and cooled to 0° C. Cyclopentanol (0.25 mL, 2.74 mmol), EDC (0.395 g, 2.06 mmol) and DMAP (0.017 g, 0.14 mmol) were added with stirring. The reaction was allowed to warm to room temperature and was stirred for 23 hrs. The reaction was quenched with water (40 mL) and the product extracted into EtOAc (3×20 mL). The combined organic layers were then washed with water (2×20 mL) and brine (20 mL), before being dried over MgSO$_4$. The solvent was removed in vacuo and the residue purified by automated column chromatography using EtOAc in heptane (gradient 0-60%) to give the title compound (0.345 g, 58%).

LCMS: m/z 455 [M+Na]$^+$.

Stage 2. 1-tert-Butyl 2-cyclopentyl (2S)-piperazine-1,2-dicarboxylate

4-Benzyl 1-tert-butyl 2-cyclopentyl (2S)-piperazine-1,2,4-tricarboxylate (0.35 g) was dissolved in EtOAc (5 mL) and stirred with 10% palladium on carbon (0.069 g, 20% w/w) under hydrogen at atmospheric pressure for 16.5 hrs. The reaction mixture was then filtered through Celite® and the solvent removed in vacuo to give the title compound (0.213 g, 90%).

LCMS: m/z 299 [M+H]$^+$.

$^1$H NMR (300 MHz; CD$_3$OD) δ ppm: 5.27 (1H, br, s), 4.44-4.66 (1H, m), 3.71-3.89 (1H, m), 3.49 (1H, t, J=13.0 Hz), 2.84-3.16 (3H, m), 2.63-2.76 (1H, m), 1.87 (2H, br. s), 1.58-1.78 (6H, m), 1.47 (12H, d, J=8.7 Hz).

Intermediate 30

1-tert-Butyl 2-cyclopentyl (2R)-piperazine-1,2-dicarboxylate

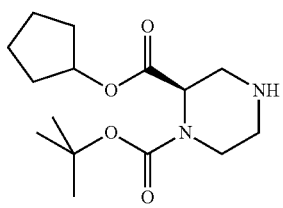 [SMILES: CC(C)(C)OC(=O)N1CCNC[C@@H]1C(=O)OC1CCCC1]

1-tert-Butyl 2-cyclopentyl (2R)-piperazine-1,2-dicarboxylate was synthesised in a similar manner to Intermediate 29 using (2R)-4-[(benzyloxy)carbonyl]-1-(tert-butoxycarbonyl)piperazine-2-carboxylic acid as the starting material in Scheme 10.

LCMS: m/z 299 [M+H]$^+$.

$^1$H NMR (300 MHz; CD$_3$OD) δ ppm: 5.27 (1H, br, s.), 4.41-4.67 (1H, m), 3.69-3.91 (1H, m), 3.49 (1H, t, J=12.6 Hz), 2.83-3.17 (3H, m), 2.63-2.77 (1H, m), 1.81-1.97 (2H, m), 1.58-1.78 (6H, m), 1.47 (12H, d, J=8.3 Hz).

Intermediate 31

Di-tert-butyl piperazine-1,2-dicarboxylate

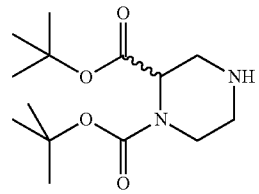 [SMILES: CC(C)(C)OC(=O)C1CNCCN1C(=O)OC(C)(C)C]

Di-tert-butyl piperazine-1,2-dicarboxylate was synthesised using the route shown in Scheme 11.

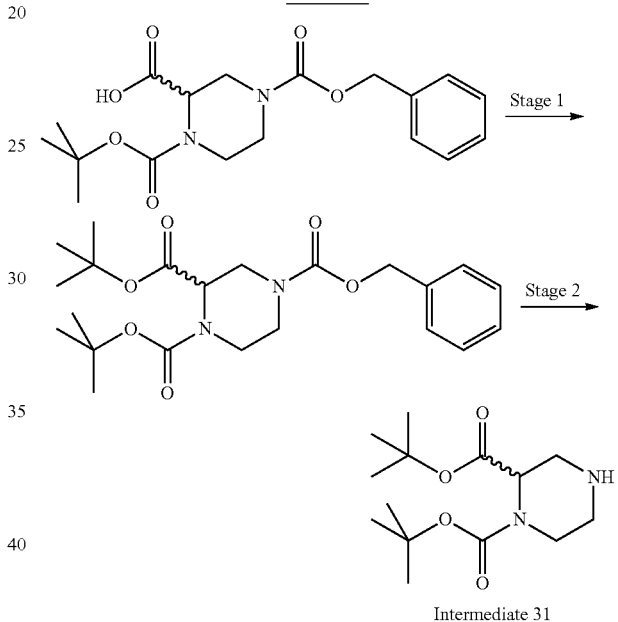

Intermediate 31

Stage 1. 4-Benzyl 1,2-di-tert-butyl piperazine-1,2,4-tricarboxylate

4-[(Benzyloxy)carbonyl]-1-(tert-butoxycarbonyl)piperazine-2-carboxylic acid (1.0 g, 2.74 mmol) was dissolved in toluene (10 mL) and heated to 80° C. under a nitrogen atmosphere. DMF di tert-butyl acetal was then added dropwise (2.6 mL, 11 mmol) and stirring continued for 2 hrs. The reaction mixture was cooled and partitioned between EtOAc (200 mL) and water (200 mL). The organic layer was separated and the aqueous layer re-extracted with EtOAc (2×100 mL). The combined organic layers were dried over MgSO$_4$, concentrated in vacuo and the residue was purified by automated column chromatography (0-100% EtOAc/heptane) to give the title compound as a colourless oil (1.08 g, 94%).

LCMS: m/z 443 [M+Na]$^+$.

Stage 2. Di-tert-butyl piperazine-1,2-dicarboxylate

4-Benzyl 1,2-di-tert-butyl piperazine-1,2,4-tricarboxylate (1.08 g) was dissolved in EtOAc (20 mL), and stirred with 10% palladium on carbon (0.22 g, 20% w/w) under hydrogen at atmospheric pressure for 17 hrs. The reaction mixture was then filtered through Celite® and the solvent removed in vacuo to give the title compound (0.810 g, >100%).

LCMS: m/z 287 [M+H]$^+$.

$^1$H NMR (300 MHz; CD$_3$OD) δ ppm: 3.72-3.96 (1H, m), 3.46-3.66 (1H, m), 2.98-3.22 (2H, m), 2.91 (1H, dd, J=12.7, 4.4 Hz), 2.55-2.83 (3H, m), 1.40-1.55 (18H, m).

Intermediate 32

Cyclopentyl L-leucinate

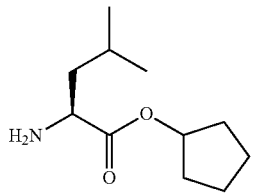

Cyclopentyl L-leucinate was prepared using the methodology described below:

To a slurry of L-leucine (5 g, 30.5 mmol) in cyclohexane (150 mL) were added cyclopentanol (27.5 mL, 305 mmol) and p-toluene sulfonic acid (6.33 g, 33.3 mmol). The reaction was fitted with a Dean-Stark receiver and heated to 135° C. for complete dissolution. This temperature was maintained for a period of 12 hrs after which time the reaction was complete. The reaction was cooled to RT with precipitation of a white solid. The solid was collected by filtered and washed with EtOAc before drying under reduced pressure. The required product was isolated as the tosylate salt (10.88 g, 85%).

LCMS: m/z 200 [M+H]$^+$.

$^1$H NMR (300 MHz, CD$_3$OD) δ ppm: 1.01 (6H, t, J=5.8 Hz), 1.54-2.03 (11H, m), 2.39 (3H, s), 3.96 (1H, t, J=6.5 Hz), 5.26-5.36 (1H, m), 7.25 (2H, d, J=7.9 Hz), 7.72 (2H, d, J=8.3 Hz).

Intermediate 33

Cyclopentyl 2-methylalaninate

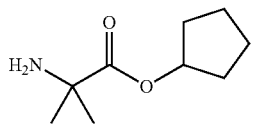

Cyclopentyl 2-methylaninate was prepared using the methodology described below:

To a flask containing of 2-amino-2-methylpropionic acid (50 g, 0.48 mol) in cyclohexane (125 mL), cyclopentanol (267 mL, 2.91 mol) and p-toluene sulfonic acid (101.5 g, 0.53 mol) was fitted with a Dean-Stark receiver and the reaction was heated to 135° C. for 18 hrs. A further portion of p-toluene sulfonic acid (34 g, 0.18 mol) was added and heated at reflux for 2 hrs after which time the reaction was complete. The reaction was poured onto ice-cold TBME (1 L) and the resulting solid was collected by filtration. The solid was vigorously stirred in diethyl ether (2 L), filtered and dried in a vacuum oven to give the required product as the tosylate salt (161 g, 97%).

$^1$H NMR (300 MHz, DMSO-d$_6$) δ ppm: 8.36 (3H, s), 7.48 (2H, d, J=8.1 Hz), 7.12 (2H, d, J=8.1 Hz), 5.18 (1H, t, J=5.7 Hz), 2.29 (3H, s), 1.90-1.80 (2H, m), 1.75-1.55 (6H, m), 1.43 (6H, s).

Intermediate 34

Cyclopentyl 1-aminocyclobutanecarboxylate

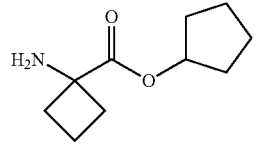 [SMILES: NC1(C(=O)OC2CCCC2)CCC1]

Cyclopentyl 1-aminocyclobutanecarboxylate was synthesised by the route shown in Scheme 12.

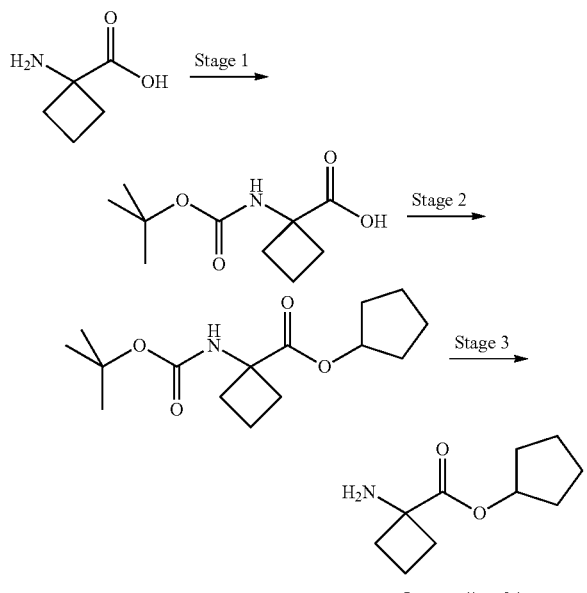

Intermediate 34

Stage 1. 1-[(tert-Butoxycarbonyl)amino]cyclobutanecarboxylic acid

To a solution of 1-amino-1-cyclobutane carboxylic acid (2.92 g, 25.4 mmol), NaOH (3.04 g, 76.2 mmol), THF (100 mL) and water (100 mL) at RT was added di-tert-butyl dicarbonate (8.30 g, 38.1 mmol) and the reaction was stirred for 24 hrs. The reaction mixture was acidified to pH5 using 2M HCl and the mixture was extracted with EtOAc (2×200 mL). The combined organics were dried over MgSO$_4$, filtered and concentrated in vacuo to give the title compound as a white solid (1.05 g, 19%). LCMS: m/z 238 [M+H]$^+$.

Stage 2. Cyclopentyl 1-[(tert-butoxycarbonyl)amino]cyclobutanecarboxylate

To a solution of 1-[(tert-butoxycarbonyl)amino]cyclobutanecarboxylic acid (5.2 g, 24.2 mmol), cyclopentanol (7.9 mL, 96.7 mmol) and DMAP (2.95 g, 24.2 mmol) in DCM (100 mL) was added EDC portion-wise (5.54 g, 29.0 mmol) and the reaction was stirred at RT for 3 hrs. The reaction was diluted with DCM (200 mL) and the mixture washed with 0.5 M HCl (2×150 mL), sat NaHCO₃ (2×150 mL) and brine (100 mL). The organic layer was separated, dried over MgSO₄, filtered, concentrated in vacuo and purified by automated column chromatography using EtOAc in heptane (gradient 0-50%) to give the title compound as a white solid (4.04 g, 59%).

LCMS: m/z 589 [M+Na]$^+$.

Stage 3. Cyclopentyl 1-aminocyclobutanecarboxylate

Cyclopentyl 1-[(tert-butoxycarbonyl)amino]cyclobutanecarboxylate (1.03 g, 3.63 mmol) was dissolved in 2N HCl in ether (25 mL) and stirred at RT for 24 hrs. Further 2N HCl in ether (6 mL) was added and the reaction was stirred for another 24 hrs. The solvent was concentrated in vacuo to give the title compound as a white solid (739 mg, 92%).

LCMS: m/z 184.2 [M+H]$^+$.

Intermediate 35

Cyclopentyl O-tert-butyl-L-serinate

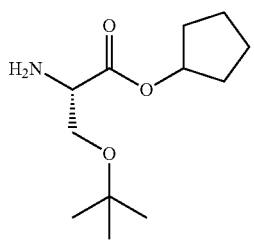 [SMILES: CC(C)(C)OC[C@H](N)C(=O)OC1CCCC1]

Cyclopentyl O-tert-butyl-L-serinate was synthesised by the route shown in Scheme 13.

Scheme 13

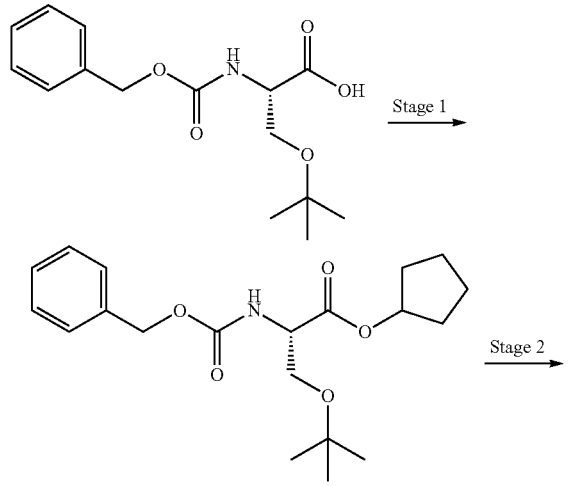

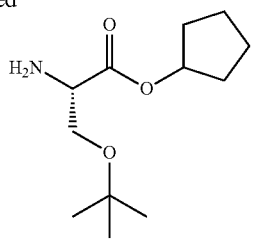

Intermediate 35

Stage 1. Cyclopentyl N-[(benzyloxy)carbonyl]-O-tert-butyl-L-serinate

N-[(Benzyloxy)carbonyl]-O-tert-butyl-L-serine (37.4 g, 0.13 mol), cyclopentanol (45.9 mL, 0.50 mol), EDC (29.1 g, 0.15 mol) and DMAP (370 mg, 3.0 mmol) were stirred in DCM (370 mL) at RT for 18 hrs. Further cyclopentanol (23 mL, 0.25 mol) and DMAP (1.0 g, 8.2 mmol) were added and the reaction was stirred at RT for 6 hrs, then 30° C. for 16 hrs. Water (500 mL) was added and the organic layer was separated and concentrated in vacuo. The resulting residue was purified by dry flash chromatography to give the title compound (32.4 g, 69%).

$^1$H NMR (300 Hz, CDCl₃) δ ppm: 7.30-7.46 (5H, m), 5.63 (1H, d, J=8.7 Hz), 5.19-5.30 (1H, m), 5.15 (2H, s), 4.42 (1H, dt, J=9.0, 3.2 Hz), 3.82 (1H, dd, J=8.7, 2.8 Hz), 3.57 (1H, dd, J=8.7, 2.8 Hz), 1.51-1.96 (8H, m), 1.14 (9H, s).

Stage 2. Cyclopentyl O-tert-butyl-L-serinate

To solution of cyclopentyl N-[(benzyloxy)carbonyl]-O-tert-butyl-L-serinate (32.4 g, 94.4 mmol) in EtOAc (350 mL) was added 10% palladium on carbon catalyst (1.7 g, 5% w/w) under nitrogen. The reaction was stirred at RT for 16 hrs under a hydrogen atmosphere. The reaction was filtered through Celite® and the filter cake was washed with EtOAc. The solvent was concentrated in vacuo to give the title compound (22.3 g, >100%).

$^1$H NMR (300 Hz, CDCl₃) δ ppm: 5.15 (1H, m), 3.37-3.60 (3H, m), 1.41-1.89 (10H, m), 1.09 (9H, s).

EXAMPLES

Example 1

Cyclopentyl (2R)-4-[(4-{5-amino-6-[(2,6-dichlorobenzyl)amino]pyrazin-2-yl}benzoyl)amino]piperidine-2-carboxylate

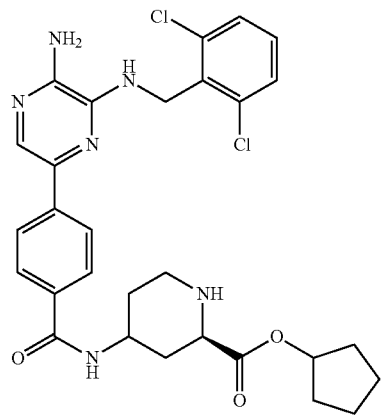 [SMILES: Nc1ncc(-c2ccc(C(=O)NC3CCN[C@@H](C(=O)OC4CCCC4)C3)cc2)nc1NCc1c(Cl)cccc1Cl]

Cyclopentyl (2R)-4-[(4-{5-amino-6-[(2,6-dichlorobenzyl)amino]pyrazin-2-yl}benzoyl) amino]piperidine-2-carboxylate was synthesised using the route shown in Scheme 14.

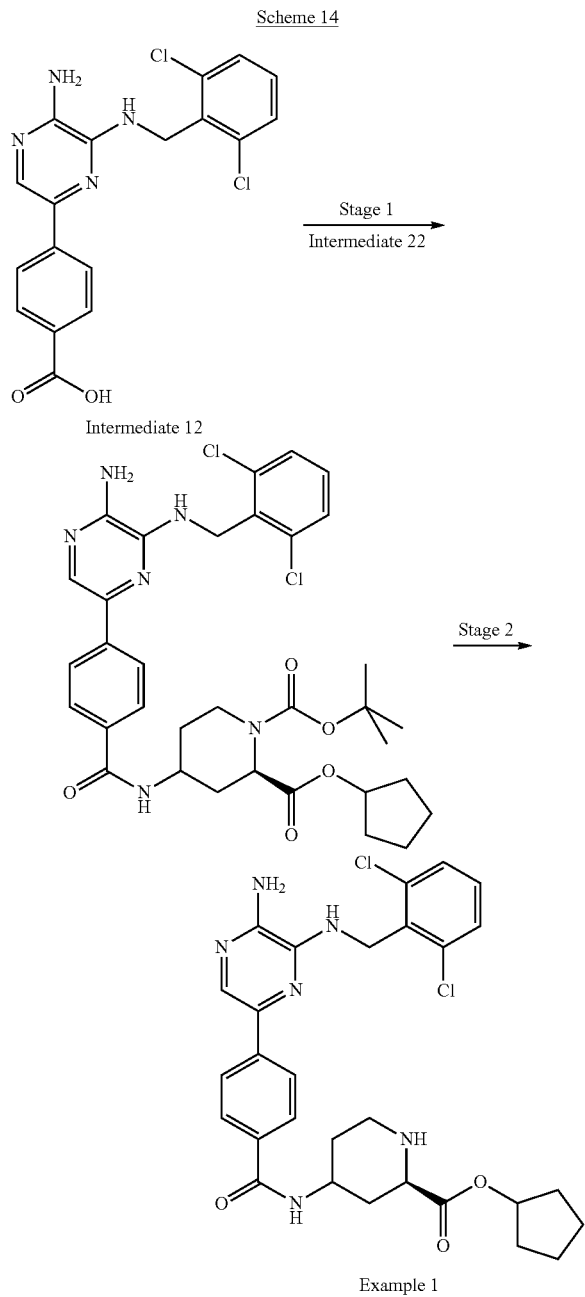

Scheme 14

Intermediate 12 → Stage 1 (Intermediate 22) → [Boc-protected intermediate] → Stage 2 → Example 1

Stage 1. 1-tert-Butyl 2-cyclopentyl (2R)-4-[(4-{5-amino-6-[(2,6-dichlorobenzyl)amino]pyrazin-2-yl}benzoyl)amino]piperidine-1,2-dicarboxylate Intermediate 12 (100 mg, 0.26 mmol) was dissolved in DMF (5 mL) and EDC (59 mg, 0.31 mmol) and HOBt (42 mg, 0.31 mmol) were added. The reaction was stirred for 20 mins after which time Intermediate 22 (96 mg, 0.31 mmol) was added. The reaction was allowed to stir for 18 hours at RT. The reaction mixture was diluted with EtOAc (50 mL) and washed with 2N NaOH (20 mL), water (2×20 mL), brine (20 mL), dried over MgSO$_4$, filtered and concentrated in vacuo. The crude material was purified by column chromatography (80% EtOAc/heptane) to give the title compound as a yellow solid (95 mg, 54%).

LCMS: m/z 683/685 [M+H]$^+$.

Stage 2. Cyclopentyl (2R)-4-[(4-{5-amino-6-[(2,6-dichlorobenzyl)amino]pyrazin-2-yl}benzoyl)amino] piperidine-2-carboxylate 1-tert-Butyl 2-cyclopentyl (2R)-4-[(4-{5-amino-6-[(2,6-dichlorobenzyl)amino]pyrazin-2-yl}benzoyl)amino]piperidine-1,2-dicarboxylate (95 mg, 0.14 mmol) was dissolved in DCM (20 mL) and 2M HCl in diethyl ether (2 mL) was added. The resulting suspension was stirred at RT for 18 hours. The solvent was removed in vacuo and the crude was dissolved in Na$_2$CO$_3$ (20 mL) and the product was extracted with EtOAc (3×20 mL). The combined organic layers were washed with brine (20 mL), dried over MgSO$_4$, filtered and concentrated in vacuo in give a yellow oil which was dissolved in 1:4 MeCN/water (10 mL) and freeze-dried to give the title compound as a yellow solid (63 mg, 78%).

LCMS: purity 95%, m/z 583/585 [M+H]$^+$.

$^1$H NMR (300 MHz, CD$_3$OD) δ ppm: 8.06 (2H, d, J=8.5 Hz), 7.88 (2H, d, J=8.5 Hz), 7.81 (1H, s), 7.42 (2H, d, J=7.7 Hz), 7.35-7.29 (1H, m), 5.26-5.21 (1H, m), 4.15-4.04 (1H, m), 3.50-3.45 (1H, m), 3.24-3.18 (1H, m), 2.76 (1H, td, J=2.5, 12.6 Hz), 2.34 (1H, d, J=12.2 Hz), 1.98-1.41 (11H, m).

Example 2

Cyclopentyl (2R)-4-[(4-{5-amino-6-[(2,6-dichlorobenzyl)amino]pyrazin-2-yl}benzoyl)amino]piperidine-2-carboxylate

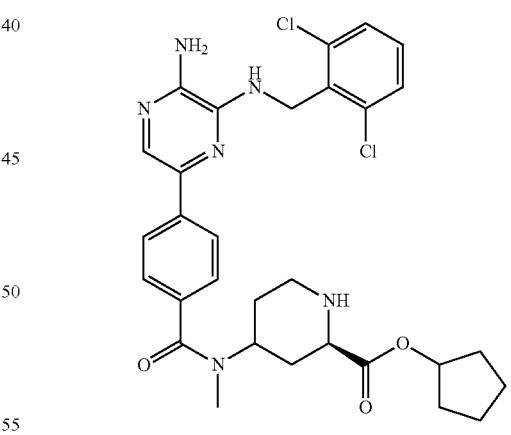

Cyclopentyl (2R)-4-[(4-{5-amino-6-[(2,6-dichlorobenzyl)amino]pyrazin-2-yl}benzoyl) amino]piperidine-2-carboxylate was synthesised in a similar manner to Example 1 using Intermediate 24 at Stage 1 in the route shown in Scheme 14.

LCMS: purity 100%, m/z 597/599 [M+H]$^+$.

$^1$H NMR (300 MHz, CDCl$_3$) δ ppm: 8.04 (2H, d, J=8.1 Hz), 7.92 (1H, s), 7.46 (2H, d, J=8.1 Hz), 7.39-7.36 (2H, m), 7.25-7.19 (2H, m), 5.23 (1H, br s), 5.05 (2H, d, J=5.5 Hz), 4.51 (1H, t, J=5.4 Hz), 4.33 (2H, br s), 3.28 (1H, br s), 2.90 (4H, br s), 1.90-1.60 (11H, m).

Example 3

Cyclopentyl 4-(4-{5-amino-6-[(2,6-dichlorobenzyl)amino]pyrazin-2-yl}benzoyl)piperazine-2-carboxylate

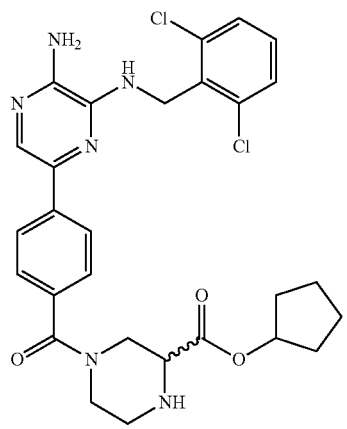 [SMILES: Nc1ncc(-c2ccc(C(=O)N3CCNC(C(=O)OC4CCCC4)C3)cc2)nc1NCc1c(Cl)cccc1Cl]

Cyclopentyl 4-(4-{5-amino-6-[(2,6-dichlorobenzyl)amino]pyrazin-2-yl}benzoyl) piperazine-2-carboxylate was synthesised in a similar manner to Example 1 using Intermediate 28 at Stage 1 in the route shown in Scheme 14 with purification by preparative HPLC.

LCMS: purity 100%, m/z 569/571 [M+H]$^+$.

$^1$H NMR (300 MHz, CDCl$_3$) δ ppm: 8.03 (2H, d, J=8.2 Hz), 7.92 (1H, s), 7.48 (2H, d, J=8.2 Hz), 7.38-7.35 (2H, m), 7.22 (1H, dd, J=7.4, 8.7 Hz), 5.24 (1H, br s), 5.04 (2H, d, J=5.5 Hz), 4.68 (1H, br, s), 4.56 (2H, br s), 3.53-3.31 (3H, m), 3.14-3.10 (1H, m), 2.84 (1H, br s), 2.18-1.58 (10H, m).

Example 4 tert-Butyl (2R)-4-[(4-{5-amino-6-[(2,6-dichlorobenzyl)amino]pyrazin-2-yl}benzoyl)amino]piperidine-2-carboxylate

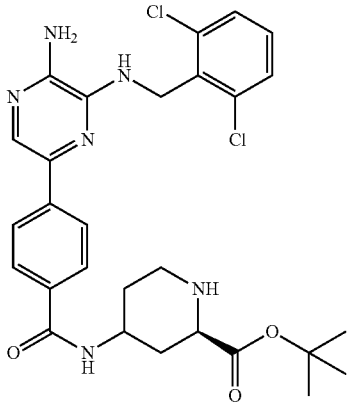 [SMILES: CC(C)(C)OC(=O)[C@H]1CC(NC(=O)c2ccc(-c3cnc(N)c(NCc4c(Cl)cccc4Cl)n3)cc2)CCN1]

tert-Butyl (2R)-4-[(4-{5-amino-6-[(2,6-dichlorobenzyl)amino]pyrazin-2-yl}benzoyl) amino]piperidine-2-carboxylate was synthesised by the route shown in Scheme 15.

Scheme 15

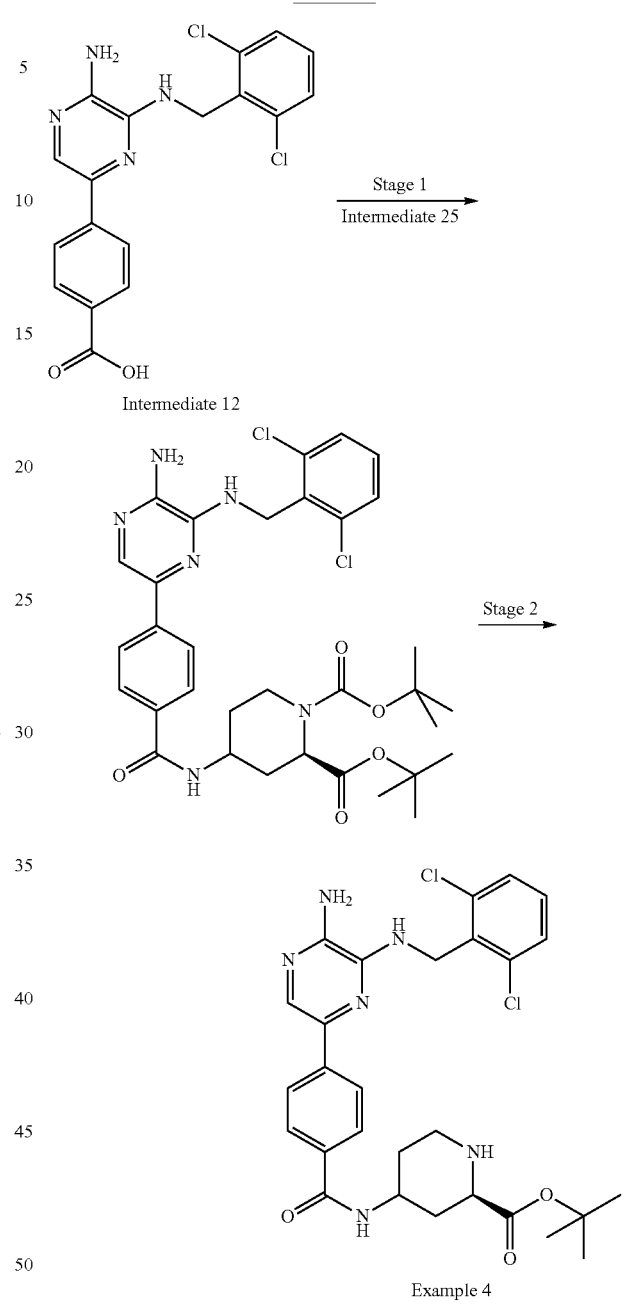

Stage 1. Di-tert-butyl (2R)-4-[(4-{5-amino-6-[(2,6-dichlorobenzyl)amino]pyrazin-2-yl}benzoyl)amino]piperidine-1,2-dicarboxylate Intermediate 12 (100 mg, 0.26 mmol) was dissolved in DMF (5 mL) and EDC (59 mg, 0.31 mmol) and HOBt (42 mg, 0.31 mmol) were added. The reaction was stirred for 20 mins after which time Intermediate 25 (96 mg, 0.31 mmol) was added. The reaction was allowed to stir for 18 hours at RT. The reaction mixture was diluted with EtOAc (50 mL) and washed with 2N NaOH (20 mL), water (2×20 mL), brine (20 mL), dried over MgSO$_4$, filtered and concentrated in vacuo. The crude material was purified by column chromatography (80% EtOAc/heptane) to give the title compound as a yellow oil (153 mg, 89%).

LCMS: m/z 671/673 [M+H]+.

Stage 2. tert-Butyl (2R)-4-[(4-{5-amino-6-[(2,6-dichlorobenzyl)amino]pyrazin-2-yl}benzoyl)amino]piperidine-2-carboxylate Di-tert-butyl (2R)-4-[(4-{5-amino-6-[(2,6-dichlorobenzyl)amino]pyrazin-2-yl}benzoyl) amino]piperidine-1,2-dicarboxylate (153 mg, 0.23 mmol) was dissolved in dioxane (5 mL) and cooled to 0° C. before the addition of 4M HCl in dioxane (20 mL). The reaction was stirred at 0° C. for 2 hrs. The reaction was basified to pH12 using 2N NaOH and extracted with EtOAc (3×20 mL). The combined organic layers were washed with brine (20 mL), dried over MgSO4, filtered and concentrated in vacuo to give a yellow solid which was purified by preparative HPLC to give the title compound as an off-white solid (50 mg, 38%).

LCMS: purity 98%, m/z 571/573 [M+H]+.

1H NMR (300 MHz, CDCl3) δ ppm: 8.06 (2H, d, J=8.5 Hz), 7.97 (1H, s), 7.82 (2H, d, J=8.5 Hz), 7.36-7.33 (2H, m), 7.19 (1H, dd, J=7.4, 8.6 Hz), 6.13 (1H, d, J=8.1 Hz), 5.05 (2H, d, J=5.5 Hz), 4.61 (1H, t, J=5.5 Hz), 4.41 (2H, br s), 4.23-4.11 (1H, m), 3.39 (1H, dd, J=2.7, 11.0 Hz), 3.26-3.19 (1H, m), 2.83-2.74 (1H, m), 2.44 (1H, d, J=12.4 Hz), 2.07-2.01 (1H, m), 1.47 (9H, s), 1.45-1.36 (2H, m).

Example 5 tert-Butyl (2R)-4-[(4-{5-amino-6-[(2,6-dichlorobenzyl)amino]pyrazin-2-yl}benzoyl)(methyl)amino]piperidine-2-carboxylate

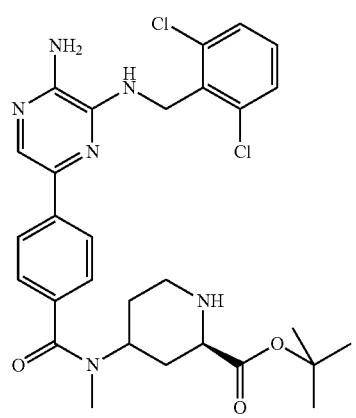 [SMILES: CN(C(=O)c1ccc(-c2cnc(N)c(NCc3c(Cl)cccc3Cl)n2)cc1)C1CCN[C@@H](C(=O)OC(C)(C)C)C1]

tert-Butyl (2R)-4-[(4-{5-amino-6-[(2,6-dichlorobenzyl)amino]pyrazin-2-yl}benzoyl) (methyl)amino]piperidine-2-carboxylate was synthesised in a similar manner to Example 4 using Intermediate 27 at Stage 1 in the route shown in Scheme 15.

LCMS: purity 96%, m/z 585/587 [M+H]+.

1H NMR (300 MHz, CDCl3) δ ppm: 8.04 (2H, d, J=8.3 Hz), 7.96 (1H, s), 7.46 (2H, d, J=7.9 Hz), 7.38-7.36 (2H, m), 7.22 (1H, dd, J=7.4, 8.7 Hz), 5.05 (2H, d, J=5.5 Hz), 4.58 (1H, t, J=5.5 Hz), 4.38 (2H, br s), 3.26 (2H, br s), 2.99-2.91 (4H, m), 2.19-1.98 (1H, m), 1.76 (2H, under H2O peak), 1.49 (9H, s).

Example 6 tert-Butyl 4-(4-{5-amino-6-[(2,6-dichlorobenzyl)amino]pyrazin-2-yl}benzoyl)piperazine-2-carboxylate

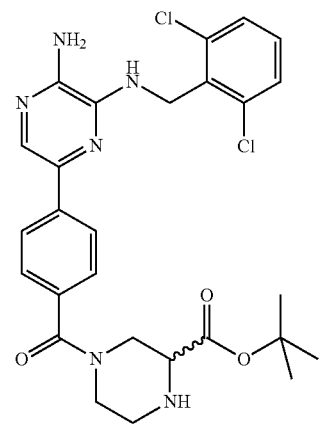 [SMILES: CC(C)(C)OC(=O)C1CN(C(=O)c2ccc(-c3cnc(N)c(NCc4c(Cl)cccc4Cl)n3)cc2)CCN1]

tert-Butyl 4-(4-{5-amino-6-[(2,6-dichlorobenzyl)amino]pyrazin-2-yl}benzoyl) piperazine-2-carboxylate was synthesised in a similar manner to Example 4 using Intermediate 31 at Stage 1 in the route shown in Scheme 15.

LCMS: purity 98%, m/z 557/559 [M+H]+.

1H NMR (300 MHz, CDCl3) δ ppm: 8.03 (2H, d, J=8.2 Hz), 7.94 (1H, s), 7.48 (2H, d, J=8.2 Hz), 7.36-7.34 (2H, m), 7.20 (1H, dd, J=7.4, 8.9 Hz), 5.03 (2H, d, J=5.3 Hz), 4.61 (1H, t, J=5.3 Hz), 4.43 (2H, br s), 3.44-3.37 (2H, m), 3.33-3.26 (1H, m), 3.12-3.08 (1H, m), 2.81 (1H, br s), 2.12 (2H, br s), 1.47 (9H, s).

Example 7

Cyclopentyl (2R)-4-[(4-{5-amino-6-[(2,6-dichlorobenzyl)amino]pyrazin-2-yl}benzyl)amino]piperidine-2-carboxylate

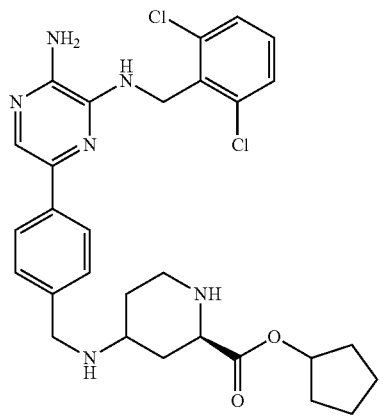

Cyclopentyl (2R)-4-[(4-{5-amino-6-[(2,6-dichlorobenzyl)amino]pyrazin-2-yl}benzyl) amino]piperidine-2-carboxylate was synthesised using the route shown in Scheme 16.

Scheme 16

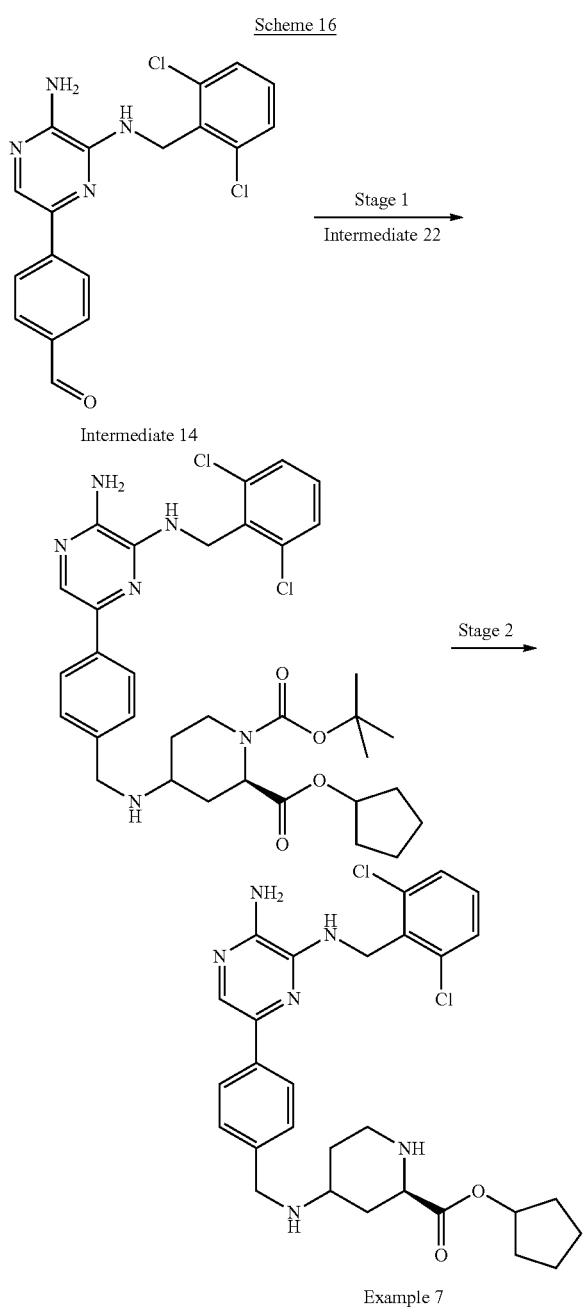

Intermediate 14

Example 7

Stage 1: 1-tert-Butyl 2-cyclopentyl (2R)-4-[(4-{5-amino-6-[(2,6-dichlorobenzyl)amino]pyrazin-2-yl}benzyl)amino]piperidine-1,2-dicarboxylate Intermediate 14 (150 mg, 0.40 mmol) and Intermediate 22 (138 mg, 0.44 mmol) were dissolved in DCE (15 mL) and stirred at RT for 2 hrs. STAB (170 mg, 0.80 mmol) was added and the reaction was stirred for a further 18 hrs. The reaction was quenched by the addition of sat Na₂CO₃ (20 mL) and vigorously stirred for 20 mins. The aqueous layer was separated and further extracted with DCM (2×20 mL) and the combined organics were dried over MgSO₄, filtered, concentrated in vacuo and purified by column chromatography (80% EtOAc/heptane) to give the title compound as an orange oil (168 mg, 62%).

LCMS: m/z 669/671 [M+H]⁺.

Stage 2: Cyclopentyl (2R)-4-[(4-{5-amino-6-[(2,6-dichlorobenzyl)amino]pyrazin-2-yl}benzyl)amino]piperidine-2-carboxylate 1-tert-Butyl 2-cyclopentyl (2R)-4-[(4-{5-amino-6-[(2,6-dichlorobenzyl)amino]pyrazin-2-yl}benzyl)amino]piperidine-1,2-dicarboxylate (168 mg, 0.25 mmol) was dissolved in DCM (20 mL) and 2M HCl in diethyl ether (5 mL) was added. The mixture was stirred at RT for 18 hours. The solvent was removed in vacuo and the crude was dissolved in Na₂CO₃ (20 mL) and the product was extracted with EtOAc (3×20 mL). The combined organic layers were washed with brine (20 mL), dried over MgSO₄, filtered and concentrated in vacuo to give a yellow oil which was purified by preparative HPLC to afford the title compound as an off-white solid (83 mg, 60%).

LCMS: purity 100%, m/z 569/571 [M+H]⁺.

$^1$H NMR (300 MHz, CD$_3$OD) δ ppm: 7.95 (2H, d, J=8.1 Hz), 7.72 (1H, s), 7.48-7.41 (4H, m), 7.35-7.30 (1H, m), 5.23-5.18 (1H, m), 5.01 (2H, s), 3.91 (2H, br s), 3.18-3.14 (1H, m), 2.81 (1H, br s), 2.67-2.59 (1H, m), 2.31 (1H, d, J=12.2 Hz), 2.00 (1H, d, J=12.8 Hz), 1.93-1.86 (2H, m), 1.85-1.60 (6H, m), 1.39-1.21 (2H, m), (1H missing. Under MeOH peak).

Example 8

Cyclopentyl (2S)-4-[(4-{5-amino-6-[(2,6-dichlorobenzyl)amino]pyrazin-2-yl}benzyl)amino]piperidine-2-carboxylate Cyclopentyl (2S)-4-[(4-{5-amino-6-[(2,6-dichlorobenzyl)amino]pyrazin-2-yl}benzyl) amino]piperidine-2-carboxylate was synthesised in a similar manner to Example 7 using Intermediate 23 at Stage 1 in the route shown in Scheme 16.

LCMS: purity 95%, m/z 569/571 [M+H]⁺.

$^1$H NMR (300 MHz, CDCl$_3$) δ ppm: 7.92 (2H, d, J=8.1 Hz), 7.91 (1H, s), 7.41-7.33 (4H, m), 7.19 (1H, dd, J=7.3, 8.7 Hz), 5.24-5.18 (1H, m), 5.04 (2H, d, J=5.5 Hz), 4.51 (1H, t, J=5.3 Hz), 4.35 (2H, br s), 3.90 (2H, s), 3.29 (1H, dd, J=2.8, 11.5 Hz), 3.24-3.18 (1H, m), 2.75-2.58 (2H, m), 2.29 (1H, d, J=13.2 Hz), 2.06-1.56 (9H, m), 1.33-1.20 (4H, m).

Example 9

Cyclopentyl 4-(4-{5-amino-6-[(2,6-dichlorobenzyl)amino]pyrazin-2-yl}benzyl)piperazine-2-carboxylate

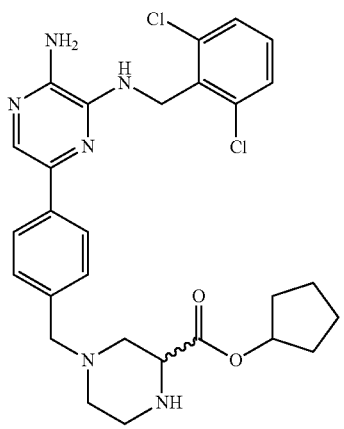 [SMILES: Nc1ncc(-c2ccc(CN3CCNC(C(=O)OC4CCCC4)C3)cc2)nc1NCc1c(Cl)cccc1Cl]

Cyclopentyl 4-(4-{5-amino-6-[(2,6-dichlorobenzyl)amino]pyrazin-2-yl}benzyl) piperazine-2-carboxylate was synthesised in a similar manner to Example 7 using Intermediate 28 at Stage 1 in the route shown in Scheme 16.

LCMS: purity 99%, m/z 555/557 [M+H]$^+$.

$^1$H NMR (300 MHz, CDCl$_3$) δ ppm: 7.96-7.91 (3H, m), 7.39-7.32 (4H, m), 7.17 (1H, dd, J=7.4, 8.6 Hz), 5.21 (1H, t, J=5.8 Hz), 5.03 (2H, d, J=5.3 Hz), 4.57 (1H, t, J=5.3 Hz), 4.37 (2H, br s), 3.64-3.47 (3H, m), 3.11-3.05 (1H, m), 2.92-2.80 (2H, m), 2.61-2.57 (1H, m), 2.46 (1H, t, J=8.9 Hz), 2.28 (1H, t, J=8.4 Hz), 2.04 (1H, br s), 1.90-1.81 (2H, m), 1.72-1.57 (6H, m).

Example 10

Cyclopentyl (2S)-4-(4-{5-amino-6-[(2,6-dichlorobenzyl)amino]pyrazin-2-yl}benzyl)piperazine-2-carboxylate

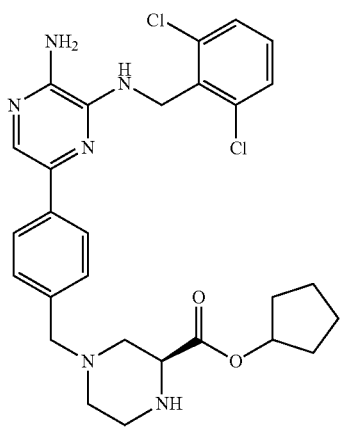 [SMILES: Nc1ncc(-c2ccc(CN3CCN[C@H](C(=O)OC4CCCC4)C3)cc2)nc1NCc1c(Cl)cccc1Cl]

Cyclopentyl (2S)-4-(4-{5-amino-6-[(2,6-dichlorobenzyl)amino]pyrazin-2-yl}benzyl) piperazine-2-carboxylate was synthesised in a similar manner to Example 7 using Intermediate 29 at Stage 1 in the route shown in Scheme 16.

LCMS: purity 98%, m/z 555/557/559 [M+H]$^+$.

$^1$H NMR (300 MHz, DMSO-d$_6$) δ ppm: 7.87 (2H, d, J=7.9 Hz), 7.79 (1H, s), 7.56 (1H, s), 7.53 (1H, s), 7.37-7.44 (1H, m), 7.28 (2H, d, J=8.1 Hz), 6.32 (1H, t, J=3.8 Hz), 6.18 (2H, s), 5.07 (1H, t, J=5.7 Hz), 4.82 (2H, d, J=3.8 Hz), 3.48-3.56 (1H, m), 3.36-3.42 (2H, m), 2.89-2.99 (1H, m), 2.53-2.69 (3H, m), 2.32-2.45 (2H, m), 2.19-2.30 (1H, m), 1.72-1.87 (2H, m), 1.44-1.63 (6H, m).

Example 11

Cyclopentyl (2R)-4-(4-{5-amino-6-[(2,6-dichlorobenzyl)amino]pyrazin-2-yl}benzyl)piperazine-2-carboxylate

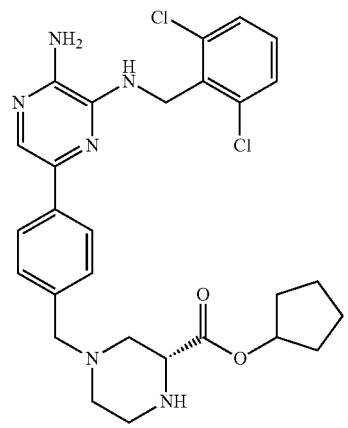 [SMILES: Nc1ncc(-c2ccc(CN3CCN[C@@H](C(=O)OC4CCCC4)C3)cc2)nc1NCc1c(Cl)cccc1Cl]

Cyclopentyl (2R)-4-(4-{5-amino-6-[(2,6-dichlorobenzyl)amino]pyrazin-2-yl}benzyl) piperazine-2-carboxylate was synthesised in a similar manner to Example 7 using Intermediate 30 at Stage 1 in the route shown in Scheme 16.

LCMS: purity 100%, m/z 555/557/559 [M+H]$^+$.

$^1$H NMR (300 MHz, DMSO-d$_6$) δ ppm: 7.86 (2H, d, J=8.1 Hz), 7.78 (1H, s), 7.49-7.56 (2H, m), 7.35-7.44 (1H, m), 7.28 (2H, d, J=8.1 Hz), 6.26 (1H, t, J=4.0 Hz), 6.08 (2H, s), 5.09 (1H, t, J=5.8 Hz), 4.85 (2H, d, J=4.1 Hz), 3.36-3.58 (4H, m), 2.92-3.03 (1H, m), 2.60-2.75 (2H, m), 2.42 (2H, dd, J=10.3, 7.1 Hz), 2.22-2.33 (1H, m), 1.73-1.90 (2H, m), 1.43-1.68 (6H, m).

Example 12

Cyclopentyl N-(4-{5-amino-6-[(2,6-dichlorobenzyl)amino]pyrazin-2-yl}benzyl)-L-leucinate

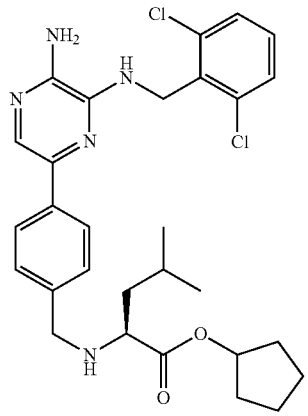 [SMILES: CC(C)C[C@H](NCc1ccc(-c2cnc(N)c(NCc3c(Cl)cccc3Cl)n2)cc1)C(=O)OC1CCCC1]

Cyclopentyl N-(4-{5-amino-6-[(2,6-dichlorobenzyl)amino]pyrazin-2-yl}benzyl)-L-leucinate was synthesised according to Stage 1 of the route shown in Scheme 16 using the free base of Intermediate 32.

LCMS: purity 100%, m/z 556/558 [M+H]$^+$.

$^1$H NMR (300 MHz, CD$_3$OD) δ ppm: 7.91 (2H, d, J=8.3 Hz), 7.71 (1H, s), 7.47-7.44 (2H, m), 7.38-7.29 (3H, m), 5.22-5.16 (1H, m), 5.01 (2H, s), 3.81 (1H, d, J=13.0 Hz), 3.68 (1H, d, J=13.0 Hz), 3.28 (1H, d, J=7.4 Hz), 1.94-1.82 (2H, m), 1.79-1.64 (7H, m), 1.53-1.48 (2H, m), 0.94 (3H, d, J=6.6 Hz), 0.89 (3H, d, J=6.6 Hz).

Example 13 tert-Butyl N-(4-{5-amino-6-[(2,6-dichlorobenzyl)amino]pyrazin-2-yl}benzyl)-L-leucinate

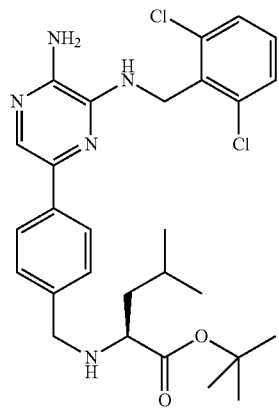 [SMILES: CC(C)C[C@H](NCc1ccc(-c2cnc(N)c(NCc3c(Cl)cccc3Cl)n2)cc1)C(=O)OC(C)(C)C]

tert-Butyl N-(4-{5-amino-6-[(2,6-dichlorobenzyl)amino]pyrazin-2-yl}benzyl)-L-leucinate was synthesised according to Stage 1 of the route shown in Scheme 16 using L-leucine tert-butyl ester as the reactant.

LCMS: purity 100%, m/z 544/546 [M+H]$^+$.

$^1$H NMR (300 MHz, CD$_3$OD) δ ppm: 7.90 (2H, d, J=8.3 Hz), 7.69 (1H, s), 7.45-7.43 (2H, m), 7.38-7.27 (3H, m), 5.00 (2H, s), 3.80 (1H, d, J=12.9 Hz), 3.65 (1H, d, J=12.9 Hz), 3.20 (1H, t, J=7.3 Hz), 1.78-1.69 (1H, m), 1.50 (9H, s), 1.48-1.42 (2H, m), 0.93 (3H, d, J=6.6 Hz), 0.88 (3H, d, J=6.6 Hz).

Example 14

Cyclopentyl (2R)-4-[(4-{5-amino-6-[(2,6-difluorobenzyl)amino]pyrazin-2-yl}benzyl)amino]piperidine-2-carboxylate di-formate

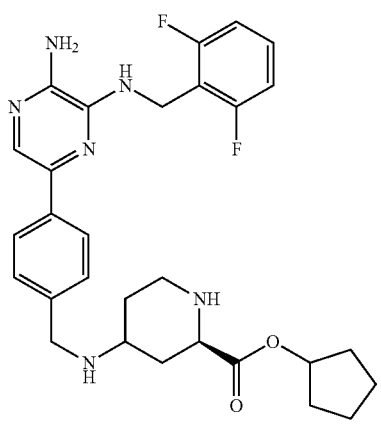 [SMILES: Nc1ncc(-c2ccc(CNC3CCN[C@@H](C(=O)OC4CCCC4)C3)cc2)nc1NCc1c(F)cccc1F]

Cyclopentyl (2R)-4-[(4-{5-amino-6-[(2,6-difluorobenzyl)amino]pyrazin-2-yl}benzyl) amino]piperidine-2-carboxylate was synthesised in a similar manner to Example 7 starting with Intermediate 15 and reacting with Intermediate 22 in Stage 1 in the route shown in Scheme 16. The compound was isolated as the formate salt after preparative HPLC.

LCMS: purity 98%, m/z 537 [M+H]$^+$.

$^1$H NMR (300 MHz, DMSO-d$_6$) δ ppm: 8.2 (2H, s), 7.9-7.75 (2H, m), 7.7 (1H, s), 7.4-7.15 (3H, m), 7.12-6.95 (2H, m), 6.65-6.5 (1H, m), 6.14 (2H, s), 5.1-5.0 (1H, m), 4.60 (2H, m), 3.7 (2H, m), 3.3-1.9 (5H, m), 1.70-1.65 (3H, m), 1.60-1.35 (6H, m).

Example 15

Cyclopentyl N-(4-{5-amino-6-[(2,6-difluorobenzyl)amino]pyrazin-2-yl}benzyl)-L-leucinate

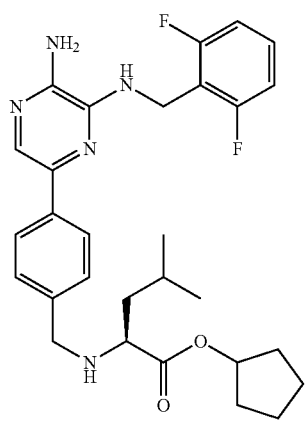 [SMILES: CC(C)C[C@H](NCc1ccc(-c2cnc(N)c(NCc3c(F)cccc3F)n2)cc1)C(=O)OC1CCCC1]

Cyclopentyl N-(4-{5-amino-6-[(2,6-difluorobenzyl)amino]pyrazin-2-yl}benzyl)-L-leucinate was synthesised in a similar manner to Example 7 starting with Intermediate 15 and reacting with the free base of Intermediate 32 according to Stage 1 of the route shown in Scheme 16.

LCMS: purity 98%, m/z 524 [M+H]$^+$.

$^1$H NMR (300 MHz, DMSO-d$_6$) δ ppm: 7.84 (2H, d, J=8.1 Hz), 7.77 (1H, s), 7.47-7.32 (1H, m), 7.28 (2H, d, J=8.3 Hz), 7.10 (2H, t, J=8.0 Hz), 6.63 (1H, t, J=5.0 Hz), 6.16 (2H, s), 5.11 (1H, t, J=5.8 Hz), 4.68 (2H, d, J=4.7 Hz), 3.82-3.4 (2H, m), 3.2-3.05 (1H, m), 2.40-2.25 (1H, m), 1.90-1.78 (2H, m), 1.77-1.50 (7H, m), 1.49-1.30 (2H, m), 0.83 (6H, d, J=2.2 Hz).

Example 16 tert-Butyl N-(4-{5-amino-6-[(2,6-difluorobenzyl)amino]pyrazin-2-yl}benzyl)-L-leucinate

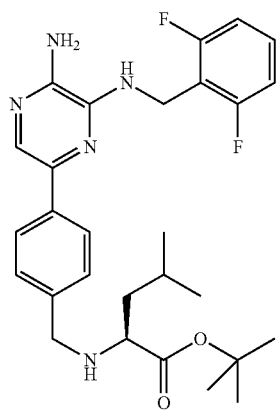 [SMILES: CC(C)C[C@H](NCc1ccc(-c2cnc(N)c(NCc3c(F)cccc3F)n2)cc1)C(=O)OC(C)(C)C]

tert-Butyl N-(4-{5-amino-6-[(2,6-difluorobenzyl)amino]pyrazin-2-yl}benzyl)-L-leucinate was synthesised in a similar manner to Example 7 starting with Intermediate 15 and reacting with L-leucine tert-butyl ester according to Stage 1 of the route shown in Scheme 16.

LCMS: purity 98%, m/z 512 [M+H]$^+$.

$^1$H NMR (300 MHz, DMSO-d$_6$) δ ppm: 7.85 (2H, d, J=8.3 Hz), 7.77 (1H, s), 7.4-7.3 (1H, m), 7.29 (2H, d, J=8.1 Hz), 7.2-7.0 (2H, m), 6.7-6.6 (1H, m), 6.16 (2H, s), 4.68 (2H, d, J=4.7 Hz), 3.9-3.5 (2H, m), 3.12-3.0 (1H, m), 2.3-2.1 (1H, m), 1.8-1.7 (1H, m), 1.44 (9H, s), 1.4-1.3 (2H, m), 0.84 (6H, d, J=2.2 Hz).

Example 17

Cyclopentyl (2R)-4-[(4-{5-amino-6-[(2-chloro-6-fluorobenzyl)amino]pyrazin-2-yl}benzyl)amino]piperidine-2-carboxylate

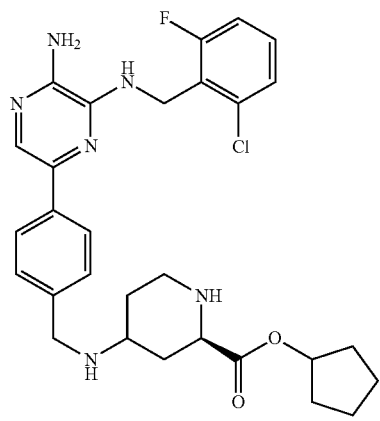

Cyclopentyl (2R)-4-[(4-{5-amino-6-[(2-chloro-6-fluorobenzyl)amino]pyrazin-2-yl}benzyl)amino]piperidine-2-carboxylate was synthesised in a similar manner to Example 7 starting with Intermediate 16 and reacting with Intermediate 22 in Stage 1 in the route shown in Scheme 16.

LCMS: m/z 553 [M+H]$^+$.

$^1$H NMR (300 MHz, DMSO-d$_6$) δ ppm: 7.83 (2H, d, J=8.3 Hz), 7.76 (1H, s), 7.46-7.2 (5H, m), 6.55-6.4 (1H, m), 6.15 (2H, s), 5.12-5.0 (1H, m), 4.8-4.65 (2H, m), 3.72 (2H, br, s), 3.2-2.86 (2H, m), 2.6-2.3 (2H, m), 2.1-1.9 (3H, m), 1.85-1.70 (3H, m), 1.65-1.45 (6H, m), 1.15-0.91 (2H, m).

Example 18

Cyclopentyl (2R)-4-[(4-{5-amino-6-[(2,6-dichlorobenzyl)amino]pyrazin-2-yl}-2-chlorobenzyl)amino]piperidine-2-carboxylate

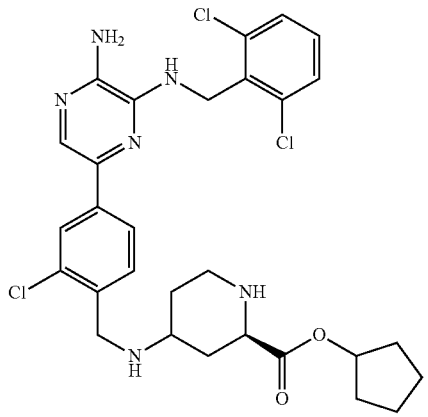 [SMILES: Nc1ncc(-c2ccc(CNC3CCN[C@@H](C(=O)OC4CCCC4)C3)c(Cl)c2)nc1NCc1c(Cl)cccc1Cl]

Cyclopentyl (2R)-4-[(4-{5-amino-6-[(2,6-dichlorobenzyl)amino]pyrazin-2-yl}-2-chloro benzyl)amino]piperidine-2-carboxylate was synthesised in a similar manner to Example 7 starting with Intermediate 17 and reacting with Intermediate 22 in Stage 1 in the route shown in Scheme 16.

LCMS: purity 98%, m/z 603/605 [M+H]$^+$.

$^1$H NMR (300 MHz, DMSO-d$_6$) δ ppm: 7.95-7.88 (1H, m), 7.87-7.79 (2H, m), 7.60-7.48 (3H, m), 7.46-7.35 (1H, m), 6.48-6.38 (1H, s), 6.29 (2H, s), 5.13-5.0 (1H, m), 4.82 (2H, d, J=4.3 Hz), 3.81 (2H, s), 3.30 (1H, m), 3.12 (1H, m), 2.95 (1H, m), 2.65-2.4 (2H, m), 2.08 (2H, m), 1.79 (3H, m), 1.70-1.45 (6H, m), 1.05 (2H, m).

Example 19

Cyclopentyl (2R)-4-[(4-{5-amino-6-[(2,6-dichlorobenzyl)amino]pyrazin-2-yl}-2-methylbenzyl)amino]piperidine-2-carboxylate

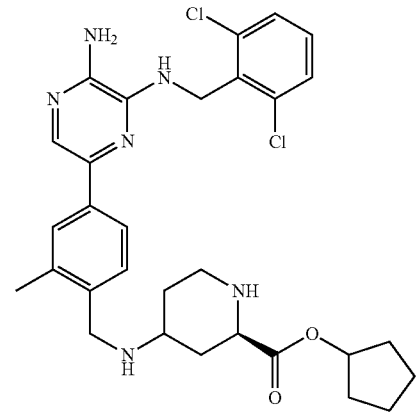 [SMILES: Cc1cc(-c2cnc(N)c(NCc3c(Cl)cccc3Cl)n2)ccc1CNC1CCN[C@@H](C(=O)OC2CCCC2)C1]

Cyclopentyl (2R)-4-[(4-{5-amino-6-[(2,6-dichlorobenzyl)amino]pyrazin-2-yl}-2-methylbenzyl)amino]piperidine-2-carboxylate was synthesised in a similar manner to Example 7 starting with Intermediate 18 and reacting with Intermediate 22 in Stage 1 in the route shown in Scheme 16.

LCMS: purity 98%, m/z 583/585 [M+H]$^+$.

$^1$H NMR (300 MHz, DMSO-d$_6$) δ ppm: 7.77 (1H, s), 7.73-7.63 (2H, m), 7.60-7.48 (2H, m), 7.45-7.2 (2H, m), 6.4-6.3 (1H, s), 6.14 (2H, s), 5.15-5.0 (1H, m), 4.82 (2H, d, J=4.0 Hz), 3.70 (2H, s), 3.45-2.9 (4H, m), 2.6-2.32 (3H, m), 2.34 (3H, s), 2.1-2.0 (1H, m), 1.90-1.75 (3H, m), 1.74-1.40 (5H, m) 1.15-0.95 (2H, m).

Example 20

Cyclopentyl 4-(4-{5-amino-6-[(2,6-dichlorobenzyl)amino]pyrazin-2-yl}-2-ethylbenzyl)piperazine-2-carboxylate

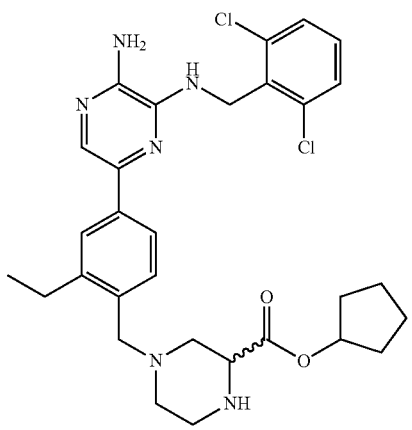 [SMILES: CCc1cc(-c2cnc(N)c(NCc3c(Cl)cccc3Cl)n2)ccc1CN1CCNC(C(=O)OC2CCCC2)C1]

Cyclopentyl 4-(4-{5-amino-6-[(2,6-dichlorobenzyl)amino]pyrazin-2-yl}-2-ethylbenzyl) piperazine-2-carboxylate was synthesised in a similar manner to Example 7 starting with Intermediate 19 and reacting with Intermediate 28 in Stage 1 in the route shown in Scheme 16.

LCMS: purity 98%, m/z 583/585 [M+H]$^+$.

$^1$H NMR (300 MHz, DMSO-d$_6$) δ ppm: 7.77 (1H, s), 7.76-7.74 (1H, m), 7.70-7.64 (1H, m), 7.60-7.50 (2H, m), 7.48-7.35 (1H, m), 7.24-7.18 (1H, m), 6.40-6.30 (1H, m), 6.17 (2H, s), 5.10-5.00 (1H, m), 4.83 (2H, d, J=1.4 Hz), 3.50-3.40 (2H, m), 3.39-3.25 (2H, m under the water peak), 2.99-2.86 (1H, m), 2.71 (2H, q, J=2.5 Hz), 2.65-2.40 (3H, m under the DMSO peak), 2.38-2.22 (2H, m), 1.90-1.68 (2H, m), 1.67-1.40 (6H, m), 1.19 (3H, t, J=2.5 Hz).

Example 21 tert-Butyl (2R)-4-[(4-{5-amino-6-[(2,6-dichlorobenzyl)amino]pyrazin-2-yl}benzyl)amino]piperidine-2-carboxylate

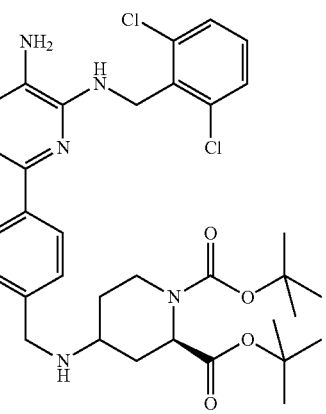

tert-Butyl (2R)-4-[(4-{5-amino-6-[(2,6-dichlorobenzyl)amino]pyrazin-2-yl}benzyl) amino]piperidine-2-carboxylate was synthesised as shown by the route in Scheme 17.

Scheme 17

[Scheme structures showing Intermediate 14 reacting via Stage 1 (Intermediate 25) and Stage 2]

-continued

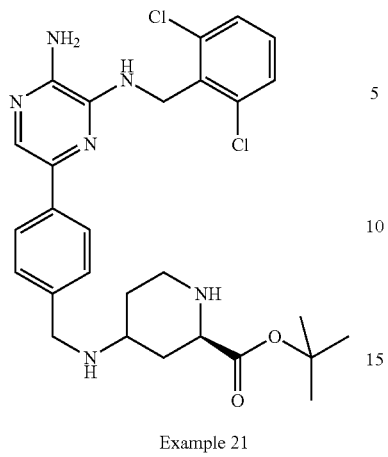

Example 21

Stage 1. Di-tert-butyl (2R)-4-[(4-{5-amino-6-[(2,6-dichlorobenzyl)amino]pyrazin-2-yl}benzyl)amino]piperidine-1,2-dicarboxylate Intermediate 14 (100 mg, 0.27 mmol) and Intermediate 25 (89 mg, 0.29 mmol) were dissolved in DCE (10 mL) and stirred at RT for 2 hrs. STAB (114 mg, 0.29 mmol) was added and the reaction was stirred for a further 18 hrs. The reaction was quenched by the addition of sat $Na_2CO_3$ (20 mL) and vigorously stirred for 20 mins. The aqueous layer was separated and further extracted with DCM (2×20 mL) and the combined organics were dried over $MgSO_4$, filtered, concentrated in vacuo and purified by column chromatography (80% EtOAc/heptane) to give the title compound as an orange oil (143 mg, 81%).

LCMS: m/z 657/659 $[M+H]^+$.

Stage 2. tert-Butyl (2R)-4-[(4-{5-amino-6-[(2,6-dichlorobenzyl)amino]pyrazin-2-yl}benzyl)amino]piperidine-2-carboxylate Di-tert-butyl (2R)-4-[(4-{5-amino-6-[(2,6-dichlorobenzyl)amino]pyrazin-2-yl}benzyl) amino]piperidine-1,2-dicarboxylate (143 mg, 0.22 mmol) was dissolved in dioxane (5 mL) and cooled to 0° C. before the addition of 4M HCl in dioxane (20 mL). The reaction was stirred at 0° C. for 2 hrs. The reaction was basified to pH12 using 2N NaOH and extracted with EtOAc (3×25 mL). The combined organic layers were washed with brine (20 mL), dried over $MgSO_4$, filtered and concentrated in vacuo to give a yellow oil, which was purified by preparative HPLC to give the title compound as a pale yellow solid (37 mg, 31%).

LCMS: purity 100%, m/z 557/559 $[M+H]^+$.

$^1$H NMR (300 MHz, $CDCl_3$) δ ppm: 7.96-7.91 (3H, m), 7.41-7.33 (4H, m), 7.21-7.16 (1H, m), 5.04 (2H, d, J=5.5 Hz), 4.52 (1H, t, J=5.5 Hz), 4.31 (2H, br s), 3.90 (2H, s), 3.25-3.17 (2H, m), 2.72-2.57 (2H, m), 2.30 (1H, d, J=12.2 Hz), 1.94 (1H, d, J=11.9 Hz), 1.73 (2H, br, s), 1.47 (9H, s), 1.29-1.17 (2H, m).

Example 22 tert-Butyl (2S)-4-[(4-{5-amino-6-[(2,6-dichlorobenzyl)amino]pyrazin-2-yl}benzyl)amino]piperidine-2-carboxylate

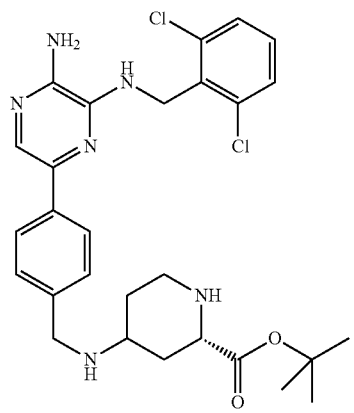 [SMILES: CC(C)(C)OC(=O)[C@@H]1CC(NCc2ccc(-c3cnc(N)c(NCc4c(Cl)cccc4Cl)n3)cc2)CCN1]

tert-Butyl (2S)-4-[(4-{5-amino-6-[(2,6-dichlorobenzyl)amino]pyrazin-2-yl}benzyl) amino]piperidine-2-carboxylate was synthesised in a similar manner to Example 21 using Intermediate 26 at Stage 1 in the route shown in Scheme 17.

LCMS: purity 96%, m/z 557/559 $[M+H]^+$.

$^1$H NMR (300 MHz, $CDCl_3$) δ ppm: 7.96 (2H, d, J=8.3 Hz), 7.93 (1H, s), 7.45-7.35 (4H, m), 7.21 (1H, dd, J=7.3, 8.7 Hz), 5.04 (2H, d, J=5.5 Hz), 4.43 (1H, t, J=5.5 Hz), 4.22 (2H, br, s), 3.91 (2H, s), 3.25-3.17 (2H, m), 2.75-2.58 (2H, m), 2.31 (1H, d, J=12.4 Hz), 1.96 (1H, d, J=12.4 Hz), 1.47 (9H, s), 1.35-1.21 (2H, s).

Example 23 tert-Butyl 4-(4-{5-amino-6-[(2,6-dichlorobenzyl)amino]pyrazin-2-yl}benzyl)piperazine-2-carboxylate

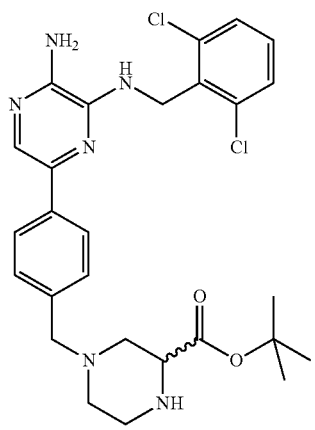 [SMILES: CC(C)(C)OC(=O)C1CN(Cc2ccc(-c3cnc(N)c(NCc4c(Cl)cccc4Cl)n3)cc2)CCN1]

tert-Butyl 4-(4-{5-amino-6-[(2,6-dichlorobenzyl)amino]pyrazin-2-yl}benzyl)piperazine-2-carboxylate was synthesised in a similar manner to Example 21 using Intermediate 31 at Stage 1 in the route shown in Scheme 17.

LCMS: purity 100%, m/z 543/545 [M+H]⁺.

¹H NMR (300 MHz, CDCl₃) δ ppm: 7.96-7.93 (3H, m), 7.41-7.37 (4H, m), 7.20 (1H, dd, J=7.3, 8.7 Hz), 5.04 (2H, d, J=5.7 Hz), 4.45 (1H, t, J=5.5 Hz), 4.25 (2H, br, s), 3.64 (1H, d, J=13.2 Hz), 3.51-3.46 (2H, m), 3.11-3.05 (1H, m), 2.93-2.82 (2H, m), 2.61 (1H, d, J=11.3 Hz), 2.42 (1H, t, J=9.1 Hz), 2.26 (1H, t, J=8.6 Hz), 1.94 (1H, br, s), 1.46 (9H, s).

Example 24 tert-Butyl (2R)-4-[(4-{5-amino-6-[(2,6-difluorobenzyl)amino]pyrazin-2-yl}benzyl)amino]piperidine-2-carboxylate

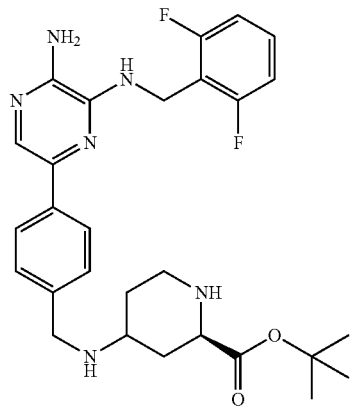 [SMILES: CC(C)(C)OC(=O)[C@H]1CC(NCc2ccc(-c3cnc(N)c(NCc4c(F)cccc4F)n3)cc2)CCN1]

tert-Butyl (2R)-4-[(4-{5-amino-6-[(2,6-difluorobenzyl)amino]pyrazin-2-yl}benzyl) amino]piperidine-2-carboxylate was synthesised in a similar manner to Example 21 starting with Intermediate 15 and reacting with Intermediate 25 in Stage 1 in the route shown in Scheme 17.

LCMS: purity 98%, m/z 525 [M+H]⁺.

¹H NMR (300 MHz, DMSO-d₆) δ ppm: 7.9-7.8 (2H, m), 7.76 (1H, s), 7.47-7.26 (3H, m), 7.18-7.0 (2H, m), 6.62 (1H, t, J=4.9 Hz), 6.14 (2H, s), 4.68 (2H, d, J=4.7 Hz), 3.73 (2H, s), 3.2-2.85 (2H, m), 2.6-2.25 (2H, m), 2.15-2.00 (1H, m), 1.99-1.85 (1H, m), 1.80-1.60 (1H, m), 1.40 (9H, s), 1.14-0.90 (2H, m).

Example 25 tert-Butyl (2R)-4-[(4-{5-amino-6-[(2,6-dichlorobenzyl)amino]pyrazin-2-yl}-2-chlorobenzyl)amino]piperidine-2-carboxylate

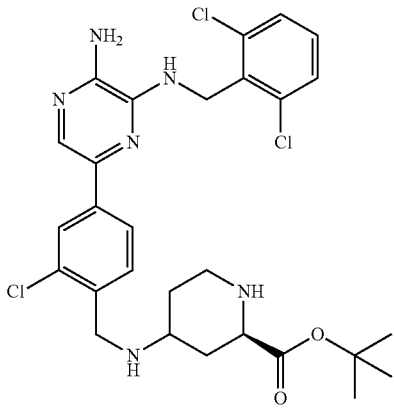 [SMILES: CC(C)(C)OC(=O)[C@H]1CC(NCc2ccc(-c3cnc(N)c(NCc4c(Cl)cccc4Cl)n3)cc2Cl)CCN1]

tert-Butyl (2R)-4-[(4-{5-amino-6-[(2,6-dichlorobenzyl)amino]pyrazin-2-yl}-2-chloro benzyl)amino]piperidine-2-carboxylate was synthesised in a similar manner to Example 21 starting with Intermediate 17 and reacting with Intermediate 25 in Stage 1 in the route shown in Scheme 17.

LCMS: purity 96%, m/z 591/593 [M+H]⁺.

¹H NMR (300 MHz, DMSO-d₆) δ ppm: 7.98-7.88 (1H, m), 7.87-7.75 (2H, m), 7.58-7.48 (3H, m), 7.45-7.35 (1H, m), 6.48-6.4 (1H, m), 6.29 (2H, s), 4.82 (2H, d, J=4.0 Hz), 3.82 (2H, s), 3.32-3.26 (1H, m), 3.1-2.9 (2H, m), 2.5-2.4 (2H, m), 2.15-2.00 (1H, m), 1.99-1.85 (2H, m), 1.80-1.6 (1H, m), 1.39 (9H, s), 1.25-0.90 (2H, m).

Example 26 tert-Butyl (2R)-4-[(4-{5-amino-6-[(2,6-dichlorobenzyl)amino]pyrazin-2-yl}-2-methylbenzyl)amino]piperidine-2-carboxylate

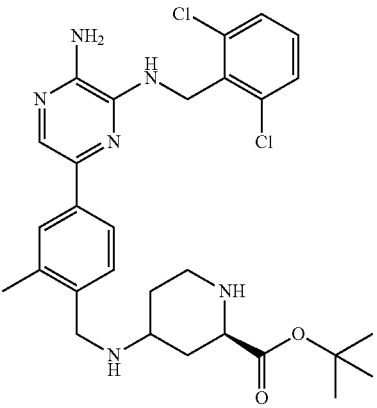 [SMILES: Cc1cc(-c2cnc(N)c(NCc3c(Cl)cccc3Cl)n2)ccc1CNC1CCN[C@@H](C(=O)OC(C)(C)C)C1]

tert-Butyl (2R)-4-[(4-{5-amino-6-[(2,6-dichlorobenzyl)amino]pyrazin-2-yl}-2-methylbenzyl)amino]piperidine-2-carboxylate was synthesised in a similar manner to Example 21 starting with Intermediate 18 and reacting with Intermediate 25 in Stage 1 in the route shown in Scheme 17.

LCMS: purity 98%, m/z 571/573 [M+H]⁺.

¹H NMR (300 MHz, DMSO-d₆) δ ppm: 7.84-7.74 (1H, m), 7.7-7.62 (2H, m), 7.59-7.45 (2H, m), 7.44-7.25 (2H, m), 6.41-6.24 (1H, m), 6.22-6.04 (2H, m), 4.91-4.7 (2H, m), 3.79-3.63 (2H, m), 3.6-3.2 (4H, m), 3.15-2.8 (2H, m), 2.5-2.4 (1H, m), 2.35 (3H, s), 2.2-2.0 (1H, m), 1.95-1.60 (1H, m), 1.39 (9H, s), 1.15-0.9 (1H, m).

Example 27

Cyclopentyl (2R)-4-[(4-{5-amino-6-[(2,6-dichlorobenzyl)amino]pyrazin-2-yl}benzyl)(ethyl)amino]piperidine-2-carboxylate

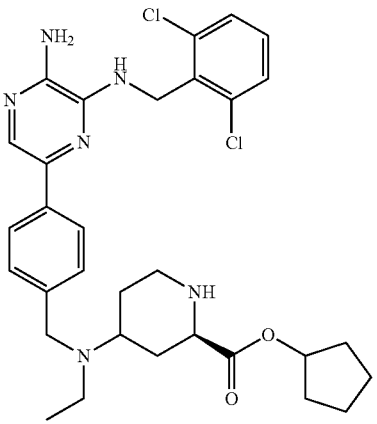 [SMILES: CCN(Cc1ccc(-c2cnc(N)c(NCc3c(Cl)cccc3Cl)n2)cc1)C1CCN[C@@H](C(=O)OC2CCCC2)C1]

Cyclopentyl (2R)-4-[(4-{5-amino-6-[(2,6-dichlorobenzyl)amino]pyrazin-2-yl}benzyl) (ethyl)amino]piperidine-2-carboxylate was synthesised by the route shown in Scheme 18.

Scheme 18

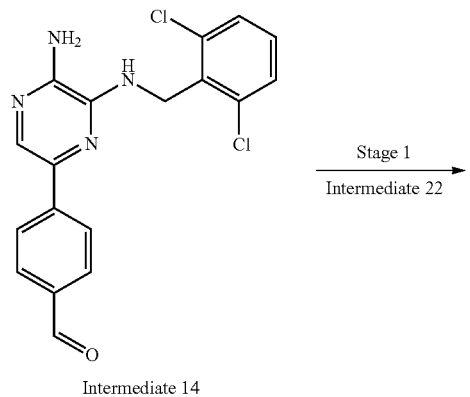

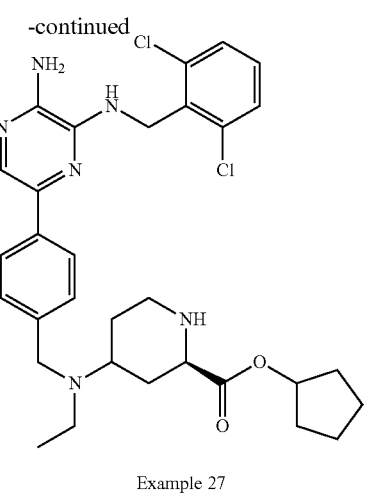

Example 27

Stage 1: 1-tert-Butyl 2-cyclopentyl (2R)-4-[(4-{5-amino-6-[(2,6-dichlorobenzyl)amino]pyrazin-2-yl}benzyl)amino]piperidine-1,2-dicarboxylate Intermediate 14 (150 mg, 0.40 mmol) and Intermediate 22 (138 mg, 0.44 mmol) were dissolved in DCE (15 mL) and stirred at RT for 2 hrs. STAB (170 mg, 0.80 mmol) was added and the reaction was stirred for a further 18 hrs. The reaction was quenched by the addition of sat $Na_2CO_3$ (20 mL) and vigorously stirred for 20 mins. The aqueous layer was separated and further extracted with DCM (2×20 mL) and the combined organics were dried over $MgSO_4$, filtered, concentrated in vacuo and purified by column chromatography (80% EtOAc/heptane) to give the title compound as an orange oil (168 mg, 62%).

LCMS: m/z 669/671 [M+H]$^+$.

Stage 2: 1-tert-Butyl 2-cyclopentyl (2R)-4-[(4-{5-amino-6-[(2,6-dichlorobenzyl)amino]pyrazin-2-yl}benzyl)(ethyl)amino]piperidine-1,2-dicarboxylate To a solution of 1-tert-butyl 2-cyclopentyl (2R)-4-[(4-{5-amino-6-[(2,6-dichlorobenzyl) amino]pyrazin-2-yl}benzyl) amino]piperidine-1,2-dicarboxylate (168 mg, 0.28 mmol) in anhydrous MeCN (4 mL) was added acetaldehyde (37 mg, 0.85 mmol). The reaction was stirred at RT under nitrogen for 10 mins, followed by addition of acetic acid (34 mg, 0.56 mmol) and STAB (132 mg, 0.62 mmol). The reaction was stirred for 1 hour and then quenched by the addition of sat $NaHCO_3$ (10 mL). The aqueous was extracted with DCM (3×20 mL) and the combined organics were dried over $MgSO_4$, filtered and concentrated in vacuo. The product was obtained by column chromatography (50% EtOAc/heptane followed by 70% EtOAc/heptane) to give the title compound as a yellow solid (77 mg, 39%).

LCMS: m/z 697/698/699/700/701 [M+H]$^+$.

Stage 3: Cyclopentyl (2R)-4-[(4-{5-amino-6-[(2,6-dichlorobenzyl)amino]pyrazin-2-yl}benzyl) (ethyl) amino]piperidine-2-carboxylate 1-tert-Butyl 2-cyclopentyl (2R)-4-[(4-{5-amino-6-[(2,6-dichlorobenzyl)amino]pyrazin-2-yl}benzyl)(ethyl)amino] piperidine-1,2-dicarboxylate (77 mg, 0.11 mmol) was stirred in 2M HCl in diethyl ether (5 mL) at RT for 24 hours. The solvent was removed in vacuo and the crude material was purified by preparative HPLC to afford the title compound as an off-white solid (32 mg, 49%).

LCMS: purity 100%, m/z 597/598/599/600 [M+H]$^+$ $^1$H NMR (300 MHz, DMSO-d$_6$) δ ppm: 7.85 (2H, d, J=8.1 Hz), 7.78 (1H, s), 7.49-7.59 (2H, m), 7.37-7.45 (1H, m), 7.33 (2H, d, J=8.1 Hz), 6.27-6.36 (1H, m), 6.15 (2H, s), 5.06 (1H, t, J=5.7 Hz), 4.82 (2H, d, J=3.8 Hz), 3.59 (2H, s), 3.13 (1H, d, J=10.9 Hz), 3.00 (1H, d, J=12.2 Hz), 2.66 (1H, t, J=11.7 Hz), 2.34-2.47 (2H, m), 2.03 (11H, br, s), 1.16-1.41 (2H, m), 0.95 (3H, t, J=6.9 Hz).

Example 28

Cyclopentyl (2R)-4-[(4-{5-amino-6-[(2,6-dichlorobenzyl)amino]pyrazin-2-yl}benzyl)(methyl)amino]piperidine-2-carboxylate

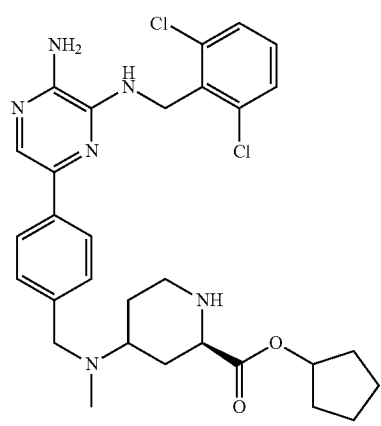 [SMILES: CN(Cc1ccc(-c2cnc(N)c(NCc3c(Cl)cccc3Cl)n2)cc1)C1CCN[C@@H](C(=O)OC2CCCC2)C1]

Cyclopentyl (2R)-4-[(4-{5-amino-6-[(2,6-dichlorobenzyl)amino]pyrazin-2-yl}benzyl) (methyl)amino]piperidine-2-carboxylate was synthesised by the route shown in Scheme 19.

Scheme 19

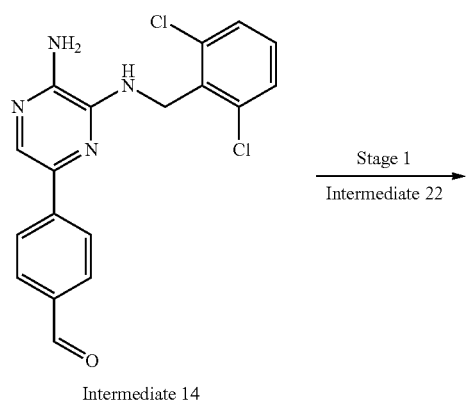

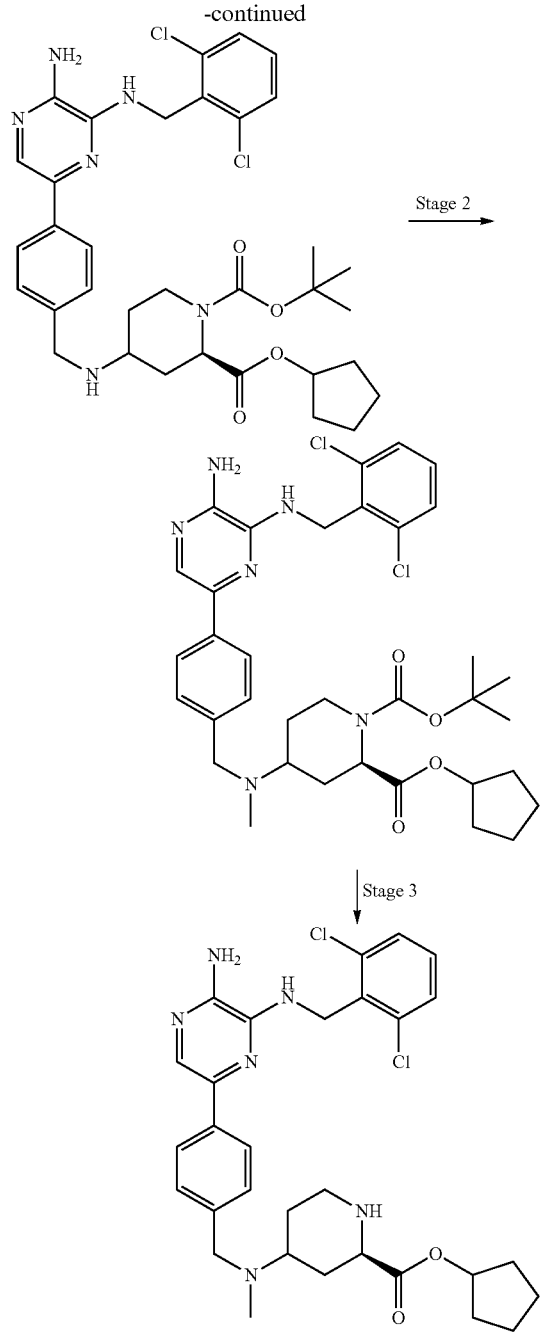

Stage 1: 1-tert-Butyl 2-cyclopentyl (2R)-4-[(4-{5-amino-6-[(2,6-dichlorobenzyl)amino]pyrazin-2-yl}benzyl)amino]piperidine-1,2-dicarboxylate Intermediate 14 (150 mg, 0.40 mmol) and Intermediate 22 (138 mg, 0.44 mmol) were dissolved in DCE (15 mL) and stirred at RT for 2 hrs. STAB (170 mg, 0.80 mmol) was added and the reaction was stirred for a further 18 hrs. The reaction was quenched by the addition of sat Na$_2$CO$_3$ (20 mL) and vigorously stirred for 20 mins. The aqueous layer was separated and further extracted with DCM (2×20 mL)

and the combined organics were dried over MgSO$_4$, filtered, concentrated in vacuo and purified by column chromatography (80% EtOAc/heptane) to give the title compound as an orange oil (168 mg, 62%).

LCMS: m/z 669/671 [M+H]$^+$.

Stage 2: 1-tert-Butyl 2-cyclopentyl (2R)-4-[(4-{5-amino-6-[(2,6-dichlorobenzyl)amino]pyrazin-2-yl}benzyl)(methyl)amino]piperidine-1,2-dicarboxylate To a solution of 1-tert-butyl 2-cyclopentyl (2R)-4-[(4-{5-amino-6-[(2,6-dichlorobenzyl) amino]pyrazin-2-yl}benzyl) amino]piperidine-1,2-dicarboxylate (150 mg, 0.22 mmol) in MeCN (4 mL) was added 37% aq. formaldehyde (16.8 μL, 0.22 mmol). The reaction was stirred at RT for 1.5 hrs, followed by addition of STAB (71 mg, 0.34 mmol). The reaction was stirred for 3 hrs followed by the further addition of 37% aq. formaldehyde (8.4 μL, 0.11 mmol). The reaction was stirred for 18 hrs and then quenched by the addition of sat NaHCO$_3$ (20 mL). The aqueous was extracted with EtOAc (4×20 mL) and the combined organics were dried over MgSO$_4$, filtered and concentrated in vacuo. The crude was purified by automated column chromatography using EtOAc in heptane (gradient 0-80%) to give the title compound, which contained some impurities, as a yellow solid (125 mg, 83%). LCMS: m/z 683/684/685 [M+H]$^+$.

Stage 3: Cyclopentyl (2R)-4-[(4-{5-amino-6-[(2,6-dichlorobenzyl)amino]pyrazin-2-yl}benzyl)(methyl)amino]piperidine-2-carboxylate 1-tert-butyl 2-cyclopentyl (2R)-4-[(4-{5-amino-6-[(2,6-dichlorobenzyl)amino]pyrazin-2-yl}benzyl)(methyl)amino] piperidine-1,2-dicarboxylate (125 mg, 0.18 mmol) was stirred in 2M HCl in diethyl ether (7 mL) at RT for 24 hours. The solvent was removed in vacuo and the crude material was purified by preparative HPLC to afford the title compound as an off-white solid (13 mg, 12%).

LCMS: purity 100%, m/z 583/585/587 [M+H]$^+$.

$^1$H NMR (300 MHz, DMSO-d$_6$) δ ppm: 7.86 (2H, d, J=8.1 Hz), 7.79 (1H, s), 7.50-7.58 (2H, m), 7.36-7.46 (1H, m), 7.30 (2H, d, J=8.1 Hz), 6.28-6.35 (1H, m), 6.17 (2H, br, s), 5.03-5.12 (1H, m), 4.82 (2H, d, J=3.6 Hz), 3.56 (2H, s), 3.10-3.20 (1H, m), 2.96-3.08 (1H, m), 2.54-2.66 (1H, m), 2.33-2.45 (1H, m), 2.12 (3H, s), 1.90-2.07 (2H, m), 1.74-1.88 (2H, m), 1.46-1.71 (7H, m), 1.19-1.44 (2H, m).

Example 29

Cyclopentyl (2R)-4-[(4-{5-amino-6-[(2,6-dichlorobenzyl)amino]pyrazin-2-yl}benzyl)(2-methylpropyl)amino]piperidine-2-carboxylate

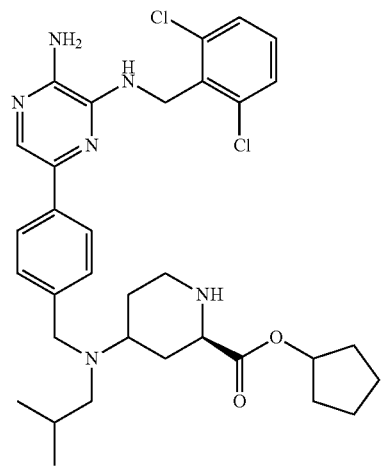 [SMILES: CC(C)CN(Cc1ccc(-c2cnc(N)c(NCc3c(Cl)cccc3Cl)n2)cc1)C1CCN[C@@H](C(=O)OC2CCCC2)C1]

Cyclopentyl (2R)-4-[(4-{5-amino-6-[(2,6-dichlorobenzyl)amino]pyrazin-2-yl}benzyl)(2-methylpropyl)amino]piperidine-2-carboxylate was synthesised by the route shown in Scheme 20.

Scheme 20

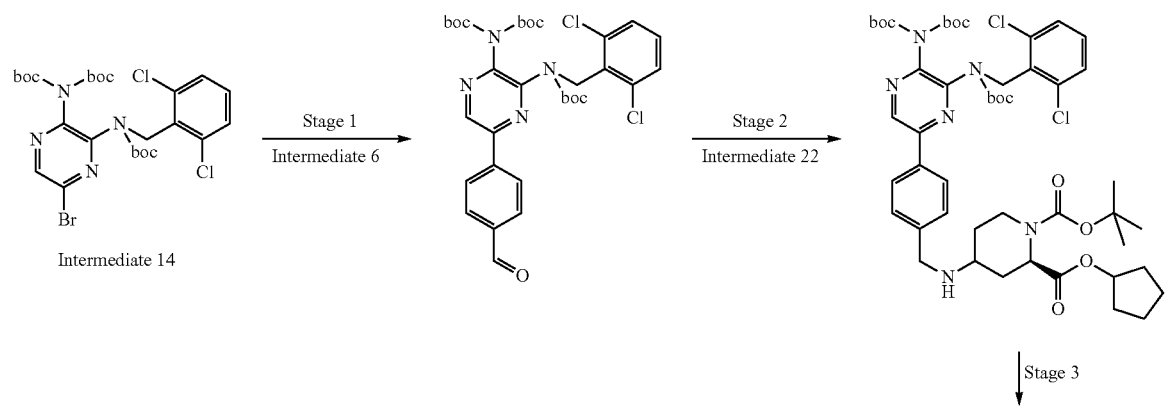

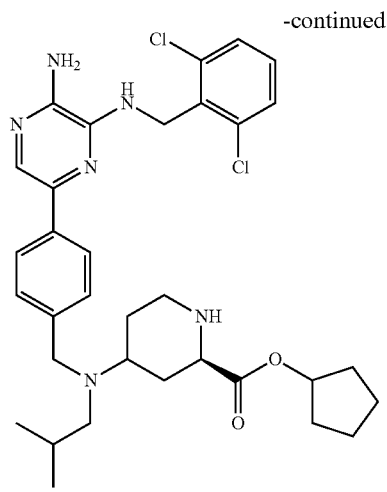
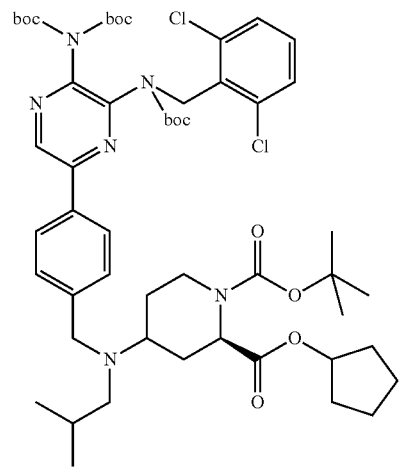

Example 29

Stage 1: Di-tert-butyl {3-[(tert-butoxycarbonyl)(2,6-dichlorobenzyl)amino]-5-(4-formylphenyl)pyrazin-2-yl}imidodicarbonate To a solution of Intermediate 4 (569 mg, 0.88 mmol) in DME (5.5 mL), was added Intermediate 6 (305 mg, 1.3 mmol) and 2N Na$_2$CO$_3$ (1.1 mL, 2.2 mmol) and the solution was degassed by bubbling nitrogen through the reaction mixture. Dichlorobis (triphenylphosphine) palladium (II) (62 mg, 0.088 mmol) was added and the reaction was stirred at 80° C. under nitrogen for 18 hrs for complete reaction. The reaction mixture was filtered through Celite® and the filter cake was washed with EtOAc (100 mL). The combined filtrates were washed with water (30 mL), brine (30 mL), dried over MgSO$_4$, filtered and concentrated in vacuo before purification by column chromatography (20%-30% EtOAc/heptane) to give the title compound as a colourless oil (0.513 g, 87%).

LCMS: m/z 695/697/699 [M+Na]$^+$.

Stage 2: 1-tert-Butyl 2-cyclopentyl (2R)-4-[(4-{5-[bis(tert-butoxycarbonyl)amino]-6-[(tert-butoxycarbonyl)(2,6-dichlorobenzyl)amino]pyrazin-2-yl}benzyl)amino]piperidine-1,2-dicarboxylate Di-tert-butyl {3-[(tert-butoxycarbonyl)(2,6-dichlorobenzyl)amino]-5-(4-formylphenyl) pyrazin-2-yl}imidodicarbonate (250 mg, 0.37 mmol) and Intermediate 22 (128 mg, 0.41 mmol) were dissolved in DCE (6 mL) and stirred at RT, under nitrogen for 1 hr. STAB (157 mg, 0.74 mmol) was added and the reaction was stirred for a further 18 hrs. The reaction was quenched by the addition of sat Na$_2$CO$_3$ (10 mL) and DCM (10 mL). The aqueous layer was separated and further extracted with DCM (3×20 mL) and the combined organics were dried over MgSO$_4$, filtered, concentrated in vacuo and purified by column chromatography (40% EtOAc/heptane) to give the title compound as an orange oil (252 mg, 70%).

LCMS: m/z 969/970/971 [M+H]$^+$.

Stage 3: 1-tert-Butyl 2-cyclopentyl (2R)-4-[(4-{5-[bis(tert-butoxycarbonyl)amino]-6-[(tert-butoxycarbonyl)(2,6-dichlorobenzyl)amino]pyrazin-2-yl}benzyl)(2-methylpropyl) amino]piperidine-1,2-dicarboxylate 1-tert-Butyl 2-cyclopentyl (2R)-4-[(4-{5-[bis(tert-butoxycarbonyl)amino]-6-[(tert-butoxycarbonyl)(2,6-dichlorobenzyl)amino]pyrazin-2-yl}benzyl)amino]piperidine-1,2-dicarboxylate (80 mg, 0.08 mmol), isobutyraldehyde (113 µL, 1.20 mmol) and acetic acid (94 µL, 1.6 mmol) were dissolved in DCE (3 mL) and stirred at RT under nitrogen for 1 hr. STAB (35 mg, 0.33 mmol) was added and the reaction was stirred 2.5 hrs. Further isobutyraldehyde (75 µL, 0.8 mmol) was added and the reaction was stirred for 1.5 hrs, before further STAB (35 mg, 0.33 mmol) was added. The reaction was stirred for 1.5 hrs and then quenched with sat NaHCO$_3$ (10 mL) and DCM (10 mL). The organic layer was separated and the aqueous was extracted with DCM (3×10 mL). The combined organics were dried over MgSO$_4$, filtered, concentrated in vacuo and purified by automated column chromatography using EtOAc in heptane (gradient 0-30%) to give the title compound as a colourless oil (70 mg, 83%).

LCMS: m/z 1025/1027/1029 [M+H]$^+$.

Stage 4: Cyclopentyl (2R)-4-[acetyl(4-{5-amino-6-[(2,6-dichlorobenzyl)amino]pyrazin-2-yl}benzyl) amino]piperidine-2-carboxylate 1-tert-Butyl 2-cyclopentyl (2R)-4-[(4-{5-[bis(tert-butoxycarbonyl)amino]-6-[(tert-butoxycarbonyl)(2,6-dichlorobenzyl)amino]pyrazin-2-yl}benzyl)(2-methylpropyl) amino]piperidine-1,2-dicarboxylate (106 mg, 0.10 mmol) was stirred in dioxane (2 mL) and 4M HCl in dioxane (3 mL) was added. The reaction was stirred for 18 hrs until completion. The solvent was removed in vacuo to give a yellow solid, which was purified by preparative HPLC to give the title compound as an off-white solid (16 mg, 26%).

LCMS: purity 100%, m/z 625/627/629 [M+H]$^+$.

$^1$H NMR (300 MHz, DMSO-d$_6$) δ ppm 7.86 (2H, d, J=8.1 Hz), 7.79 (1H, s), 7.50-7.59 (2H, m), 7.37-7.45 (1H, m), 7.32 (2H, d, J=8.1 Hz), 6.27-6.36 (1H, m), 6.17 (2H, s), 5.06 (1H, t, J=5.7 Hz), 4.82 (2H, d, J=3.8 Hz), 3.59 (2H, s), 3.08

(1H, d, J=9.8 Hz), 2.98 (1H, d, J=13.6 Hz), 2.54-2.64 (1H, m), 2.36 (1H, t, J=10.9 Hz), 2.20 (2H, d, J=6.8 Hz), 2.05 (1H, br, s), 1.72-1.93 (3H, m), 1.48-1.71 (8H, m), 1.15-1.40 (2H, m), 0.81 (6H, d, J=6.4 Hz).

Example 30 tert-Butyl (2R)-4-[(4-{5-amino-6-[(2,6-dichlorobenzyl)amino]pyrazin-2-yl}benzyl)(ethyl)amino]piperidine-2-carboxylate

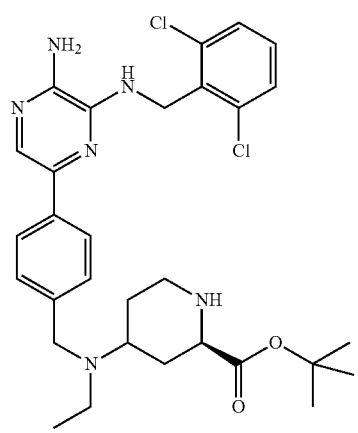 [SMILES: CCN(Cc1ccc(-c2cnc(N)c(NCc3c(Cl)cccc3Cl)n2)cc1)C1CCN[C@@H](C(=O)OC(C)(C)C)C1]

tert-Butyl (2R)-4-[(4-{5-amino-6-[(2,6-dichlorobenzyl)amino]pyrazin-2-yl}benzyl)(ethyl) amino]piperidine-2-carboxylate was synthesised by the route shown in Scheme 21.

Scheme 21

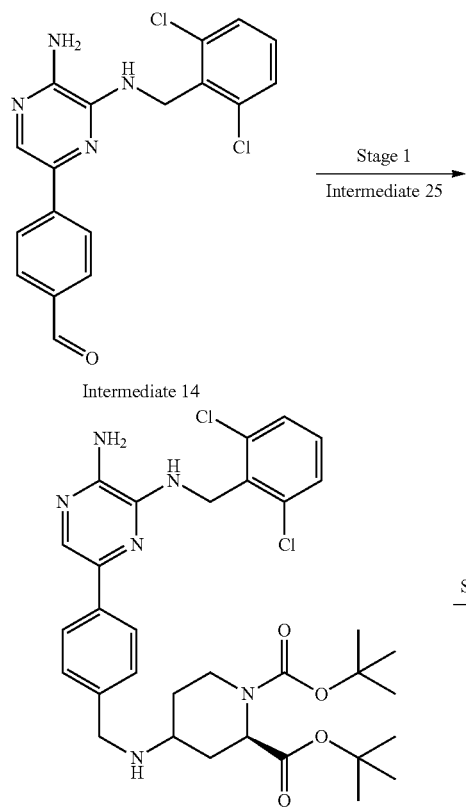

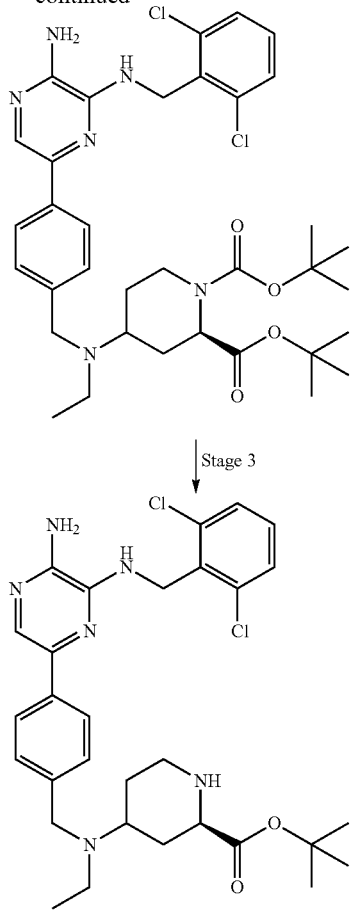

Example 30

Stage 1. Di-tert-butyl (2R)-4-[(4-{5-amino-6-[(2,6-dichlorobenzyl)amino]pyrazin-2-yl}benzyl)amino]piperidine-1,2-dicarboxylate Intermediate 14 (100 mg, 0.27 mmol) and Intermediate 25 (89 mg, 0.29 mmol) were dissolved in DCE (10 mL) and stirred at RT for 2 hrs. STAB (114 mg, 0.29 mmol) was added and the reaction was stirred for a further 18 hrs. The reaction was quenched by the addition of sat Na$_2$CO$_3$ (20 mL) and vigorously stirred for 20 mins. The aqueous layer was separated and further extracted with DCM (2×20 mL) and the combined organics were dried over MgSO$_4$, filtered, concentrated in vacuo and purified by column chromatography (80% EtOAc/heptane) to give the title compound as an orange oil (143 mg, 81%).

LCMS: m/z 657/659 [M+H]$^+$.

Stage 2: Di-tert-butyl (2R)-4-[(4-{5-amino-6-[(2,6-dichlorobenzyl)amino]pyrazin-2-yl}benzyl)(ethyl)amino]piperidine-1,2-dicarboxylate To a solution of di-tert-butyl (2R)-4-[(4-{5-amino-6-[(2,6-dichlorobenzyl)amino]pyrazin-2-yl}benzyl)amino]piperidine-1,2-dicarboxylate (150 mg, 0.23 mmol) in MeCN (4 mL) was added acetaldehyde (20 mg, 0.46 mmol). The reaction was stirred at RT under nitrogen for 25 mins, followed by addition of acetic acid (27 mg, 0.46 mmol) and STAB (106 mg, 0.50 mmol). The reaction was stirred for 30 mins and then quenched by the addition of sat NaHCO₃ (10 mL). The aqueous was extracted with EtOAc (3×20 mL) and the combined organics were dried over MgSO₄, filtered and concentrated in vacuo. The product was obtained by automated column chromatography using EtOAc in heptane (gradient 0-100%) to give the title compound as a yellow oil (83 mg, 53%).

LCMS: m/z 685/687/689 [M+H]⁺.

Stage 3: tert-Butyl (2R)-4-[(4-{5-amino-6-[(2,6-dichlorobenzyl)amino]pyrazin-2-yl}benzyl)(ethyl) amino]piperidine-2-carboxylate Di-tert-butyl (2R)-4-[(4-{5-amino-6-[(2,6-dichlorobenzyl)amino]pyrazin-2-yl}benzyl) (ethyl)amino]piperidine-1,2-dicarboxylate (47 mg, 0.069 mmol) was dissolved in DCM (0.5 mL) and cooled to 0° C. before the addition of 4M HCl in dioxane (2.5 mL). The reaction was stirred at 0° C. for 1 hour. The reaction was basified to pH14 using 2N NaOH (10 mL) and extracted with EtOAc (3×30 mL). The combined organic layers were washed with brine (25 mL), dried over MgSO₄, filtered and concentrated in vacuo to give a yellow oil which was purified by preparative HPLC to give the title compound as a white solid (6 mg, 15%).

LCMS: purity 97.5%, m/z 585/587/589 [M+H]⁺.

$^1$H NMR (300 MHz, DMSO-d$_6$) δ ppm: 7.85 (2H, d, J=8.1 Hz), 7.77 (1H, s), 7.50-7.54 (2H, m), 7.36-7.43 (1H, m), 7.33 (2H, d, J=8.3 Hz), 6.24 (1H, t, J=4.2 Hz), 6.05 (2H, s), 4.85 (2H, d, J=4.3 Hz), 3.62 (2H, s), 2.98-3.09 (2H, m), 2.66 (1H, t, J=11.7 Hz), 2.53 (2H, d, J=7.2 Hz), 2.37-2.47 (1H, m), 1.93 (1H, d, J=12.1 Hz), 1.58-1.69 (1H, m), 1.41 (9H, s), 1.19-1.37 (2H, m), 0.96 (3H, t, J=7.0 Hz).

Example 31

Cyclopentyl (2R)-4-[acetyl(4-{5-amino-6-[(2,6-dichlorobenzyl) amino]pyrazin-2-yl}benzyl)amino] piperidine-2-carboxylate

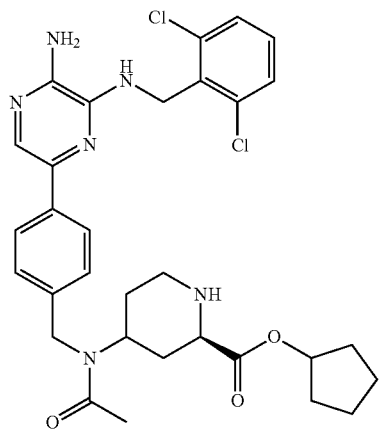 [SMILES: CC(=O)N(Cc1ccc(-c2cnc(N)c(NCc3c(Cl)cccc3Cl)n2)cc1)C1CCN[C@@H](C(=O)OC2CCCC2)C1]

Cyclopentyl (2R)-4-[(4-{5-amino-6-[(2,6-dichlorobenzyl)amino]pyrazin-2-yl}benzyl) (ethyl)amino]piperidine-2-carboxylate was synthesised by the route shown in Scheme 22.

Scheme 22

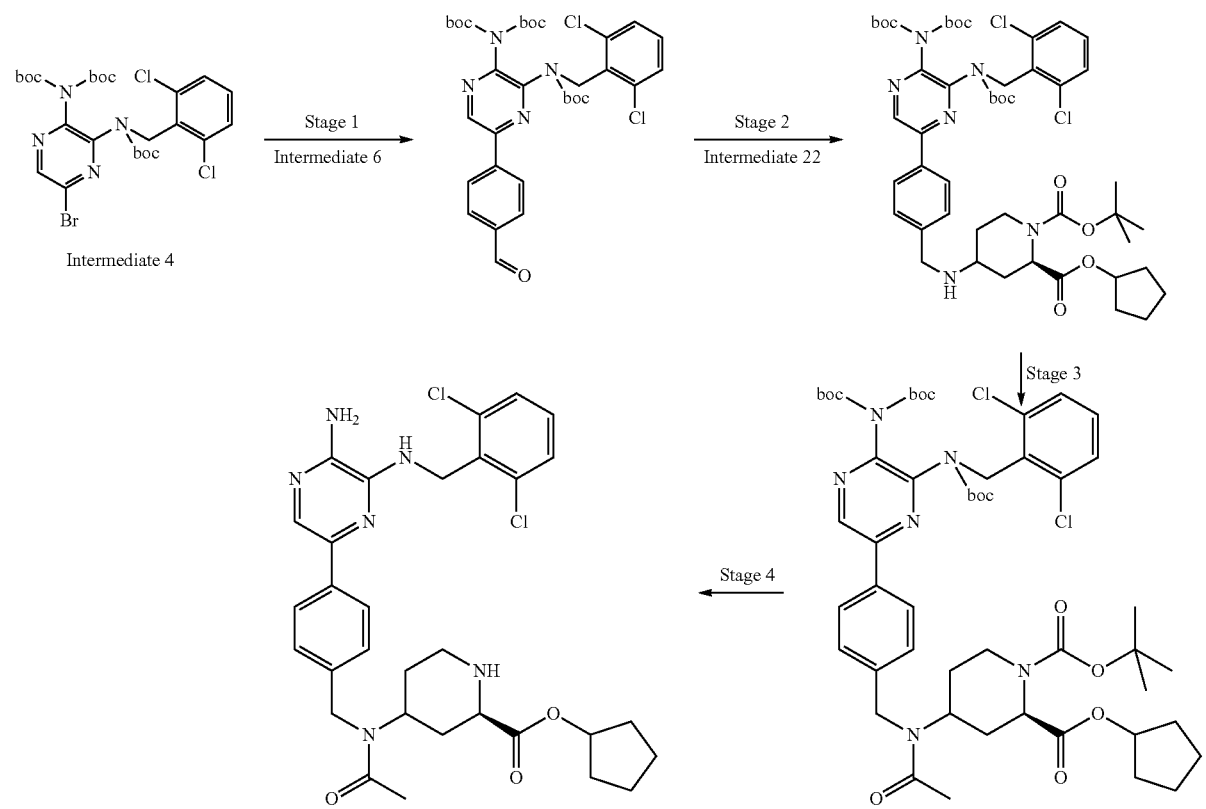

Example 31

Stage 1: Di-tert-butyl {3-[(tert-butoxycarbonyl)(2,6-dichlorobenzyl)amino]-5-(4-formylphenyl)pyrazin-2-yl}imidodicarbonate To a solution of Intermediate 4 (569 mg, 0.88 mmol) in DME (5.5 mL), was added Intermediate 6 (305 mg, 1.3 mmol) and 2N Na₂CO₃ (1.1 mL, 2.2 mmol) and the solution was degassed by bubbling nitrogen through the reaction mixture. Dichlorobis (triphenylphosphine) palladium (II) (62 mg, 0.088 mmol) was added and the reaction was stirred at 80° C. under nitrogen for 18 hrs for complete reaction. The reaction mixture was filtered through Celite® and the filter cake was washed with EtOAc (100 mL). The combined filtrates were washed with water (30 mL), brine (30 mL), dried over MgSO₄, filtered and concentrated in vacuo before purification by column chromatography (20%-30% EtOAc/heptane) to give the title compound as a colourless oil (0.513 g, 87%).

LCMS: m/z 695/697/699 [M+Na]⁺.

Stage 2: 1-tert-Butyl 2-cyclopentyl (2R)-4-[(4-{5-[bis(tert-butoxycarbonyl)amino]-6-[(tert-butoxycarbonyl)(2,6-dichlorobenzyl)amino]pyrazin-2-yl}benzyl)amino]piperidine-1,2-dicarboxylate Di-tert-butyl {3-[(tert-butoxycarbonyl)(2,6-dichlorobenzyl)amino]-5-(4-formylphenyl) pyrazin-2-yl}imidodicarbonate (250 mg, 0.37 mmol) and Intermediate 22 (128 mg, 0.41 mmol) were dissolved in DCE (6 mL) and stirred at RT, under nitrogen for 1 hr. STAB (157 mg, 0.74 mmol) was added and the reaction was stirred for a further 18 hrs. The reaction was quenched by the addition of sat Na₂CO₃ (10 mL) and DCM (10 mL). The aqueous layer was separated and further extracted with DCM (3×20 mL) and the combined organics were dried over MgSO₄, filtered, concentrated in vacuo and purified by column chromatography (40% EtOAc/heptane) to give the title compound as an orange oil (252 mg, 70%).

LCMS: m/z 969/970/971 [M+H]⁺.

Stage 3: 1-tert-Butyl 2-cyclopentyl (2R)-4-[acetyl(4-{5-[bis(tert-butoxycarbonyl) amino]-6-[(tert-butoxycarbonyl)(2,6-dichlorobenzyl)amino]pyrazin-2-yl}benzyl)amino]piperidine-1,2-dicarboxylate 1-tert-Butyl 2-cyclopentyl (2R)-4-[(4-{5-[bis(tert-butoxycarbonyl)amino]-6-[(tert-butoxycarbonyl)(2,6-dichlorobenzyl)amino]pyrazin-2-yl}benzyl)amino]piperidine-1,2-dicarboxylate (134 mg, 0.14 mmol) was dissolved in anhydrous DCM (2 mL). Triethylamine (21 mg, 0.21 mmol) was added and the reaction was cooled to 0° C. After 5 minutes acetyl chloride (16 mg, 0.27 mmol) was added and the reaction was warmed slowly to RT over 3 hrs. Additional acetyl chloride (8 mg, 0.10 mmol) was added and the reaction was stirred for a further 2 hrs until completion. Sat NaHCO₃ (10 mL) and added and the product was extracted into DCM (3×20 mL). The combined organics were dried over MgSO₄, filtered, concentrated in vacuo, and purified by automated column chromatography using EtOAc in heptane (gradient 0-100%) to give the title compound as a colourless oil (107 mg, 77%).

LCMS: m/z 911/912/913/914 [M-Boc]⁺.

Stage 4: Cyclopentyl (2R)-4-[acetyl(4-{5-amino-6-[(2,6-dichlorobenzyl)amino]pyrazin-2-yl}benzyl)amino]piperidine-2-carboxylate 1-tert-Butyl 2-cyclopentyl (2R)-4-[acetyl(4-{5-[bis(tert-butoxycarbonyl)amino]-6-[(tert-butoxycarbonyl)(2,6-dichlorobenzyl)amino]pyrazin-2-yl}benzyl)amino]piperidine-1,2-dicarboxylate (107 mg, 0.11 mmol) was dissolved in diethyl ether (0.5 mL) and 2M HCl in diethyl ether (10 mL) was added. The reaction was stirred for 18 hrs until completion. The solvent was removed in vacuo to give a yellow solid, which was purified by preparative HPLC to give the title compound as an off-white solid (18 mg).

LCMS: purity 99%, m/z 611/613/615 [M+H]⁺.

¹H NMR (300 MHz, DMSO-d₆) δ ppm: 7.72-7.95 (3H, m), 7.48-7.56 (2H, m), 7.34-7.44 (1H, m), 7.16-7.27 (2H, m), 6.25 (1H, br, s), 6.01-6.13 (2H, m), 4.99-5.06 (1H, m), 4.85 (2H, d, J=4.1 Hz), 4.56 (1.6H, s), 4.35-4.48 (1H, m), 3.91 (0.4H, br, s), 3.24-3.33 (1H, m), 2.95 (1H, br, s), 2.19 (1H, br, s), 1.99 (3H, br, s), 1.68-1.81 (3H, m), 1.33-1.66 (10H, m).

Example 32

Cyclopentyl (2R)-4-[(3-{5-amino-6-[(2,6-dichlorobenzyl)amino]pyrazin-2-yl}benzoyl)amino]piperidine-2-carboxylate

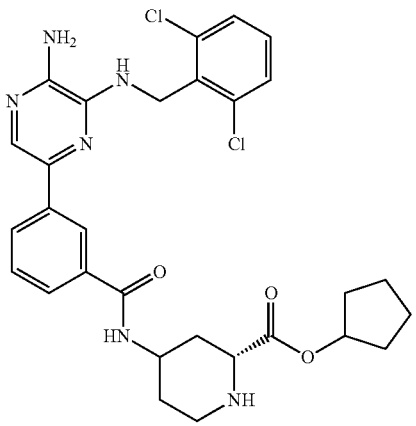 [SMILES: Nc1ncc(-c2cccc(C(=O)NC3CCN[C@@H](C(=O)OC4CCCC4)C3)c2)nc1NCc1c(Cl)cccc1Cl]

Cyclopentyl (2R)-4-[(3-{5-amino-6-[(2,6-dichlorobenzyl)amino]pyrazin-2-yl}benzoyl) amino]piperidine-2-carboxylate was synthesised by the route shown in Scheme 23 below.

Scheme 23

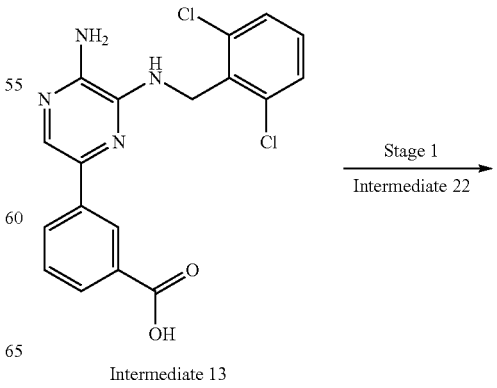

Intermediate 13

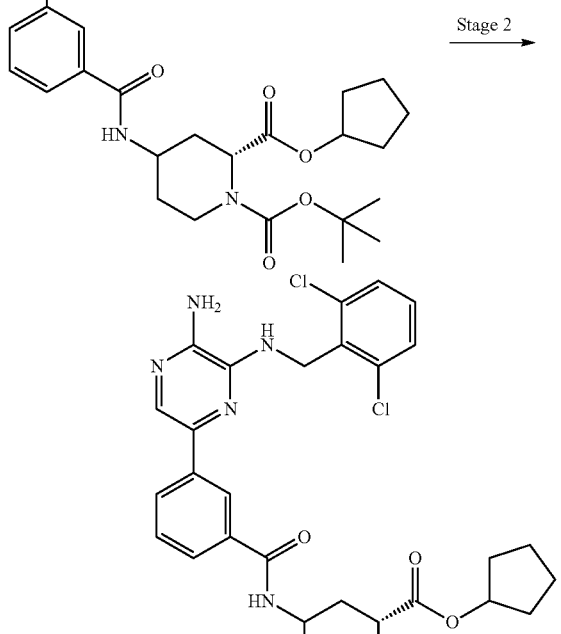

Example 32

Stage 1. 1-tert-Butyl 2-cyclopentyl (2R)-4-[(3-{5-amino-6-[(2,6-dichlorobenzyl)amino]pyrazin-2-yl}benzoyl)amino]piperidine-1,2-dicarboxylate Intermediate 13 (100 mg, 0.26 mmol) was dissolved in DMF (6 mL) and Intermediate 22 (96 mg, 0.3 mmol) was added, followed by HOBt (41 mg, 0.3 mmol) and EDC (56 mg, 0.3 mmol). The reaction mixture was stirred for 18 hrs and then concentrated in vacuo. The crude residue was taken forward unpurified (170 mg).

LCMS: m/z 683/685 [M+H]$^+$.

Stage 2. Cyclopentyl (2R)-4-[(3-{5-amino-6-[(2,6-dichlorobenzyl)amino]pyrazin-2-yl}benzoyl)amino]piperidine-2-carboxylate 1-tert-Butyl 2-cyclopentyl (2R)-4-[(3-{5-amino-6-[(2,6-dichlorobenzyl)amino]pyrazin-2-yl}benzoyl)amino]piperidine-1,2-dicarboxylate (170 mg, 0.24 mmol) was dissolved in DCM (1 mL) and 2N HCl in diethyl ether (1 mL) added. The reaction was stirred for 16 hrs and then concentrated in vacuo. The crude residue was purified by preparative HPLC to give the title compound as a yellow solid (50 mg).

LCMS: purity 97%, m/z 583/585 [M+H]$^+$.

$^1$H NMR (300 MHz, DMSO-d$_6$) δ ppm: 8.43-8.3 (2H, m), 8.09 (1H, d, J=7.8 Hz), 7.91 (1H, s), 7.72 (1H, d, J=7.8 Hz), 7.65-733 (4H, m), 6.46-6.35 (1H, m), 6.28 (2H, s), 5.18-5.05 (1H, m), 4.84 (2H, d, J=4.0 Hz), 4.05-3.83 (1H, m), 3.5-2.4 (3H, m), 2.2-2.0 (1H, m), 1.95-1.2 (12H, m).

Example 33 tert-Butyl (2R)-4-[(3-{5-amino-6-[(2,6-dichlorobenzyl)amino]pyrazin-2-yl}benzoyl)amino]piperidine-2-carboxylate

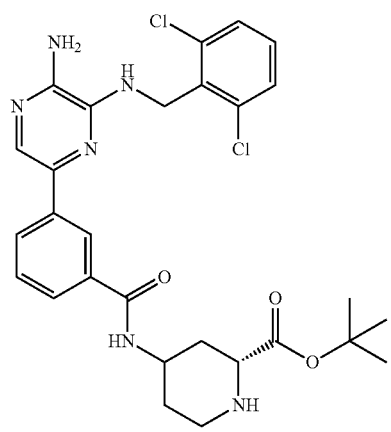 [SMILES: CC(C)(C)OC(=O)[C@H]1CC(NC(=O)c2cccc(-c3cnc(N)c(NCc4c(Cl)cccc4Cl)n3)c2)CCN1]

tert-Butyl (2R)-4-[(3-{5-amino-6-[(2,6-dichlorobenzyl)amino]pyrazin-2-yl}benzoyl) amino]piperidine-2-carboxylate was synthesised in a similar manner to Example 32 above using Intermediate 25 at Stage 1 of Scheme 23.

LCMS: purity 97%, m/z 571/573 [M+H]$^+$.

$^1$H NMR (300 MHz, DMSO-d$_6$) δ ppm: 8.35 (2H, m), 8.09 (1H, d, J=7.9 Hz), 7.91 (1H, s), 7.72 (1H, d, J=7.9 Hz), 7.60-7.34 (4H, m), 6.46-6.34 (1H, m), 6.28 (2H, s), 4.84 (2H, d, J=4.1 Hz), 4.05-3.95 (1H, m) 3.3-2.4 (3H, m), 2.1-2.0 (2H, m), 1.7-1.6 (1H, m), 1.4 (9H, s) 1.45-1.25 (2H, m).

Example 34

Cyclopentyl (2R)-4-[(3-{5-amino-6-[(2,6-dichlorobenzyl)amino]pyrazin-2-yl}benzyl)amino]piperidine-2-carboxylate

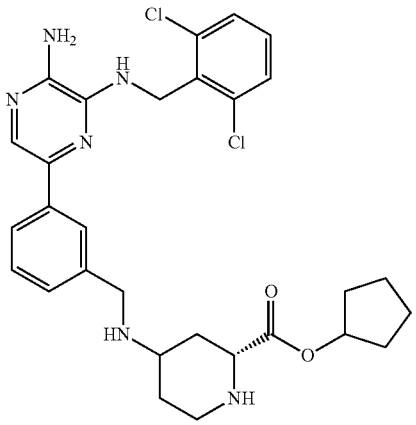 [SMILES: Nc1ncc(-c2cccc(CNC3CCN[C@@H](C(=O)OC4CCCC4)C3)c2)nc1NCc1c(Cl)cccc1Cl]

Cyclopentyl (2R)-4-[(3-{5-amino-6-[(2,6-dichlorobenzyl)amino]pyrazin-2-yl}benzyl) amino]piperidine-2-carboxylate was synthesised by the route shown in Scheme 24 below.

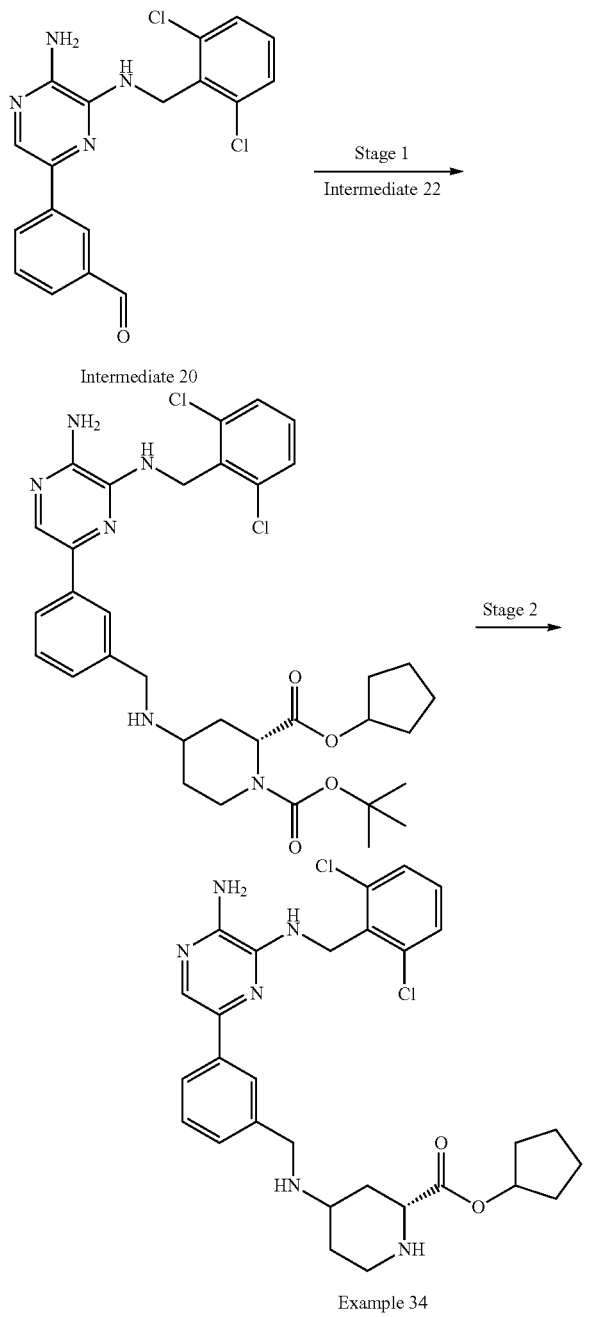

Scheme 24

Intermediate 20

Stage 1
Intermediate 22

Example 34

Stage 1. 1-tert-Butyl 2-cyclopentyl (2R)-4-[(3-{5-amino-6-[(2,6-dichlorobenzyl)amino]pyrazin-2-yl}benzyl)amino]piperidine-1,2-dicarboxylate Intermediate 20 (78 mg, 0.2 mmol) was suspended in DCE (6 mL) and Intermediate 22 (97 mg, 0.31 mmol) added. The reaction mixture was stirred for 10 mins before addition of STAB (85 mg, 0.4 mmol). The reaction mixture was allowed to stir at RT for 72 hrs before addition of sat NaHCO$_3$ (100 mL) and extraction of the product with DCM (3×30 mL). The combined organic layers were separated and dried over Na$_2$SO$_4$, filtered and concentrated in vacuo. Purification by automated column chromatography (EtOAc/DCM) gave the product (115 mg) which still contained minor impurity but was taken forward to Stage 2.

LCMS: m/z 669/671 [M+H]$^+$.

Stage 2. Cyclopentyl (2R)-4-[(3-{5-amino-6-[(2,6-dichlorobenzyl)amino]pyrazin-2-yl}benzyl)amino]piperidine-2-carboxylate 1-tert-Butyl 2-cyclopentyl (2R)-4-[(3-{5-amino-6-[(2,6-dichlorobenzyl)amino]pyrazin-2-yl}benzyl)amino]piperidine-1,2-dicarboxylate (115 mg, 0.17 mmol) was dissolved in DCM (1 mL) and 2N HCl in diethyl ether added. The reaction mixture was stirred at RT for 18 hrs and then concentrated in vacuo. The crude residue was purified by preparative HPLC to give the title compound as an off-white solid (29 mg).

LCMS: purity 97%, m/z 569/571 [M+H]$^+$.

$^1$H NMR (300 MHz, DMSO-d$_6$) δ ppm: 7.85-7.6 (3H, m), 7.5-7.0 (5H, m), 6.32-6.23 (1H, m), 6.11 (2H, s), 5.1-4.9 (1H, m), 4.8-4.7 (2H, m), 3.7 (2H, s), 3.15-2.9 (2H, m), 2.4-2.3 (1H, m), 2.1-1.9 (3H, m), 1.85-1.65 (3H, m), 1.62-1.35 (7H, m), 1.1-0.9 (2H, m).

Example 35

Cyclopentyl (2S)-4-[(3-{5-amino-6-[(2,6-dichlorobenzyl)amino]pyrazin-2-yl}benzyl)amino]piperidine-2-carboxylate di-formate

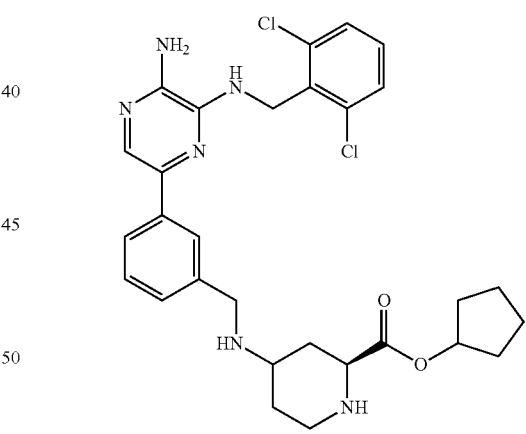

Cyclopentyl (2S)-4-[(3-{5-amino-6-[(2,6-dichlorobenzyl)amino]pyrazin-2-yl}benzyl) amino]piperidine-2-carboxylate was synthesised in a similar manner to Example 34 using Intermediate 22 in Stage 1 of the synthetic route shown in Scheme 24. Purification of the final compound was carried out by preparative HPLC to afford the di-formate salt of the title compound as a white solid (18.0 mg, 18%).

$^1$H NMR (300 MHz, DMSO-d$_6$) δ ppm 8.23 (2H, s), 7.90 (1H, s), 7.85-7.78 (2H, m), 7.58-7.5 (2H, m), 7.48-7.2 (3H, m), 6.39-6.3 (1H, s), 6.20 (2H, s), 5.15-5.0 (1H, m), 4.83 (2H, d, J=4.1 Hz), 3.83 (2H, s), 3.5-2.8 (2H, m), 2.7-2.0 (3H, m), 1.9-1.4 (11H, m), 1.25-1.0 (2H, m)

LCMS: purity 98%, m/z 569/571 [M+H]$^+$.

Example 36

Cyclopentyl (2S)-4-(3-{5-amino-6-[(2,6-dichlorobenzyl)amino]pyrazin-2-yl}benzyl)piperazine-2-carboxylate

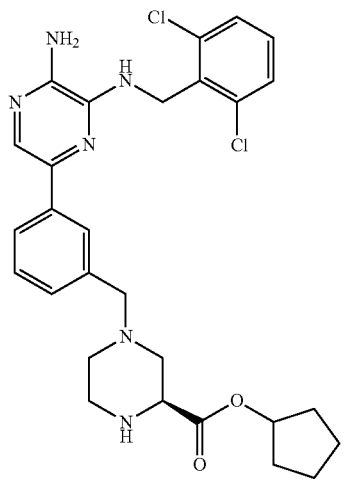 [SMILES: Nc1ncc(-c2cccc(CN3CCN[C@H](C(=O)OC4CCCC4)C3)c2)nc1NCc1c(Cl)cccc1Cl]

Cyclopentyl (2S)-4-(3-{5-amino-6-[(2,6-dichlorobenzyl)amino]pyrazin-2-yl}benzyl) piperazine-2-carboxylate was synthesised in a similar manner to Example 34 using Intermediate 29 and DCM as solvent at Stage 1 in the route shown in Scheme 24.

LCMS: purity 93%, m/z 555/557/559 [M+H]$^+$.

$^1$H NMR (300 MHz, CD$_3$OD) δ ppm: 7.93 (1H, s), 7.83 (1H, d, J=7.9 Hz), 7.71 (1H, s), 7.40-7.46 (2H, m), 7.27-7.39 (2H, m), 7.20-7.27 (1H, m), 5.13-5.21 (1H, m), 5.03 (2H, s), 3.66-3.72 (1H, m), 3.53-3.66 (2H, m), 3.14-3.24 (1H, m), 2.86-2.97 (2H, m), 2.63-2.73 (1H, m), 2.57 (1H, dd, J=11.2, 8.0 Hz), 2.41-2.51 (1H, m), 1.71-1.90 (2H, m), 1.67 (1H, dd, J=6.8, 2.1 Hz), 1.44-1.64 (5H, m).

Example 37

Cyclopentyl (2R)-4-(3-{5-amino-6-[(2,6-dichlorobenzyl)amino]pyrazin-2-yl}benzyl)piperazine-2-carboxylate

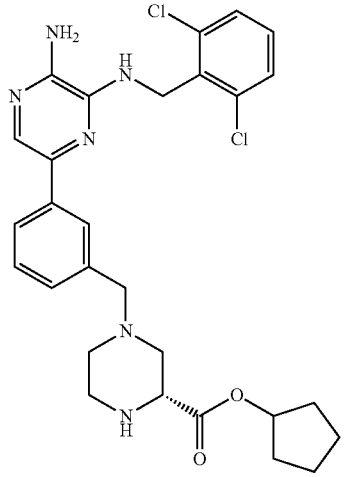 [SMILES: Nc1ncc(-c2cccc(CN3CCN[C@@H](C(=O)OC4CCCC4)C3)c2)nc1NCc1c(Cl)cccc1Cl]

Cyclopentyl (2R)-4-(3-{5-amino-6-[(2,6-dichlorobenzyl)amino]pyrazin-2-yl}benzyl) piperazine-2-carboxylate was synthesised in a similar manner to Example 34 using Intermediate 30 and DCM as solvent at Stage 1 in the route shown in Scheme 24. LCMS: purity 100%, m/z 555/557/559 [M+H]$^+$.

$^1$H NMR (300 MHz, CD$_3$OD) δ ppm: 7.92 (1H, s), 7.82 (1H, d, J=7.9 Hz), 7.71 (1H, s), 7.39-7.48 (2H, m), 7.20-7.38 (3H, m), 5.14 (1H, t, J=5.8 Hz), 5.02 (2H, s), 3.50-3.67 (3H, m), 3.05-3.15 (1H, m), 2.77-2.92 (2H, m), 2.58-2.68 (1H, m), 2.33-2.53 (2H, m), 1.71-1.89 (2H, m), 1.47-1.70 (6H, m).

Example 38

Cyclopentyl N-(3-{5-amino-6-[(2,6-dichlorobenzyl)amino]pyrazin-2-yl}benzyl)-L-leucinate

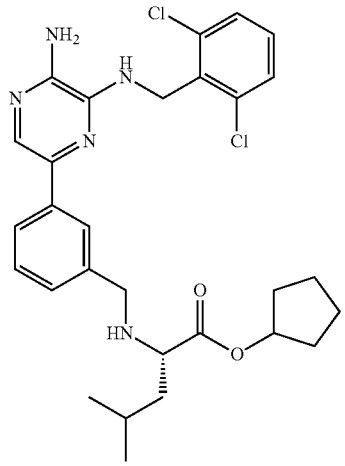 [SMILES: CC(C)C[C@H](NCc1cccc(-c2cnc(N)c(NCc3c(Cl)cccc3Cl)n2)c1)C(=O)OC1CCCC1]

Cyclopentyl N-(3-{5-amino-6-[(2,6-dichlorobenzyl)amino]pyrazin-2-yl}benzyl)-L-leucinate was prepared in a similar manner to Example 34 following Stage 1 of the route shown in Scheme 24 using Intermediate 32.

LCMS: purity 95%, m/z 556/558 [M+H]$^+$.

$^1$H NMR (300 MHz, CDCl$_3$) δ ppm: 7.91-7.80 (2H, m), 7.81-7.78 (1H, m), 7.6-7.05 (5H, m), 5.22-5.10 (1H, m), 4.96 (2H, d, J=5.7 Hz), 4.38-4.22 (1H, m), 4.09 (2H, s), 3.81 (1H, d, J=13.0 Hz), 3.61 (1H, d, J=13.0 Hz), 3.21 (1H, t, J=7.3 Hz), 1.9-1.3 (12H, m), 0.83 (3H, d, J=2.2 Hz), 0.78 (3H, d, J=2.2 Hz).

Example 39 tert-Butyl N-(3-{5-amino-6-[(2,6-dichlorobenzyl)amino]pyrazin-2-yl}benzyl)-L-leucinate

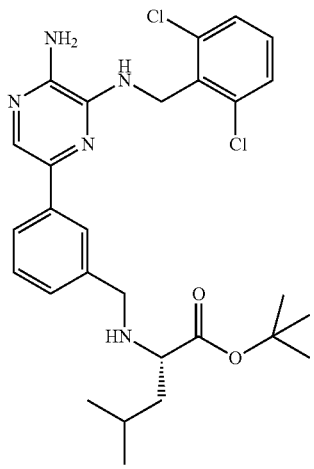 [SMILES: CC(C)C[C@H](NCc1cccc(-c2cnc(N)c(NCc3c(Cl)cccc3Cl)n2)c1)C(=O)OC(C)(C)C]

tert-Butyl N-(3-{5-amino-6-[(2,6-dichlorobenzyl)amino]pyrazin-2-yl}benzyl)-L-leucinate was prepared in a similar manner to Example 34 following Stage 1 of the route shown in Scheme 24 and using tert-butyl L-leucinate.

LCMS: purity 92%, m/z 544/546 [M+H]+.

1H NMR (300 MHz, CDCl3) δ ppm: 8.05-7.85 (3H, m), 7.45-7.15 (5H, m), 5.06 (2H, d, J=1.8 Hz), 4.5-4.4 (1H, m), 4.19 (2H, s), 3.92 (1H, d, J=5.7 Hz), 3.72 (1H, d, J=5.7 Hz), 3.3-3.2 (1H, m), 1.9-1.8 (1H, m), 1.7-1.45 (3H, m), 1.58 (s, 9H), 0.94 (3H, d, J=2.2 Hz), 0.88 (3H, d, J=2.2 Hz).

Example 40

Cyclopentyl N-(3-{5-amino-6-[(2,6-dichlorobenzyl)amino]pyrazin-2-yl}benzyl)-2-methylalaninate

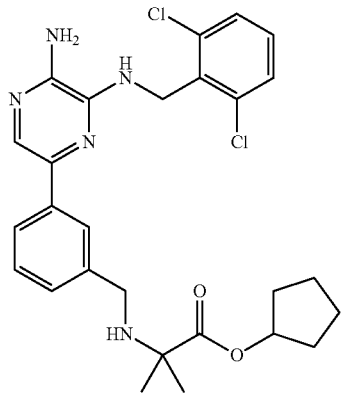 [SMILES: CC(C)(NCc1cccc(-c2cnc(N)c(NCc3c(Cl)cccc3Cl)n2)c1)C(=O)OC1CCCC1]

Cyclopentyl N-(3-{5-amino-6-[(2,6-dichlorobenzyl)amino]pyrazin-2-yl}benzyl)-2-methylalaninate was prepared in a similar manner to Example 34 following Stage 1 of the route shown in Scheme 24 and using Intermediate 33 (free base) and with final purification by preparative HPLC.

LCMS: purity 97%, m/z 528/530 [M+H]+.

1H NMR (300 MHz, DMSO-d6) δ ppm: 7.86 (1H, s), 7.82-7.70 (2H, m), 7.6-7.5 (2H, m), 7.46-7.25 (3H, m), 6.4-6.3 (1H, m), 6.20 (2H, s), 5.3-5.0 (1H, m), 4.83 (2H, d, J=4.0 Hz), 3.60 (2H, s), 2.39-2.15 (1H, m), 1.94-1.4 (8H, m), 1.25 (6H, s).

Example 41 tert-Butyl N-(3-{5-amino-6-[(2,6-dichlorobenzyl)amino]pyrazin-2-yl}benzyl)-2-methylalaninate formate salt

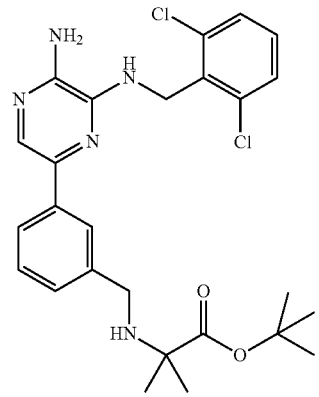 [SMILES: CC(C)(C)OC(=O)C(C)(C)NCc1cccc(-c2cnc(N)c(NCc3c(Cl)cccc3Cl)n2)c1]

tert-Butyl N-(3-{5-amino-6-[(2,6-dichlorobenzyl)amino]pyrazin-2-yl}benzyl)-2-methylalaninate was prepared in a similar manner to Example 34 following Stage 1 of the route shown in Scheme 24 and using alpha-aminoisobutyric acid tert-butyl ester and with final purification by preparative HPLC to give the formate salt of the title compound.

LCMS: purity 98%, m/z 516/518 [M+H]+.

1H NMR (300 MHz, DMSO-d6) δ ppm: 8.30 (1H, br s), 7.95-7.86 (1H, m), 7.85-7.6 (2H, m), 7.62-7.47 (2H, m), 7.45-7.1 (3H, m), 6.40-6.30 (1H, m), 6.3-6.2 (2H, m), 4.9-4.8 (2H, m), 3.7-3.58 (2H, m), 3.4-3.1 (1H, NH not visible under water peak), 1.42 (9H, s), 1.23 (6H, s).

Example 42

Cyclopentyl 1-[(3-{5-amino-6-[(2,6-dichlorobenzyl)amino]pyrazin-2-yl}benzyl)amino]cyclobutanecarboxylate di-formate

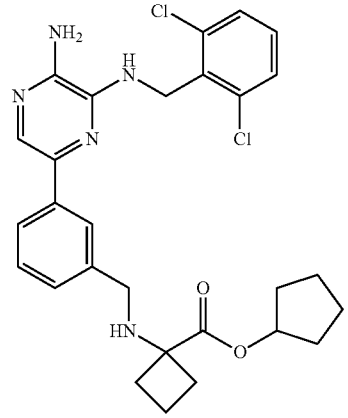 [SMILES: Nc1ncc(-c2cccc(CNC3(C(=O)OC4CCCC4)CCC3)c2)nc1NCc1c(Cl)cccc1Cl]

Cyclopentyl 1-[(3-{5-amino-6-[(2,6-dichlorobenzyl)amino]pyrazin-2-yl}benzyl)amino]cyclobutanecarboxylate was prepared in a similar manner to Example 34 following Stage 1 of the route shown in Scheme 18 and using Intermediate 34 (free base). The final compound was purified by preparative HPLC to afford the title compound as the di-formate salt.

LCMS: purity 98%, m/z 540/541/542 [M+H]+.

1H NMR (300 MHz, DMSO-d6) δ ppm: 8.30 (2H, br, s), 7.88 (1H, s), 7.82-7.75 (2H, m), 7.6-7.5 (2H, m), 7.46-7.17 (3H, m), 6.42-6.3 (1H, m), 6.21 (2H, s), 5.15-5.0 (1H, m), 4.83 (2H, d, J=4.1 Hz), 3.55 (2H, s), 2.35-2.15 (2H, m), 2.1-1.4 (13H, m).

Example 43

Cyclopentyl N-(3-{5-amino-6-[(2,6-dichlorobenzyl)amino]pyrazin-2-yl}benzyl)-O-tert-butyl-L-serinate

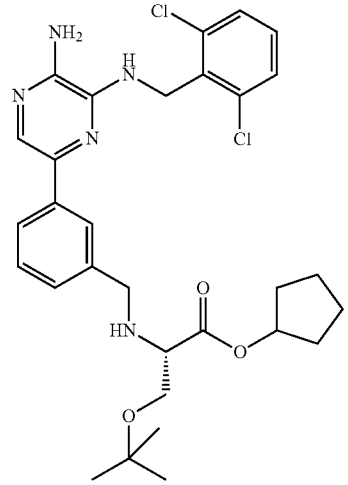 [SMILES: CC(C)(C)OC[C@H](NCc1cccc(-c2cnc(N)c(NCc3c(Cl)cccc3Cl)n2)c1)C(=O)OC1CCCC1]

Cyclopentyl N-(3-{5-amino-6-[(2,6-dichlorobenzyl)amino]pyrazin-2-yl}benzyl)-O-tert-butyl-L-serinate was prepared in a similar manner to Example 34 following Stage 1 of the route shown in Scheme 24 and using Intermediate 35 (free base). The final purification was done by preparative HPLC.

LCMS: purity 98%, m/z 586/588 [M+H]$^+$.

$^1$H NMR (300 MHz, DMSO-d$_6$) δ ppm: 7.88 (1H, s), 7.82-7.74 (2H, m), 7.6-7.5 (2H, m), 7.46-7.1 (3H, m), 6.43-6.3 (1H, m), 6.21 (2H, b, s), 5.2-5.0 (1H, m), 4.83 (2H, d, J=1.3 Hz), 3.9-3.15 (5H, m), 2.45-2.25 (1H, m), 1.9-1.4 (8H, m), 1.04 (9H, s).

Example 44 tert-Butyl N-(3-{5-amino-6-[(2,6-dichlorobenzyl)amino]pyrazin-2-yl}benzyl)-O-tert-butyl-L-serinate

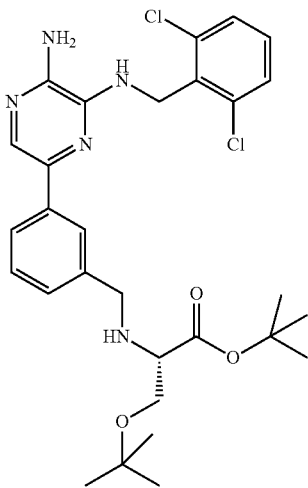 [SMILES: CC(C)(C)OC[C@H](NCc1cccc(-c2cnc(N)c(NCc3c(Cl)cccc3Cl)n2)c1)C(=O)OC(C)(C)C]

tert-Butyl N-(3-{5-amino-6-[(2,6-dichlorobenzyl)amino]pyrazin-2-yl}benzyl)-O-tert-butyl-L-serinate was prepared in a similar manner to Example 34 following Stage 1 of the route shown in Scheme 24 and using tert-butyl O-tert-butyl-L-serinate hydrochloride. The final purification was carried out by preparative HPLC.

LCMS: purity 98%, m/z 574/576 [M+H]$^+$.

$^1$H NMR (300 MHz, DMSO-d$_6$) δ ppm: 7.89 (1H, s), 7.84-7.72 (2H, m), 7.62-7.47 (2H, m), 7.45-7.12 (3H, m), 6.42-6.3 (1H, m), 6.21 (2H, s), 4.9-4.77 (2H, m), 3.83 (1H, d, J=4.4 Hz), 3.64 (1H, d, J=4.4 Hz), 3.55-3.0 (3H, m), 2.42-2.2 (1H, m), 1.39 (9H, s), 1.05 (9H, s)

Example 45 tert-Butyl N-(3-{5-amino-6-[(2,6-dichlorobenzyl)amino]pyrazin-2-yl}benzyl)-L-alaninate

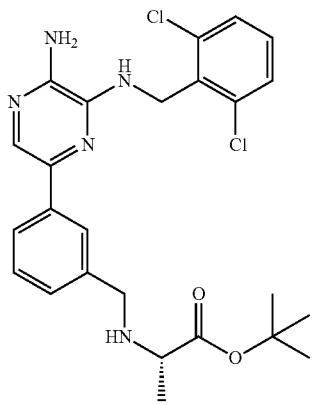 [SMILES: C[C@H](NCc1cccc(-c2cnc(N)c(NCc3c(Cl)cccc3Cl)n2)c1)C(=O)OC(C)(C)C]

tert-Butyl N-(3-{5-amino-6-[(2,6-dichlorobenzyl)amino]pyrazin-2-yl}benzyl)-L-alaninate was prepared in a similar manner to Example 34 according to Stage 1 of the route shown in Scheme 24 and using tert-butyl L-alaninate (free base) as the amino acid.

LCMS: purity 95%, m/z 502/504 [M+H]$^+$.

$^1$H NMR (300 MHz, DMSO-d$_6$) δ ppm: 7.89-7.82 (1H, m), 7.81-7.7 (2H, m), 7.59-7.48 (2H, m), 7.46-7.1 (3H, m), 6.4-6.3 (1H, m), 6.20 (2H, br, s), 4.88-4.80 (2H, m), 3.86-3.5 (2H, m), 3.45-3.0 (1H, m), 2.45-2.2 (1H, m), 1.41 (9H, s), 1.16 (3H, d, J=2.2 Hz).

Example 46 tert-Butyl (2R)-4-[(3-{5-amino-6-[(2,6-dichlorobenzyl)amino]pyrazin-2-yl}benzyl)amino]piperidine-2-carboxylate

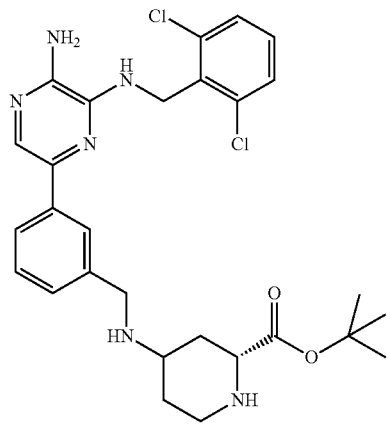 [SMILES: CC(C)(C)OC(=O)[C@H]1CC(NCc2cccc(-c3cnc(N)c(NCc4c(Cl)cccc4Cl)n3)c2)CCN1]

tert-Butyl (2R)-4-[(3-{5-amino-6-[(2,6-dichlorobenzyl)amino]pyrazin-2-yl}benzyl) amino]piperidine-2-carboxylate was synthesised as shown in Scheme 25.

Scheme 25

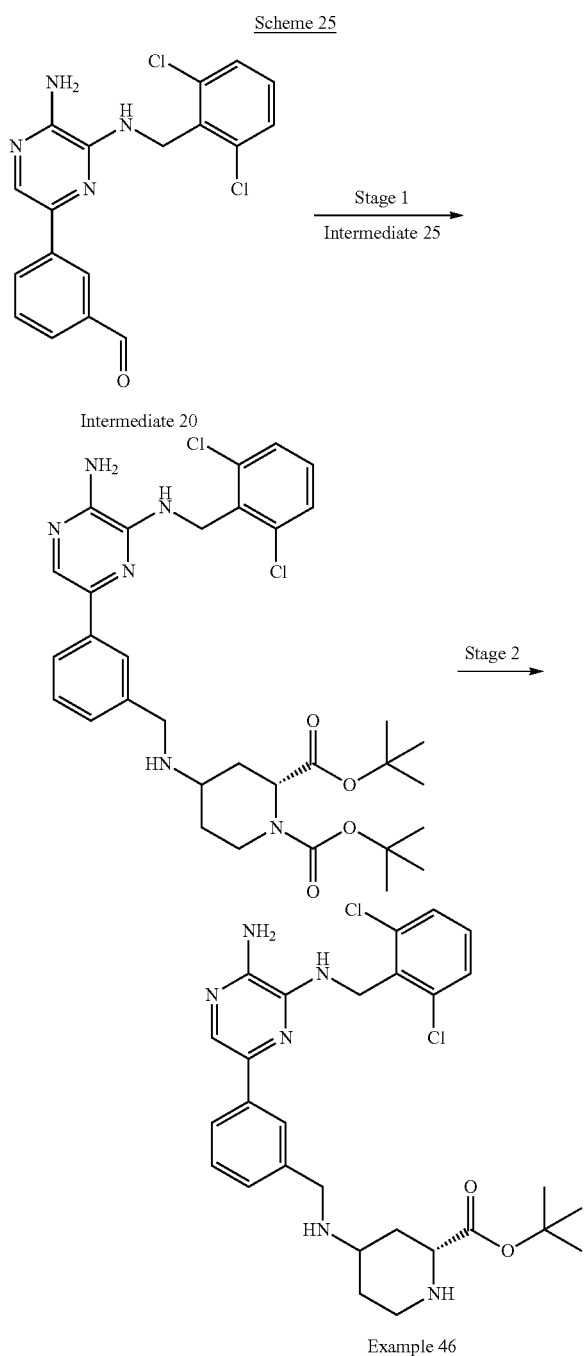

Example 46

Stage 1. Di-tert-butyl (2R)-4-[(3-{5-amino-6-[(2,6-dichlorobenzyl)amino]pyrazin-2-yl}benzyl)amino]piperidine-1,2-dicarboxylate Intermediate 20 (90 mg, 0.24 mmol) was suspended in DCE (4 mL) and Intermediate 25 (108 mg, 0.36 mmol) added. The reaction mixture was stirred for 10 mins before addition of STAB (101 mg, 0.48 mmol). The reaction mixture was allowed to stir at RT for 18 hrs before addition of sat NaHCO₃ (120 mL) and extraction of the product with DCM (2×60 mL). The combined organic layers were separated and dried over Na₂SO₄, filtered and concentrated in vacuo. Purification by automated column chromatography (EtOAc/DCM) gave the product (130 mg, 82%).

LCMS: m/z 657/659 [M+H]⁺.

Stage 2. tert-Butyl (2R)-4-[(3-{5-amino-6-[(2,6-dichlorobenzyl)amino]pyrazin-2-yl}benzyl)amino]piperidine-2-carboxylate Di-tert-butyl (2R)-4-[(3-{5-amino-6-[(2,6-dichlorobenzyl)amino]pyrazin-2-yl}benzyl) amino]piperidine-1,2-dicarboxylate (130 mg, 0.197 mmol) was dissolved in dioxane (3 mL) and cooled to 0° C. before the dropwise addition of 4M HCl in dioxane (1 mL). Over the course of 6 hours at 0° C., an additional 2.5 mL of 4M HCL in dioxane was added for complete reaction. To the reaction mixture was added 2N NaOH (80 mL) and the product extracted with EtOAc (3×50 mL). The combined organic layers were separated and dried over Na₂SO₄, filtered and concentrated in vacuo. The crude residue was purified by preparative HPLC to give the title compound as an orange solid (44 mg).

LCMS: purity 97%, m/z 557/559 [M+H]⁺.

¹H NMR (300 MHz, DMSO-d₆) δ ppm: 7.88 (1H, s), 7.85-7.8 (2H, m), 7.62-7.5 (2H, m), 7.47-7.15 (3H, m), 6.40-6.3 (1H, m), 6.18 (2H, s), 4.83 (2H, d, J=4.1 Hz), 3.78 (2H, s), 3.5-3.25 (2H, m), 3.11-2.88 (1H, m), 2.55-1.75 (5H, m), 1.38 (9H, s), 1.15-0.9 (2H, m).

Example 47 tert-Butyl (2S)-4-[(3-{5-amino-6-[(2,6-dichlorobenzyl)amino]pyrazin-2-yl}benzyl)amino]piperidine-2-carboxylate di-formate

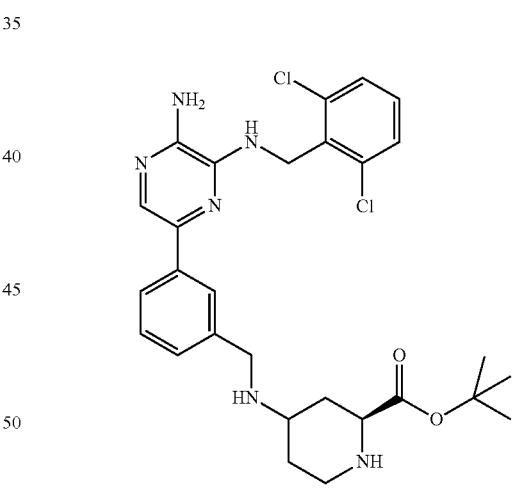

tert-Butyl (2S)-4-[(3-{5-amino-6-[(2,6-dichlorobenzyl)amino]pyrazin-2-yl}benzyl) amino]piperidine-2-carboxylate was synthesised in a similar manner to Example 46 using with Intermediate 26 in Stage 1 of the synthetic route shown in Scheme 25. Purification of the final compound was carried out by preparative HPLC to afford the di-formate salt of the title compound as a white solid (19.8 mg, 8%).

LCMS: purity 96%, m/z 557/559 [M+H]⁺

¹H NMR (300 MHz, DMSO-d₆) δ ppm: 8.27 (2H, br, s), 7.9 (1H, s), 7.85-7.7 (2H, m), 7.7-7.47 (2H, m), 7.45-7.15 (3H, m), 6.4-6.3 (1H, m), 6.19 (2H, s), 4.88-4.75 (2H, m), 3.80 (2H, m), 3.75-3.2 (2H, m), 3.17-2.8 (2H, m), 2.65-2.3 (2H, m), 2.2-1.7 (2H, m), 1.38 (9H, s), 1.2-0.9 (2H, m).

Example 48

Cyclopentyl N-[2-(3-{5-amino-6-[(2,6-dichlorobenzyl)amino]pyrazin-2-yl}phenyl)ethyl]-2-methylalaninate

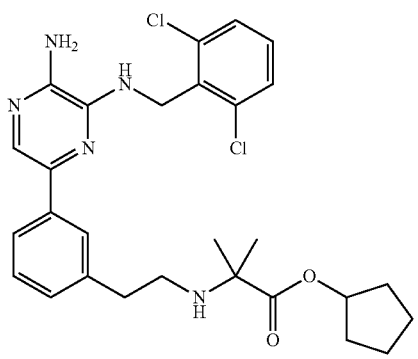 [SMILES: CC(C)(NCCc1cccc(-c2cnc(N)c(NCc3c(Cl)cccc3Cl)n2)c1)C(=O)OC1CCCC1]

Cyclopentyl N-[2-(3-{5-amino-6-[(2,6-dichlorobenzyl)amino]pyrazin-2-yl}phenyl)ethyl]-2-methylalaninate was synthesised as shown in Scheme 26 below.

Scheme 26

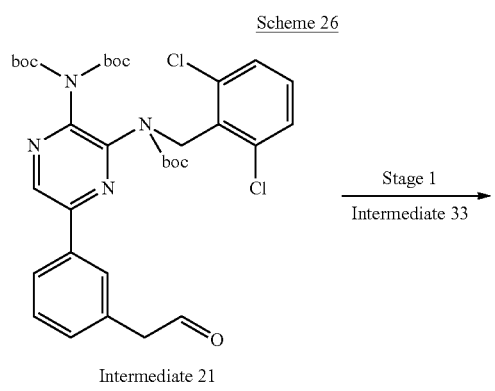

Intermediate 21

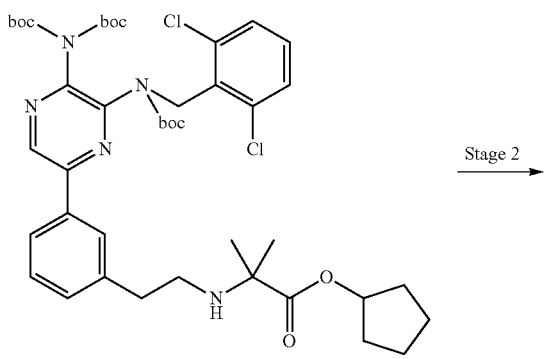

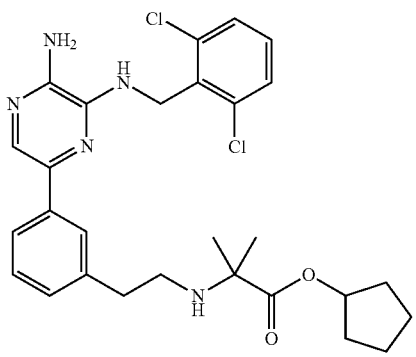

Example 48

Stage 1: Cyclopentyl N-[2-(3-{5-[bis(tert-butoxycarbonyl)amino]-6-[(tert-butoxy carbonyl)(2,6-dichlorobenzyl)amino]pyrazin-2-yl}phenyl)ethyl]-2-methylalaninate Intermediate 21 (168 mg, 0.24 mmol) and Intermediate 33 (free base) (125 mg, 0.73 mmol) were dissolved in DCE (4 mL) and stirred at RT for 10 mins under nitrogen. STAB (104 mg, 0.49 mmol) was added and the reaction was stirred for a further 18 hrs. The reaction was quenched by the addition of sat NaHCO₃ (15 mL). The aqueous layer was separated and further extracted with DCM (3×20 mL) and the combined organics were dried over MgSO₄, filtered, concentrated in vacuo and purified by column chromatography (50% EtOAc/heptane) to give the title compound as an orange oil (64 mg, 31%).

LCMS: m/z 842/844/846 [M+H]⁺.

Stage 2: Cyclopentyl N-[2-(3-{5-amino-6-[(2,6-dichlorobenzyl)amino]pyrazin-2-yl}phenyl)ethyl]-2-methylalaninate Cyclopentyl N-[2-(3-{5-[bis(tert-butoxycarbonyl)amino]-6-[(tert-butoxy carbonyl)(2,6-dichlorobenzyl)amino]pyrazin-2-yl}phenyl)ethyl]-2-methylalaninate (64 mg, 0.076 mmol) was stirred in 2M HCl in diethyl ether (5 mL) was added. The reaction was stirred for 18 hrs. 4M HCl in dioxane (2 mL) was added and the reaction was stirred for 30 mins for complete reaction. The solvent was removed in vacuo to give a yellow solid which was purified by preparative HPLC to give the title compound as an off-white solid (15 mg, 36%).

LCMS: purity 100%, m/z 542/544/546 [M+H]⁺.

¹H NMR (300 MHz, DMSO-d₆) δ ppm: 7.69-7.82 (3H, m), 7.50-7.57 (2H, m), 7.36-7.45 (1H, m), 7.28 (1H, t, J=7.5 Hz), 7.07 (1H, d, J=7.2 Hz), 6.35 (1H, br. s), 6.19 (2H, s), 4.98 (1H, t, J=5.5 Hz), 4.83 (2H, d, J=3.8 Hz), 2.60-2.77 (4H, m), 1.91 (1H, br. s), 1.63-1.78 (2H, m), 1.36-1.61 (6H, m), 1.15 (6H, s).

Example 49

Cyclopentyl 1-{[2-(3-{5-amino-6-[(2,6-dichlorobenzyl)amino]pyrazin-2-yl}phenyl)ethyl]amino}cyclobutanecarboxylate

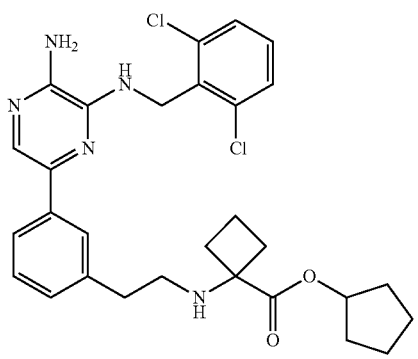 [SMILES: Nc1ncc(-c2cccc(CCNC3(C(=O)OC4CCCC4)CCC3)c2)nc1NCc1c(Cl)cccc1Cl]

Cyclopentyl 1-{[2-(3-{5-amino-6-[(2,6-dichlorobenzyl)amino]pyrazin-2-yl}phenyl)ethyl]amino}cyclobutanecarboxylate was synthesised in a similar manner to Example 48 using 1.5 equivalents of Intermediate 34 in stage 1 of the synthetic route shown in Scheme 26.

LCMS: purity 100%, m/z 554/556/558 [M+H]$^+$.

$^1$H NMR (300 MHz, DMSO-d$_6$) δ ppm: 7.69-7.82 (3H, m), 7.50-7.58 (2H, m), 7.35-7.44 (1H, m), 7.28 (1H, t, J=7.6 Hz), 7.08 (1H, d, J=7.5 Hz), 6.32-6.40 (1H, m), 6.19 (2H, s), 5.02 (1H, t, J=5.8 Hz), 4.83 (2H, d, J=4.1 Hz), 2.68-2.79 (2H, m), 2.59 (2H, br, s), 2.16-2.27 (2H, m), 2.12 (1H, br, s), 1.81-1.96 (3H, m), 1.6-1.79 (3H, m), 1.38-1.60 (6H, m).

Example 50

Cyclopentyl (2R)-4-{[2-(3-{5-amino-6-[(2,6-dichlorobenzyl)amino]pyrazin-2-yl}phenyl)ethyl]amino}piperidine-2-carboxylate

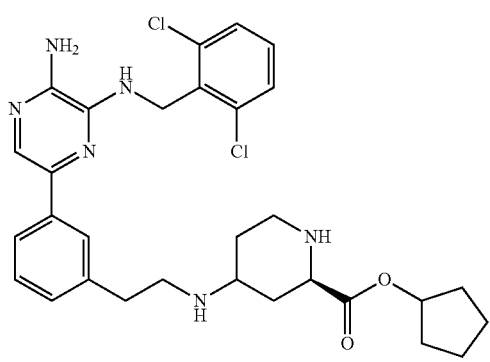 [SMILES: Nc1ncc(-c2cccc(CCNC3CCN[C@@H](C(=O)OC4CCCC4)C3)c2)nc1NCc1c(Cl)cccc1Cl]

Cyclopentyl (2R)-4-{[2-(3-{5-amino-6-[(2,6-dichlorobenzyl)amino]pyrazin-2-yl}phenyl)ethyl]amino}piperidine-2-carboxylate was synthesised according to the route shown in Scheme 27.

Scheme 27

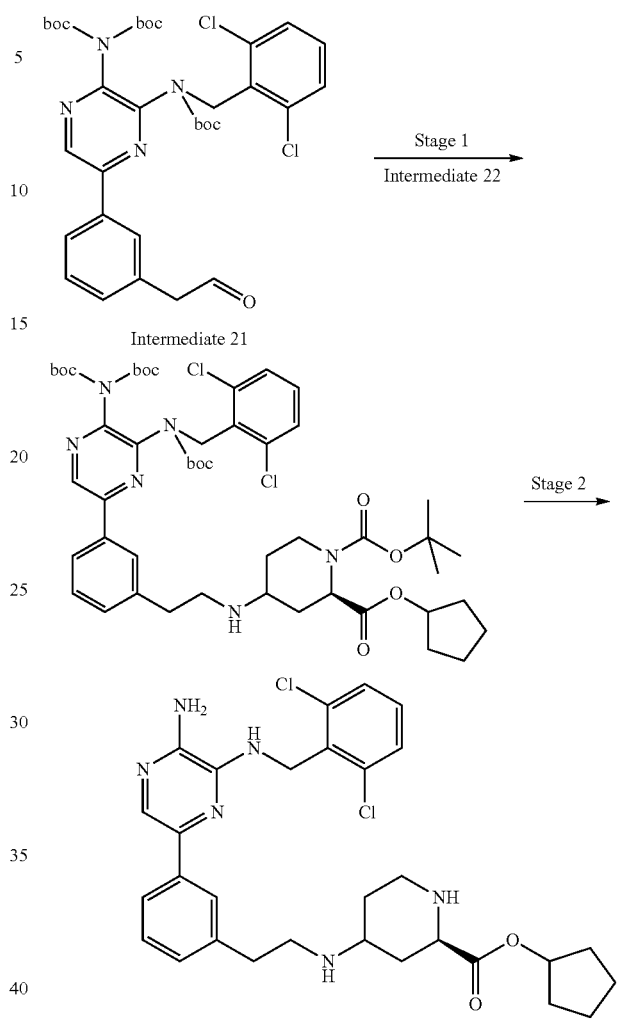

Stage 1. 1-tert-Butyl 2-cyclopentyl (2R)-4-{[2-(3-{5-[bis(tert-butoxycarbonyl)amino]-6-[(tert-butoxycarbonyl)(2,6-dichlorobenzyl)amino]pyrazin-2-yl}phenyl)ethyl]amino}piperidine-1,2-dicarboxylate Intermediate 21 (160 mg, 0.23 mmol), Intermediate 22 (109 mg, 0.35 mmol) and acetic acid (99 μL, 1.7 mmol) were dissolved in DCE (4 mL) and stirred at RT under nitrogen for 40 mins. STAB (99 mg, 0.47 mmol) and acetic acid (0.2 mL, 3.5 mmol) were added and the reaction was stirred for a further 18 hrs. The reaction was quenched by the addition of sat NaHCO$_3$ (10 mL) and DCM (20 mL). The aqueous layer was separated and further extracted with DCM (3×10 mL) and the combined organics were dried over MgSO$_4$, filtered, concentrated in vacuo and purified by automated column chromatography using EtOAc in heptane (gradient 0-50%) followed by column chromatography (40-50% EtOAc/heptane) to give the title compound as a colourless oil (103 mg, 45%).

LCMS: m/z 983/985/987 [M+H]$^+$.

Stage 2. Cyclopentyl (2R)-4-{[2-(3-{5-amino-6-[(2,6-dichlorobenzyl)amino]pyrazin-2-yl}phenyl)ethyl]amino}piperidine-2-carboxylate To a solution of 1-tert-butyl 2-cyclopentyl (2R)-4-{[2-(3-{5-[bis(tert-butoxycarbonyl) amino]-6-[(tert-butoxycarbonyl)(2,6-dichlorobenzyl)amino]pyrazin-2-yl}phenyl)ethyl]amino}piperidine-1,2-dicarboxylate (100 mg, 0.10 mmol) in dioxane (2 mL) was added 4M HCl in dioxane (3 mL) and the reaction was stirred at RT for 21 hrs. The solvent was concentrated in vacuo and the resulting residue was purified by preparative HPLC to give the title compound as a pale orange oil (10 mg, 17%). LCMS: purity 95.6%, m/z 583/585/587 [M+H]+.

1H NMR (300 MHz, DMSO): δ ppm: 7.70-7.81 (3H, m), 7.50-7.58 (2H, m), 7.35-7.44 (1H, m), 7.28 (1H, t, J=7.5 Hz), 7.10 (1H, d, J=7.5 Hz), 6.36 (1H, t, J=4.2 Hz), 6.18 (2H, s), 5.01-5.10 (1H, m), 4.83 (2H, d, J=4.1 Hz), 3.14 (1H, dd, J=11.4, 2.5 Hz), 2.94 (1H, dt, J=12.6, 3.2 Hz), 2.67-2.85 (4H, m), 2.54-2.59 (1H, m), 2.36-2.47 (1H, m), 1.47-2.07 (12H, m), 0.87-1.09 (2H, m).

Example 51

Cyclopentyl (2S)-4-{[2-(3-{5-amino-6-[(2,6-dichlorobenzyl)amino]pyrazin-2-yl}phenyl)ethyl]amino}piperidine-2-carboxylate

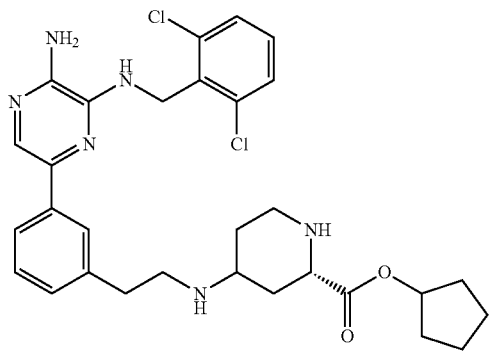 [SMILES: Nc1ncc(-c2cccc(CCNC3CCN[C@H](C(=O)OC4CCCC4)C3)c2)nc1NCc1c(Cl)cccc1Cl]

Cyclopentyl (2S)-4-{[2-(3-{5-amino-6-[(2,6-dichlorobenzyl)amino]pyrazin-2-yl}phenyl) ethyl]amino}piperidine-2-carboxylate was synthesised in a similar manner to Example 50 using Intermediate 23 in stage 1 of the route shown in Scheme 27.

LCMS: purity 94%, m/z 583/585/587 [M+H]+.

1H NMR (300 MHz, DMSO-d6) δ ppm: 7.79 (1H, s), 7.70-7.77 (2H, m), 7.51-7.57 (2H, m), 7.37-7.43 (1H, m), 7.28 (1H, t, J=7.6 Hz), 7.09 (1H, d, J=7.5 Hz), 6.36 (1H, t, J=4.2 Hz), 6.19 (2H, s), 5.05 (1H, t, J=6.1 Hz), 4.82 (2H, d, J=4.1 Hz), 3.14 (1H, dd, J=11.3, 2.1 Hz), 2.89-2.97 (1H, m), 2.67-2.84 (4H, m), 2.54 (1H, br, s), 2.36-2.47 (1H, m), 2.01 (2H, d, J=10.9 Hz), 1.68-1.85 (3H, m), 1.44-1.67 (7H, m), 0.89-1.07 (2H, m).

Example 52

Cyclopentyl 4-[2-(3-{5-amino-6-[(2,6-dichlorobenzyl)amino]pyrazin-2-yl}phenyl)ethyl]piperazine-2-carboxylate

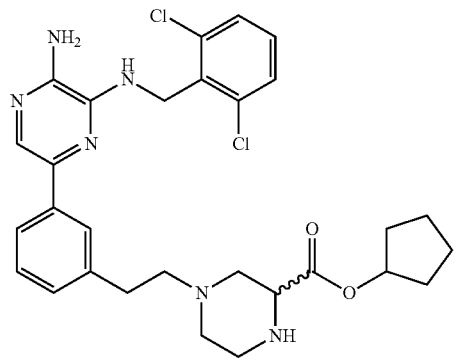 [SMILES: Nc1ncc(-c2cccc(CCN3CCNC(C(=O)OC4CCCC4)C3)c2)nc1NCc1c(Cl)cccc1Cl]

Cyclopentyl 4-[2-(3-{5-amino-6-[(2,6-dichlorobenzyl)amino]pyrazin-2-yl}phenyl)ethyl]piperazine-2-carboxylate was synthesised in a similar manner to Example 50 using Intermediate 28 in stage 1 of the route shown in Scheme 27.

LCMS: purity 97%, m/z 569/571/573 [M+H]+.

1H NMR (300 MHz, DMSO-d6) δ ppm: 7.70-7.81 (3H, m), 7.49-7.57 (2H, m), 7.35-7.44 (1H, m), 7.27 (1H, t, J=7.6 Hz), 7.10 (1H, d, J=7.5 Hz), 6.33-6.40 (1H, m), 6.20 (2H, s), 5.02-5.11 (1H, m), 4.83 (2H, d, J=4.1 Hz), 3.39 (2H, d, J=3.0 Hz), 2.86-2.98 (1H, m), 2.67-2.81 (3H, m), 2.52-2.67 (3H, m), 2.32-2.47 (2H, m), 2.16-2.31 (1H, m), 1.70-1.85 (2H, m), 1.43-1.68 (6H, m).

Example 53

Cyclopentyl (2R)-4-{[(4-{5-amino-6-[(2,6-dichlorobenzyl)amino]pyrazin-2-yl}-1H-pyrazol-1-yl)acetyl]amino}piperidine-2-carboxylate

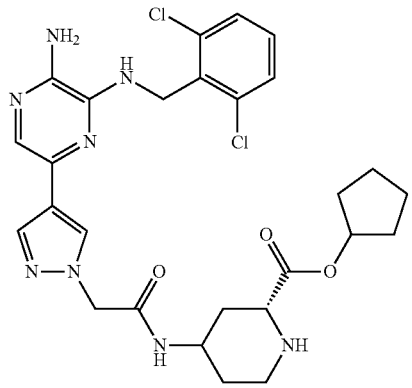 [SMILES: Nc1ncc(-c2cnn(CC(=O)NC3CCN[C@@H](C(=O)OC4CCCC4)C3)c2)nc1NCc1c(Cl)cccc1Cl]

Cyclopentyl (2R)-4-{[(4-{5-amino-6-[(2,6-dichlorobenzyl)amino]pyrazin-2-yl}-1H-pyrazol-1-yl)acetyl]amino}piperidine-2-carboxylate was synthesised as shown in Scheme 28.

Scheme 28

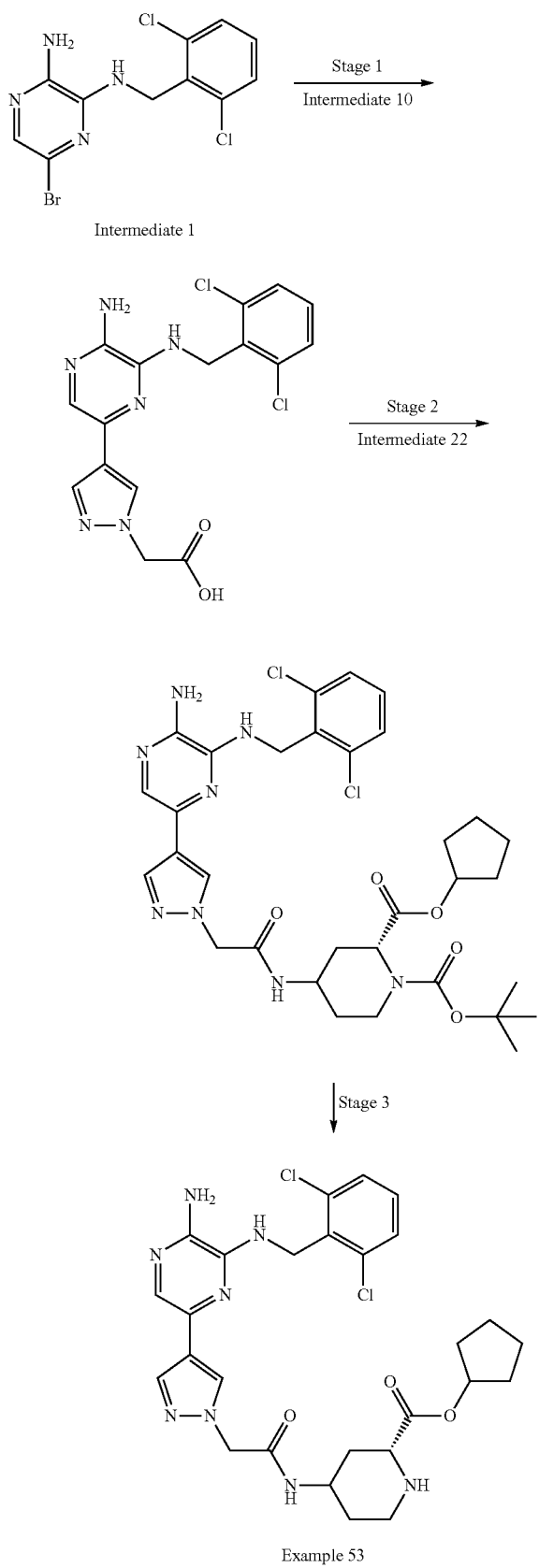

Example 53

Stage 1: (4-{5-Amino-6-[(2,6-dichlorobenzyl)amino]pyrazin-2-yl}-1H-pyrazol-1-yl)acetic acid To a solution of Intermediate 1 (1.34 g, 3.8 mmol) in DME (20 mL), was added Intermediate 10 (956 mg, 4.2 mmol) and 2N Na$_2$CO$_3$ (4.8 mL, 9.6 mmol) and the solution was degassed by bubbling nitrogen through the reaction mixture. Dichlorobis (triphenylphosphine) palladium (II) (270 mg, 0.4 mmol) was added and the reaction was stirred at 90° C. under nitrogen for 18 hrs. The reaction mixture was concentrated in vacuo and the residue was dissolved in water (100 mL) and washed with EtOAc (50 mL). The aqueous was filtered and acidified to pH3 using 1N HCl. The resulting solid was collected by filtration, washed with water and dried in a vacuum oven to give the title compound as a beige solid (400 mg, 26%).

LCMS: m/z 393/395 [M+H]$^+$.

Stage 2: 1-tert-Butyl 2-cyclopentyl (2R)-4-{[(4-{5-amino-6-[(2,6-dichlorobenzyl)amino]pyrazin-2-yl}-1H-pyrazol-1-yl)acetyl]amino}piperidine-1,2-dicarboxylate (4-{5-Amino-6-[(2,6-dichlorobenzyl)amino]pyrazin-2-yl}-1H-pyrazol-1-yl)acetic acid (100 mg, 0.26 mmol) was dissolved in DMF (5 mL) and EDC (59 mg, 0.31 mmol) and HOBt (41 mg, 0.31 mmol) were added. The reaction was stirred for 20 mins after which time Intermediate 22 (95 mg, 0.31 mmol) was added. The reaction was allowed to stir for 72 hours at RT. The reaction mixture was diluted with EtOAc (25 mL) and washed with 2N NaOH (10 mL), water (10 mL), brine (10 mL), dried over MgSO$_4$, filtered and concentrated in vacuo. The crude material was purified by column chromatography (5% MeOH/EtOAc) to give the title compound as a yellow oil (122 mg, 70%).

LCMS: m/z 687/689 [M+H]$^+$.

Stage 3: Cyclopentyl (2R)-4-{[(4-{5-amino-6-[(2,6-dichlorobenzyl)amino]pyrazin-2-yl}-1H-pyrazol-1-yl)acetyl]amino}piperidine-2-carboxylate 1-tert-Butyl 2-cyclopentyl (2R)-4-{[(4-{5-amino-6-[(2,6-dichlorobenzyl)amino]pyrazin-2-yl}-1H-pyrazol-1-yl)acetyl]amino}piperidine-1,2-dicarboxylate (122 mg, 0.18 mmol) was dissolved in DCM (5 mL) and 2N HCl in diethyl ether (20 mL) was added. The reaction mixture was stirred at RT for 1 hrs and then concentrated in vacuo. The crude residue was partitioned between sat Na$_2$CO$_3$ (20 mL) and EtOAc (20 mL). The organics were separated and concentrated in vacuo before purification by preparative HPLC to give the title compound as an off-white solid (41 mg, 39%).

LCMS: purity 98%, m/z 587/589 [M+H]$^+$.

$^1$H NMR (300 MHz, CDCl$_3$) δ ppm: 8.03 (1H, s), 7.92 (1H, s), 7.68 (1H, s), 7.37-7.34 (2H, m), 7.23-7.18 (1H, m), 6.36 (1H, d, J=7.9 Hz), 5.21-5.15 (1H, m), 4.97 (2H, d, J=5.5 Hz), 4.82 (2H, s), 4.59 (1H, t, J=5.5 Hz), 4.22 (2H, br, s), 3.96-3.86 (1H, m), 3.33 (1H, dd, J=2.7, 11.4 Hz), 3.19-3.13 (1H, m), 2.69 (1H, td, J=2.5, 12.4 Hz), 2.27 (1H, d, J=12.2 Hz), 1.89-1.55 (10H+H$_2$O, m), 1.30-1.14 (2H, m).

Example 54 tert-Butyl (2R)-4-{[(4-{5-amino-6-[(2,6-dichlorobenzyl)amino]pyrazin-2-yl}-1H-pyrazol-1-yl)acetyl]amino}piperidine-2-carboxylate

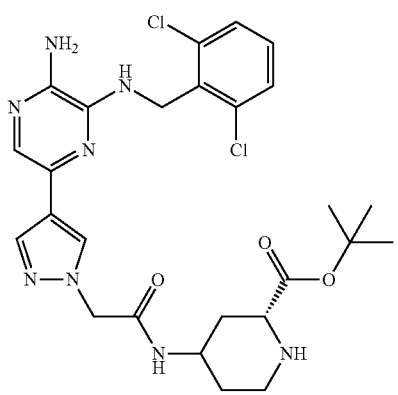 [SMILES: CC(C)(C)OC(=O)[C@H]1CC(NC(=O)Cn2cc(-c3cnc(N)c(NCc4c(Cl)cccc4Cl)n3)cn2)CCN1]

tert-Butyl (2R)-4-{[(4-{5-amino-6-[(2,6-dichlorobenzyl)amino]pyrazin-2-yl}-1H-pyrazol-1-yl)acetyl]amino}piperidine-2-carboxylate was synthesised as shown in Scheme 29.

Scheme 29

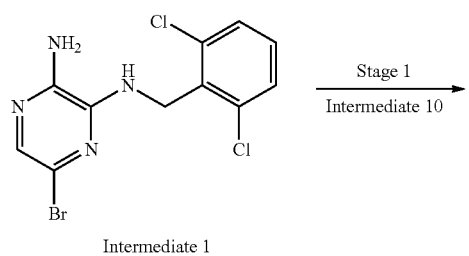

Intermediate 1

Stage 1
Intermediate 10

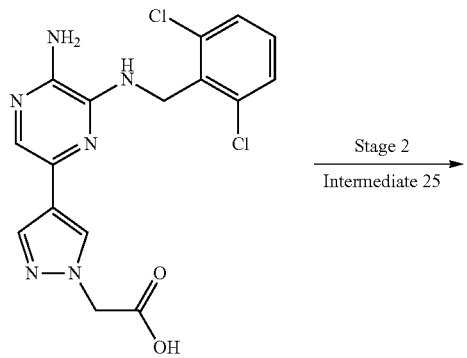

Stage 2
Intermediate 25

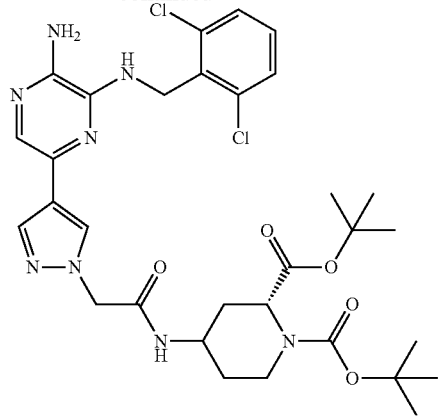

Stage 3

Example 54

Stage 1: (4-{5-Amino-6-[(2,6-dichlorobenzyl)amino]pyrazin-2-yl}-1H-pyrazol-1-yl)acetic acid To a solution of Intermediate 1 (1.34 g, 3.8 mmol) in DME (20 mL), was added Intermediate 10 (956 mg, 4.2 mmol) and 2N Na$_2$CO$_3$ (4.8 mL, 9.6 mmol) and the solution was degassed by bubbling nitrogen through the reaction mixture. Dichlorobis (triphenylphosphine) palladium (II) (270 mg, 0.4 mmol) was added and the reaction was stirred at 90° C. under nitrogen for 18 hrs. The reaction mixture was concentrated in vacuo and the residue was dissolved in water (100 mL) and washed with EtOAc (50 mL). The aqueous was filtered and acidified to pH3 using 1N HCl. The resulting solid was collected by filtration, washed with water and dried in a vacuum oven to give the title compound as a beige solid (400 mg, 26%).
LCMS: m/z 393/395 [M+H]$^+$.

Stage 2: Di-tert-butyl (2R)-4-{[(4-{5-amino-6-[(2,6-dichlorobenzyl)amino]pyrazin-2-yl}-1H-pyrazol-1-yl)acetyl]amino}piperidine-1,2-dicarboxylate (4-{5-Amino-6-[(2,6-dichlorobenzyl)amino]pyrazin-2-yl}-1H-pyrazol-1-yl)acetic acid (100 mg, 0.26 mmol) was dissolved in DMF (5 mL) and EDC (59 mg, 0.31 mmol) and HOBt (41 mg, 0.31 mmol) were added. The reaction was stirred for 20 mins after which time Intermediate 25 (92 mg, 0.31 mmol) was added. The reaction was allowed to stir for 18 hours at RT. The reaction mixture was diluted with EtOAc (25 mL) and washed with 2N NaOH (10 mL), water (10 mL), brine (10 mL), dried over MgSO₄, filtered and concentrated in vacuo. The crude material was purified by column chromatography (5% MeOH/EtOAc) to give the title compound as a yellow solid (150 mg, 87%).

LCMS: m/z 675/677 [M+H]⁺.

Stage 3: tert-Butyl (2R)-4-{[(4-{5-amino-6-[(2,6-dichlorobenzyl)amino]pyrazin-2-yl}-1H-pyrazol-1-yl)acetyl]amino}piperidine-2-carboxylate Di-tert-butyl (2R)-4-{[(4-{5-amino-6-[(2,6-dichlorobenzyl)amino]pyrazin-2-yl}-1H-pyrazol-1-yl)acetyl]amino}piperidine-1,2-dicarboxylate (150 mg, 0.22 mmol) was dissolved in dioxane (10 mL) and the reaction was cooled to 0° C. 4N HCl in dioxane (20 mL) was added. The reaction mixture was stirred at 0° C. for 2 hrs until completion. The reaction was poured onto 2N NaOH (50 mL) and extracted with EtOAc (3×25 mL). The organics were washed with brine (25 mL), dried over MgSO₄, filtered and concentrated in vacuo before purification by preparative HPLC to give the title compound as an off-white solid (10 mg, 8%).

LCMS: purity 96%, m/z 575/577 [M+H]⁺.

¹H NMR (300 MHz, CDCl₃) 8.03 (1H, s), 7.92 (1H, s), 7.69 (1H, s), 7.38-7.35 (2H, m), 7.24-7.19 (1H, m), 6.36 (1H, d, J=7.9 Hz), 4.98 (2H, d, J=5.6 Hz), 4.83 (2H, s), 4.55 (1H, t, J=5.4 Hz), 4.18 (2H, br s), 3.98-3.87 (1H, m), 3.28 (1H, dd, J=2.5, 11.3 Hz), 3.16 (1H, d, J=12.6 Hz), 2.73-2.64 (1H, m), 2.26 (1H, d, J=12.1 Hz), 1.92-1.83 (2H, m), 1.44 (9H, s), 1.29-1.12 (2H, m).

Example 55

Cyclopentyl (2R)-4-{[2-(4-{5-amino-6-[(2,6-dichlorobenzyl)amino]pyrazin-2-yl}-1H-pyrazol-1-yl)ethyl]amino}piperidine-2-carboxylate di-formate

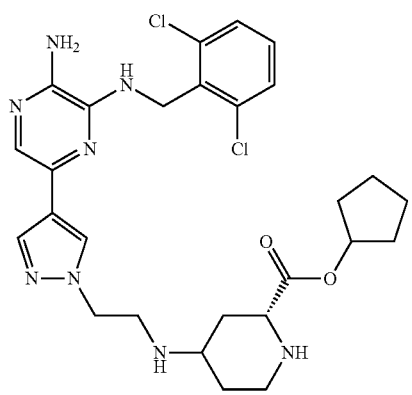 [SMILES: Nc1ncc(-c2cnn(CCNC3CCN[C@@H](C(=O)OC4CCCC4)C3)c2)nc1NCc1c(Cl)cccc1Cl]

Cyclopentyl (2R)-4-{[2-(4-{5-amino-6-[(2,6-dichlorobenzyl)amino]pyrazin-2-yl}-1H-pyrazol-1-yl)ethyl]amino}piperidine-2-carboxylate was synthesised as shown in Scheme 30.

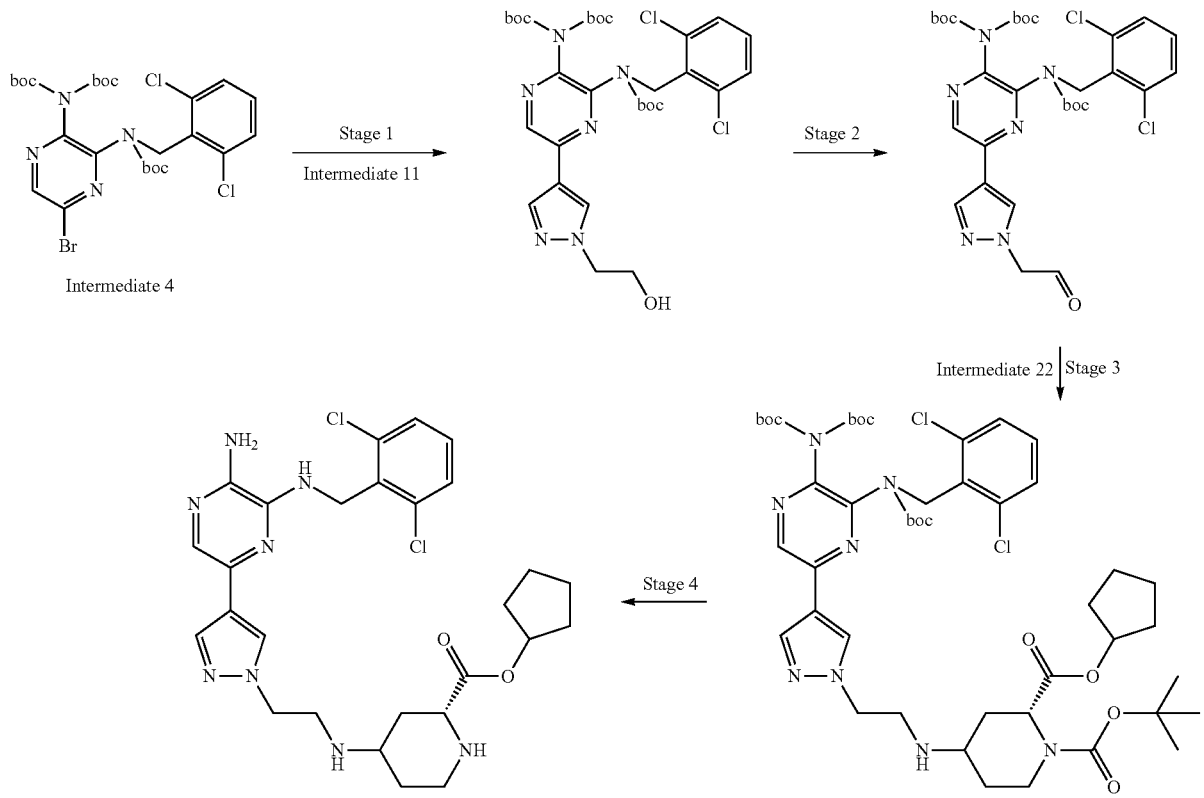

Scheme 30

Stage 1. Di-tert-butyl {3-[(tert-butoxycarbonyl)(2,6-dichlorobenzyl)amino]-5-[1-(2-hydroxyethyl)-1H-pyrazol-4-yl]pyrazin-2-yl}imidodicarbonate To a solution of Intermediate 4 (951 mg, 1.46 mmol) in DME (20 mL), was added Intermediate 11 (524 mg, 2.20 mmol) and 2N Na$_2$CO$_3$ (1.8 mL, 3.65 mmol) and the solution was degassed by bubbling nitrogen through the reaction mixture for 20 mins. Dichlorobis (triphenylphosphine) palladium (II) (270 mg, 0.4 mmol) was added and the reaction was stirred at 80° C. under nitrogen for 5 hrs. The reaction mixture was cooled to RT and diluted was EtOAc (100 mL). The reaction was filtered through Celite® and the filter cake was washed with EtOAc (50 mL). The filtrated was washed with brine (100 mL), dried over MgSO$_4$, filtered, concentrated in vacuo and purified by automated column chromatography using EtOAc in heptane (gradient 10-100%) to give the title compound as an off white solid (920 mg, 93%). LCMS: m/z 579/581/583 [M-Boc]$^+$.

Stage 2. Di-tert-butyl {3-[(tert-butoxycarbonyl)(2,6-dichlorobenzyl)amino]-5-[1-(2-oxoethyl)-1H-pyrazol-4-yl]pyrazin-2-yl}imidodicarbonate To a solution of di-tert-butyl {3-[(tert-butoxycarbonyl)(2,6-dichlorobenzyl)amino]-5-[1-(2-hydroxyethyl)-1H-pyrazol-4-yl]pyrazin-2-yl}imidodicarbonate (900 mg, 1.32 mmol) in DCM (14 mL) at 0° C. was added Dess-Martin periodinone (618 mg, 1.46 mmol). The reaction mixture was stirred with warming to RT under nitrogen for 4 hrs. A further 0.5 eq of Dess-Martin periodinone (300 mg) was added and the reaction stirred for 30 mins. The reaction was diluted with DCM (30 mL), sat NaHCO$_3$ (50 mL) and sat sodium thiosulfate solution (50 mL) were added and vigorously stirred for 1 hr. The aqueous was separated and washed with DCM (100 mL). The combined organics were washed with sat NaHCO$_3$ and sat sodium thiosulfate solution (1:1 mixture, 200 mL), brine (200 mL), dried over MgSO$_4$, filtered and concentrated in vacuo to give the title compound as a yellow solid (830 mg, 93%). The material was taken forward unpurified.

LCMS: m/z 577/579 [M-Boc]$^+$.

Stage 3. 1-tert-Butyl 2-cyclopentyl (2R)-4-{[(4-{5-[bis(tert-butoxycarbonyl)amino]-6-[(tert-butoxycarbonyl)(2,6-dichlorobenzyl)amino]pyrazin-2-yl}-1H-pyrazol-1-yl)acetyl]amino}piperidine-1,2-dicarboxylate Di-tert-butyl {3-[(tert-butoxycarbonyl)(2,6-dichlorobenzyl)amino]-5-[1-(2-oxoethyl)-1H-pyrazol-4-yl]pyrazin-2-yl}imidodicarbonate (100 mg, 0.15 mmol), Intermediate 22 (69 mg, 0.22 mmol) and acetic acid (168 μL, 0.94 mmol) were dissolved in DCE (5 mL) and stirred at RT for 2 hrs. STAB (93 mg, 0.44 mmol) was added and the reaction was stirred for a further 2 hrs until completion. The reaction was diluted with DCM (20 mL) and washed with sat NaHCO$_3$ (20 mL). The aqueous layer was separated and further extracted with DCM (20 mL). The combined organics were dried over MgSO$_4$, filtered, concentrated in vacuo and purified by automated column chromatography using EtOAc in heptane (gradient 0-100%) to give the title compound as a colourless oil (63 mg, 44%).

LCMS: m/z 973/975/977 [M+H]$^+$.

Stage 4. Cyclopentyl (2R)-4-{[2-(4-{5-amino-6-[(2,6-dichlorobenzyl)amino]pyrazin-2-yl}-1H-pyrazol-1-yl)ethyl]amino}piperidine-2-carboxylate To a solution of 1-tert-butyl 2-cyclopentyl (2R)-4-{[(4-{5-[bis(tert-butoxycarbonyl) amino]-6-[(tert-butoxycarbonyl)(2,6-dichlorobenzyl)amino]pyrazin-2-yl}-1H-pyrazol-1-yl)acetyl]amino}piperidine-1,2-dicarboxylate (63 mg, 0.065 mmol) in dioxane (2 ml) was added 4M HCl in dioxane (2 mL) and the reaction was stirred at RT for 17 hrs. The reaction was concentrated in vacuo and the resulting residue was purified by preparative HPLC to give the di-formate salt of the title compound as a brown solid (11.1 mg, 30%).

LCMS purity 96%, m/z 573/575/577 [M+H]$^+$.

$^1$H NMR (300 MHz, CD$_3$OD) δ ppm: 8.57 (2H, br, s), 8.04 (1H, s), 7.92 (1H, s), 7.39-7.57 (3H, m), 7.32 (1H, s), 5.18-5.35 (1H, m), 4.96 (2H, s), 4.28-4.42 (2H, m), 3.77 (1H, d, J=11.1 Hz), 3.21-3.30 (2H, m), 2.82-3.05 (2H, m), 2.35-2.46 (1H, m), 2.03-2.14 (1H, m), 1.83-1.97 (2H, m), 1.74 (9H, br, s)

Example 56

Cyclopentyl (2S)-4-{[2-(4-{5-amino-6-[(2,6-dichlorobenzyl)amino]pyrazin-2-yl}-1H-pyrazol-1-yl)ethyl]amino}piperidine-2-carboxylate di-formate

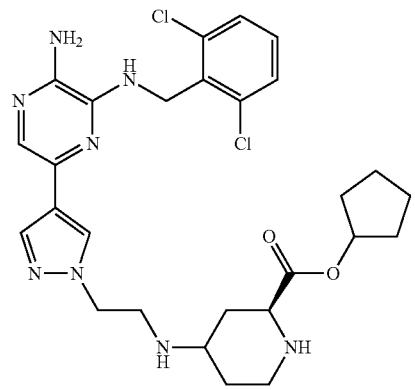 [SMILES: Nc1ncc(-c2cnn(CCNC3CCN[C@H](C(=O)OC4CCCC4)C3)c2)nc1NCc1c(Cl)cccc1Cl]

Cyclopentyl (2S)-4-{[2-(4-{5-amino-6-[(2,6-dichlorobenzyl)amino]pyrazin-2-yl}-1H-pyrazol-1-yl)ethyl]amino}piperidine-2-carboxylate was prepared in a similar manner to Example 55 using Intermediate 23 at Stage 3 of the route shown in Scheme 30.

LCMS: purity 98%, m/z 573/575/577 [M+H]$^+$.

$^1$H NMR (300 MHz, CD$_3$OD) δ ppm: 8.19-8.87 (2H, m), 8.04 (1H, s), 7.92 (1H, s), 7.37-7.56 (3H, m), 7.22-7.36 (1H, m), 5.17-5.33 (1H, m), 4.96 (2H, s), 4.27-4.42 (2H, m), 3.78 (1H, d, J=11.5 Hz), 3.23-3.29 (2H, m), 2.80-3.07 (2H, m), 2.33-2.52 (1H, m), 2.02-2.15 (1H, m), 1.83-2.00 (2H, m), 1.74 (9H, d, J=3.8 Hz).

Example 57

Cyclopentyl N-[2-(4-{5-amino-6-[(2,6-dichlorobenzyl)amino]pyrazin-2-yl}-1H-pyrazol-1-yl)ethyl]-L-leucinate

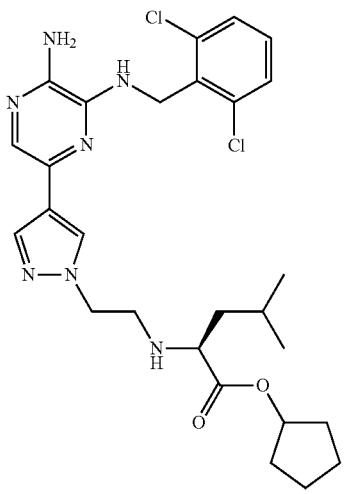 [SMILES: CC(C)C[C@H](NCCn1cc(-c2cnc(N)c(NCc3c(Cl)cccc3Cl)n2)cn1)C(=O)OC1CCCC1]

Cyclopentyl N-[2-(4-{5-amino-6-[(2,6-dichlorobenzyl)amino]pyrazin-2-yl}-1H-pyrazol-1-yl)ethyl]-L-leucinate was prepared in a similar manner to Example 55 using the free base of Intermediate 32 at Stage 3 and DCM as the solvent in Stage 4 of the route shown in Scheme 30. The final product was purified by preparative HPLC.

LCMS: purity 99%, m/z 560/562/564 [M+H]$^+$ $^1$H NMR (300 MHz, CD$_3$OD) δ ppm: 8.06 (1H, s), 7.90 (1H, s), 7.40-7.52 (3H, m), 7.34 (1H, s), 5.10-5.20 (1H, m), 4.95 (2H, s), 4.26 (2H, t, J=5.8 Hz), 3.01-3.19 (2H, m), 2.83-2.96 (1H, m), 1.53-1.90 (9H, m), 1.38-1.47 (2H, m), 0.89 (6H, d, J=2.6 Hz).

Example 58 tert-Butyl N-[2-(4-{5-amino-6-[(2,6-dichlorobenzyl)amino]pyrazin-2-yl}-1H-pyrazol-1-yl)ethyl]-L-leucinate

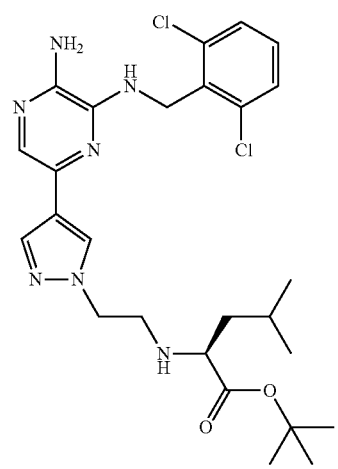 [SMILES: CC(C)C[C@H](NCCn1cc(-c2cnc(N)c(NCc3c(Cl)cccc3Cl)n2)cn1)C(=O)OC(C)(C)C]

tert-Butyl N-[2-(4-{5-amino-6-[(2,6-dichlorobenzyl)amino]pyrazin-2-yl}-1H-pyrazol-1-yl)ethyl]-L-leucinate was prepared in a similar manner to Example 55 using L-leucine tert-butyl ester hydrochloride at Stage 3 and DCM as the solvent in Stage 4 of the route shown in Scheme 30. The final product was purified by preparative HPLC.

LCMS: purity 95%, m/z 548/550/552 (M+H)$^+$.

$^1$H NMR (300 MHz, CDCl$_3$) δ ppm: 8.06 (1H, s), 7.90 (1H, s), 7.40-7.52 (3H, m), 7.34 (1H, s), 5.10-5.20 (1H, m), 4.95 (2H, s), 4.26 (2H, t, J=5.8 Hz), 3.01-3.19 (2H, m), 2.83-2.96 (1H, m), 1.53-1.90 (9H, m), 1.38-1.47 (2H, m), 0.89 (6H, d, J=2.8 Hz).

Example 59

Cyclopentyl 4-[(5-{5-amino-6-[(2,6-dichlorobenzyl)amino]pyrazin-2-yl}pyridin-2-yl)methyl]piperazine-2-carboxylate

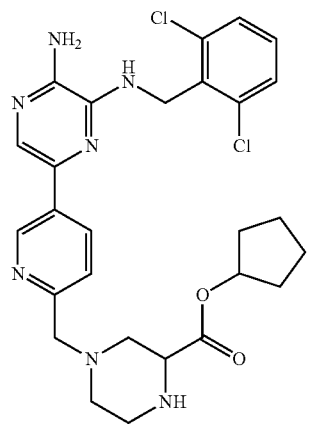 [SMILES: Nc1ncc(-c2ccc(CN3CCNC(C(=O)OC4CCCC4)C3)nc2)nc1NCc1c(Cl)cccc1Cl]

1-tert-Butyl 2-cyclopentyl 4-[(5-{5-[bis(tert-butoxycarbonyl)amino]-6-[(tert-butoxycarbonyl)(2,6-dichlorobenzyl)amino]pyrazin-2-yl}pyridin-2-yl)methyl]piperazine-1,2-dicarboxylate (0.078 g, 0.081 mmol) was stirred with TFA (3 mL) in dichloromethane (3 mL) for 1 h at room temperature. The reaction was concentrated under reduced pressure and the residue was purified by HPLC to give the title compound (28 mg).

LCMS purity 100%, m/z 556/558 [M+H]$^+$.

1H NMR (300 MHz, CDCl$_3$) 9.13 (1H, d, J=1.7 Hz), 8.23 (1H, dd, J=2.3, 8.1 Hz), 7.93 (1H, s), 7.47 (1H, d, J=8.1 Hz), 7.37-7.34 (2H, m), 7.20 (1H, dd, J=7.4, 8.7 Hz), 5.25-5.19 (1H, m), 5.03 (2H, d, J=5.5 Hz), 4.60 (1H, t, J=5.5 Hz), 4.36 (2H, s), 3.77 (1H, d, J=13.9 Hz), 3.67 (1H, d, J=13.9 Hz), 3.58 (1H, dd, J=3.2, 8.1 Hz), 3.13-3.06 (1H, m), 2.99-2.86 (2H, m), 2.69-2.63 (1H, m), 2.53-2.47 (1H, m), 2.39-2.31 (1H, m), 1.89-1.54 (9H, m).

The 1-tert-butyl 2-cyclopentyl 4-[(5-{5-[bis(tert-butoxycarbonyl)amino]-6-[(tert-butoxycarbonyl)(2,6-dichlorobenzyl)amino]pyrazin-2-yl}pyridin-2-yl)methyl]piperazine-1,2-dicarboxylate used in the above process was prepared by the reaction of di-tert-butyl {3-[(tert-butoxycarbonyl)(2,6-difluorobenzyl)amino]-5-(6-formylpyridin-3-yl)pyrazin-2-yl}imidodicarbonate (100 mg, 0.15 mmol) with Intermediate 28 (49 mg, 0.16 mmol) in DCE (5 mL) at room temperature for 1.5 h. Sodium triacetoxyborohydride (63 mg, 0.30 mmol) was then added and stirring was continued at room temperature for 2 h. Saturated aqueous Na$_2$CO$_3$ (20 mL) was added and vigorous stirring continued for 20 min. The reaction was extracted with dichloromethane (3×20 mL), dried (MgSO$_4$) and concentrated under reduced pressure. The residual yellow oil was purified by column chromatography (silica gel; 50% EtOAc in heptanes) to give the desired product (78 mg) as a colourless oil.

LCMS: m/z 956/958 [M+H]$^+$.

The di-tert-butyl {3-[(tert-butoxycarbonyl)(2,6-difluorobenzyl)amino]-5-(6-formylpyridin-3-yl)pyrazin-2-yl}imidodicarbonate used above was prepared by dissolving di-tert-butyl {3-[(tert-butoxycarbonyl)(2,6-dichlorobenzyl)amino]-5-[6-(hydroxymethyl)pyridin-3-yl]pyrazin-2-yl}imidodicarbonate (100 mg, 0.15 mmol) in dichloromethane (5 mL) and adding manganese dioxide (257 mg, 3 mmol). The reaction was stirred at room temperature for 1 h and then filtered through Celite®. The filter pad was washed with dichloromethane (2×10 mL) and the combined filtrates concentrated under reduced pressure to give an orange oil (100 mg) which was used without purification.

The di-tert-butyl {3-[(tert-butoxycarbonyl)(2,6-dichlorobenzyl)amino]-5-[6-(hydroxymethyl)pyridin-3-yl]pyrazin-2-yl}imidodicarbonate used above was prepared by stirring di-tert-butyl {3-[(tert-butoxycarbonyl)(2,6-dichlorobenzyl)amino]-5-[6-({[tert-butyl(dimethyl)silyl]oxy}methyl)pyridin-3-yl]pyrazin-2-yl}imidodicarbonate (1.22 g, 1.5 mmol) with tetrabutylammonium fluoride (3 mL, 3 mmol 1N in THF) in THF (20 mL) at room temperature for 17 h. The reaction was diluted with EtOAc (50 mL) and washed with water (2×50 mL) and brine (1×50 mL). The combined organic layers were dried (MgSO$_4$) and concentrated under reduced pressure. The resulting pale yellow foam was purified by column chromatography (silica gel; 80% EtOAc in heptanes) to give the desired material (809 mg) as a colourless oil which solidified to a white solid on standing. LCMS: m/z 676/678 [M+H]$^+$.

The di-tert-butyl {3-[(tert-butoxycarbonyl)(2,6-dichlorobenzyl)amino]-5-[6-({[tert-butyl(dimethyl)silyl]oxy}methyl)pyridin-3-yl]pyrazin-2-yl}imidodicarbonate used above was prepared from Intermediate 4 (1.0 g, 1.5 mmol) and 2-({[tert-butyl(dimethyl)silyl]oxy}methyl)-5-(4,4,5,5-tetramethyl-1,3,2-dioxaborolan-2-yl)pyridine (0.81 g, 2.3 mmol) which were added to DME (20 mL) and 1.9 mL 2M Na$_2$CO$_3$ and the resulting mixture was then degassed with N$_2$ for 20 min. Dichlorobis(triphenylphosphine)palladium(II) (108 mg, 0.2 mmol) was added to the reaction mixture which was heated at 80° C. for 16 h. The reaction was cooled and diluted with EtOAc (50 mL) and filtered through Celite®. The filter pad was washed with EtOAc (50 mL) and the combined filtrate was washed with brine (1×50 mL), dried MgSO$_4$, and concentrated under reduced pressure. The resulting residue was purified by column chromatography (silica gel, 20% EtOAc in heptane) to give the desired material (1.22 g).

The 2-({[tert-butyl(dimethyl)silyl]oxy}methyl)-5-(4,4,5,5-tetramethyl-1,3,2-dioxaborolan-2-yl)pyridine used in the above process was prepared from 5-bromo-2-({[tert-butyl(dimethyl)silyl]oxy}methyl)pyridine (1.8 g 6.0 mmol), bis(pinacolato)diboron (1.81 g, 7.1 mmol) and PdCl$_2$(dppf)$_2$ (218 mg, 0.3 mmol) in a manner similar to Intermediate 8 to give the desired product (1.1 g) as a pale green oil. LCMS: m/z 268 [M+H]$^+$.

The 5-bromo-2-({[tert-butyl(dimethyl)silyl]oxy}methyl)pyridine used in the above process was prepared from 5-bromo-2-hydroxymethylpyridine (2.5 g, 13 mmol) which was dissolved in DMF (25 mL) and imidazole (1.81 g, 27 mmol) and tert-butyldimethylsilyl chloride (2.20 g, 15 mmol) were added. The reaction mixture was stirred at room temperature for 50 min and then poured into water (50 mL). This was extracted with diethyl ether (3×50 mL) and the combined organic layers were washed with brine (1×50 mL), dried (MgSO$_4$) and concentrated under reduced pressure. The resulting residue was purified by column chromatography (silica gel; 5% EtOAc in heptanes) to give the desired material (3.75 g) as a colourless oil.

LCMS: m/z 302/304 [M+H]$^+$.

Measurement of Biological Activities

CSF1R (FMS) Kinase Activity

The ability of compounds to inhibit CSF1R (FMS) kinase activity was measured in an assay performed by Invitrogen (Paisley, UK). The Z'-LYTE™ biochemical assay employs a fluorescence-based, coupled-enzyme format and is based on the differential sensitivity of phosphorylated and non-phosphorylated peptides to proteolytic cleavage. The peptide substrate is labelled with two fluorophores—one at each end—that make up a FRET pair. In the primary reaction, the kinase transfers the gamma-phosphate of ATP to a single serine or threonine residue in a synthetic FRET-peptide. In the secondary reaction, a site-specific protease recognizes and cleaves non-phosphorylated FRET-peptides. Phosphorylation of FRET-peptides suppresses cleavage by the Development Reagent. Cleavage disrupts FRET between the donor (i.e. coumarin) and acceptor (i.e. fluorescein) fluorophores on the FRET-peptide, whereas uncleaved, phosphorylated FRET-peptides maintain FRET. A radiometric method, which calculates the ratio (the Emission Ratio) of donor emission to acceptor emission after excitation of the donor fluorophore at 400 nm, is used to quantitate reaction progress.

The final 10 μL Kinase Reaction consists of 0.12-12.3 ng CSF1R (FMS), 2 μM Tyr 01 Peptide and ATP in 50 mM HEPES pH 7.5, 0.01% BRIJ-35, 10 mM MgCl$_2$, 1 mM EGTA. The assay is performed at an ATP concentration at, or close to, the Km. After the 60 minute Kinase Reaction incubation at room temperature, 5 μL of a 1:256 dilution of Development Reagent is added. The assay plate is incubated for a further 60 minutes at room temperature and read on a fluorescence plate reader.

Duplicate data points are generated from a ⅓ log dilution series of a stock solution of test compound in DMSO. Nine dilutions steps are made from a top concentration of 10 mM, and a 'no compound' blank is included. Data is collected and analysed using XLfit software from IDBS. The dose response curve is curve fitted to model number 205 (sigmoidal dose-response model). From the curve generated, the concentration giving 50% inhibition is determined and reported.

Macrophage Colony-Stimulating Factor (MCSF)-Stimulation of Human Whole Blood

Whole blood was taken by venous puncture using heparinised vacutainers (Becton Dickinson) and diluted in an equal volume of RPMI1640 tissue culture media (Sigma). 100 μl was plated in V-bottomed 96 well tissue culture treated plates. 2 hours after the addition of the inhibitor in 100 μl of RPMI1640 media, the blood was stimulated with MCSF (Peprotech: #300-25-10 uG) at a final concentration of 50 ng/ml and incubated at 37° C. in 5% CO$_2$ for 22 hrs. MCP-1 levels were measured from cell-free supernatants by sandwich ELISA developed from MCP-1/CCL2 Duoset (R&D Systems #DY279). Additional reagents required for ELISA were purchased from Sigma, (BSA: A3059, 10×PBS: D1408, Tween20: P5927) R&D Systems, (colour reagent: #DY999 and stop solution: #DY994) and Costar (96-well EIA plates: #2592). Assays were carried out following the manufacturer's instructions with the following modifications: Cell-free supernatants were diluted 30:70 in reagent diluent before assay. All incubations except capture antibody were carried out with shaking at 550 rpm. 3 washes were carried out between steps, and incubation times were blocking 1.5 hr, sample/standard and detection antibody incubations 2 hr, HRP incubation 30 min, colour development 20 min.

IC50 values were allocated to one of five ranges as follows:
Range A: IC50<100 nM
Range B: 100 nM<IC50<300 nM
Range C: 300 nM<IC50<1000 nM
Range D: 1000 nM<IC50<5000 nM
Range E: IC50>5000 nM
NT=not tested

| Example | Inhibitor activity versus CSF-1 | Inhibitor activity versus MCP-1 |
|---|---|---|
| 1 | A | C |
| 2 | B | C |
| 3 | B | C |
| 4 | B | NT |
| 5 | A | D |
| 6 | B | C |
| 7 | A | B |
| 8 | A | B |
| 9 | C | A |
| 10 | D | A |
| 11 | C | A |
| 12 | E | NT |
| 13 | D | NT |
| 14 | B | C |
| 15 | E | NT |
| 16 | D | NT |
| 17 | A | NT |
| 18 | B | B |
| 19 | A | A |
| 20 | D | A |
| 21 | A | C |
| 22 | A | C |
| 23 | C | C |
| 24 | C | NT |
| 25 | B | C |
| 26 | A | C |
| 27 | B | A |
| 28 | B | A |
| 29 | NT | D |
| 30 | B | B |
| 31 | B | A |
| 32 | B | D |
| 33 | B | D |
| 34 | A | B |
| 35 | A | C |
| 36 | C | B |
| 37 | C | A |
| 38 | E | E |
| 39 | E | E |
| 40 | E | D |
| 41 | D | NT |
| 42 | E | C |
| 43 | E | E |
| 44 | E | E |
| 45 | D | D |
| 46 | A | C |
| 47 | A | C |
| 48 | D | C |
| 49 | D | D |
| 50 | A | B |
| 51 | A | B |
| 52 | NT | B |
| 53 | B | NT |
| 54 | B | NT |
| 55 | B | B |
| 56 | B | C |
| 57 | D | D |
| 58 | E | E |
| 59 | B | NT |

The invention claimed is:

1. A compound which is an amino acid or amino acid ester of formula (I) or a salt, N-oxide, hydrate or solvate thereof:

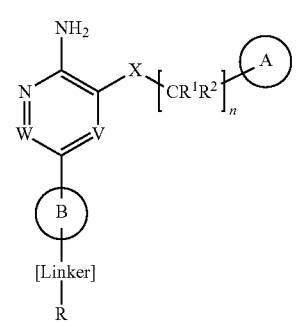

(I)

wherein:
ring A is a phenyl or a 5- to 6-membered heterocyclyl group, said ring A group being unsubstituted or substituted by 1, 2 or 3 substituents which are the same or different and are selected from halogen atoms and unsubstituted $C_{1-4}$ alkyl, $C_{1-4}$ alkoxy, hydroxyl, $C_{1-4}$ haloalkyl, $C_{1-4}$ haloalkoxy, $C_{1-4}$ hydroxyalkyl, cyano, nitro, $-SR^3$ and $-NR^3R^4$ groups,
wherein $R^3$ and $R^4$ are the same or different and represent hydrogen or unsubstituted $C_{1-2}$alkyl;
$R^1$ and $R^2$ independently represent hydrogen, halogen or unsubstituted $C_{1-4}$ alkyl;
n is 1;
X is NH;
V is $-N=$ and W is $-C(Z)=$;
Z is hydrogen, fluoro, chloro or unsubstituted $C_{1-3}$alkyl;
ring B is a 1,4-phenylene, 1,3-phenylene or pyridinyl group;
[Linker] represents a group of formula $-(CH_2)_m-X^1-L^1-Y^1-$ wherein:
m is 0, 1, 2 or 3;
$X^1$ represents a bond, $-O-$, $-S-$, $-NR^7-$, $-C(=O)-$, $-C(=O)O-$, $-OC(=O)-$, $-S(=O)_2-$; $-NR^5C(=O)-$, $-C(=O)NR^5-$, $-NR^5C(=O)NR^6-$, $-NR^5S(=O)_2-$, or $-S(=O)_2NR^5-$ wherein $R^5$ and $R^6$ are independently hydrogen or $C_{1-6}$ alkyl and $R^7$ represents hydrogen, unsubstituted $C_{1-4}$ alkyl or $-C(=O)CH_3$;
$L^1$ represents a divalent radical of formula $-(Alk^1)_x-(Q)_y-(Het)_w-(Alk^2)_z-$ or $-(Alk^1)_x-(Het)_w-(Q)_y-(Alk^2)_z-$ wherein
x, y, w and z are independently 0 or 1;
Q represents a divalent $C_{6-12}$ aryl, 5- to 12-membered heterocyclyl or $C_{3-7}$ carbocyclyl ring;
Het represents $-O-$, $-S-$ or $-NR^7-$ wherein $R^7$ represents hydrogen, unsubstituted $C_{1-4}$ alkyl or $-C(=O)CH_3$;
$Alk^1$ and $Alk^2$ independently represent divalent $C_{3-7}$ cycloalkyl radicals, or straight or branched, $C_{1-6}$ alkylene, $C_{2-6}$ alkenylene, or $C_{2-6}$ alkynylene radicals;

$Y^1$ represents a bond, —O—, —S—, —NR$^7$—, —C(=O)—, —C(=O)O—, —OC(=O)—, —S(=O)$_2$—, —NR$^5$C(=O)—, —C(=O)NR$^5$—, —NR$^5$C(=O)NR$^6$—, —NR$^5$S(=O)$_2$—, or —S(=O)$_2$NR$^5$—, wherein R$^5$ and R$^6$ are independently hydrogen or C$_{1-6}$ alkyl and R$^7$ represents hydrogen, unsubstituted C$_{1-4}$ alkyl or —C(=O)CH$_3$;

R represents a group of formula (X) or (Y):

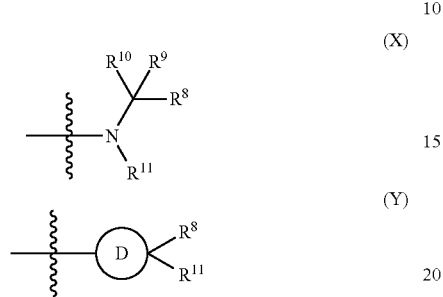

in which:

R$^8$ is a group —COOH or an ester group of formula —(C=O)OR$^{14}$ wherein R$^{14}$ is R$^{15}$R$^{16}$R$^{17}$C— wherein (i) R$^{15}$ is hydrogen, fluorine or optionally substituted C$_{1-3}$alkyl-(Z$^1$)$_a$-[(C$_1$-C$_3$)alkyl]$_b$- or C$_{2-3}$alkenyl-(Z$^1$)$_a$-[C$_{1-3}$alkyl]$_b$- wherein a and b are independently 0 or 1 and Z$^1$ is —O—, —S—, or —NR$^{18}$— wherein R$^{18}$ is hydrogen or C$_{1-3}$ alkyl; and R$^{16}$ and R$^{17}$ are independently hydrogen or C$_{1-3}$ alkyl-;

(ii) R$^{15}$ is hydrogen or optionally substituted R$^{19}$R$^{20}$N-C$_{1-3}$alkyl- wherein R$^{19}$ is hydrogen or C$_{1-3}$alkyl and R$^{20}$ is hydrogen or C$_{1-3}$alkyl; or R$^{19}$ and R$^{20}$ together with the nitrogen to which they are attached form an optionally substituted monocyclic heterocyclic ring of 5- or 6-ring atoms or bicyclic heterocyclic ring system of 8 to 10ring atoms, and R$^{16}$ and R$^{17}$ are independently hydrogen or C$_{1-3}$alkyl-; or (iii) R$^{15}$ and R$^{16}$ taken together with the carbon to which they are attached form an optionally substituted monocyclic carbocyclic ring of from 3 to 7 ring atoms or bycyclic carbocyclic ring system of 8 to 10 ring atoms, and R$^{17}$ is hydrogen; or (iv) R$^{15}$ and R$^{16}$ taken together with the carbon to which they are attached form an optionally substituted monocyclic heterocyclic ring of from 3 to 7 ring atoms wherein at least one ring atom is selected from —O—, —S—, or—NR$^{18}$— wherein R$^{18}$ is hydrogen or C$_{1-3}$alkyl,or a bicyclic heterocyclic ring system of 8 to 10 ring atoms wherein at least one ring atom is slected from —O—, —S—, or—NR$^{18}$—wherein R$^{18}$ is hydrogen or C$_{1-3}$alkyl, and R$^{17}$ is hydrogen;

R$^9$ and R$^{10}$ are the same or different and each represents the side chain of a natural amino acid or:
(a) a hydrogen atom;
(b) a C$_{1-6}$ alkyl group;
(c) R$^9$ and R$^{10}$, taken together with the carbon to which they are attached, form a 3- to 6-membered saturated spiro cycloalkyl ring;
(d) a group -L$^2$-B$^1$, in which L$^2$ represents a bond or a C$_{1-6}$ alkylene group and B$^1$ represents a C$_{6-10}$ aryl or 5- to 10-membered heteroaryl group; or (e) a group selected from indol-3-ylmethyl, —CH$_2$COOH, —CH$_2$CH$_2$COOH, —CH$_2$CONH$_2$, —CH$_2$CH$_2$CONH$_2$, —CH$_2$CH$_2$CH$_2$NHC(NH)NH$_2$, cyclohexyl, cyclohexylmethyl and 1-benzylthio-1-methyletheyl, wherein:

said C$_{1-6}$ alkyl group in (b) is unsubstituted or substituted with 1 or 2 substituents which are the same or different and represent halogen, C$_{1-4}$ alkoxy, C$_{1-2}$ haloalkyl, hydroxyl, —COOR$^3$, —COONR$^3$R$^4$, —SR$^3$ and —NR$^3$R$^4$ wherein R$^3$ and R$^4$ are the same or different and represent hydrogen or unsubstituted C$_{1-2}$ alkyl;

said C$_{1-6}$ alkylene group in (d) is unsubstituted or substituted with 1, 2 or 3unsubstituted substituents which are the same or different and are selected from halogen atoms and C$_{1-4}$ alkoxy, hydroxyl, C$_{1-2}$ haloalkyl and —NR$^3$R$^4$ groups where R$^3$and R$^4$ are the same or different and represent hydrogen or unsubstituted C$_{1-2}$ alkyl; and said C$_{6-10}$ aryl or 5-or 10-membered heteroaryl group in (d)is unsubstituted or substituted by 1, 2 or 3 substituents which are the same or different and are selected from halogen atoms and unsubstituted C$_{1-4}$ alkyl, C$_{1-4}$ alkoxy, hydroxyl, C$_{1-4}$haloalkyl, C$_{1-4}$ haloalkoxy, C$_{1-4}$ hydroalkyl, cyano, nitro, —SR$^3$ and —NR$^3$R$^4$ groups where R$^3$ and R$^4$ are the same or different and represent hydrogen or unsubstituted C$_{1-2}$ alkyl;

R$^{11}$ represents a hydrogen atom or a C$_{1-4}$ alkyl group;

ring D is a 5- to 7-membered saturated heterocyclyl group having at least one nitrogen atom in the ring, wherein R$^8$ and R$^{11}$ are linked to a ring carbon adjacent to a ring nitrogen, and wherein the bond shown intersected by a wavy line may be from a nitrogen atom or a carbon atom in ring D;

wherein when R is (X), [Linker] is not connected to (X) via an O, N or S atom;

and wherein, unless otherwise stated:

any alkyl, alkenyl and alkynyl groups and moieties in R$^5$, R$^6$, R$^{15}$, R$^{16}$, R$^{17}$, R$^{18}$, R$^{19}$, R$^{20}$, R$^{11}$, Alk$^1$ and Alk$^2$ are the same or different and are each unsubstituted or substituted with 1, 2 or 3 unsubstituted substituents which are the same or different and are selected from halogen atoms and C$_{1-4}$ alkoxy, C$_{2-4}$ alkenyloxy, C$_{1-4}$ haloalkoxy, C$_{2-4}$ haloalkenyloxy, hydroxyl, —SR$^3$, cyano, nitro and —NR$^3$R$^4$ groups, wherein R$^3$ and R$^4$ are the same or different and represent hydrogen or unsubstituted C$_{1-2}$ alkyl;

any aryl, heterocyclyl, cycloalkyl and carbocyclyl groups and moieties in rings B, Q, D, Alk$^1$ and Alk$^2$ and the rings formed by R$^9$ and R$^{10}$, by R$^{15}$ and R$^{16}$ and by R$^{19}$ and R$^{20}$ are the same or different and are each unsubstituted or substituted by 1, 2, 3 or 4 unsubstituted substituents selected from halogen atoms, and cyano, nitro, C$_{1-4}$ alkyl, C$_{1-4}$ alkoxy, C$_{2-4}$ alkenyl, C$_{2-4}$ alkenyloxy, C$_{1-4}$ haloalkyl, C$_{2-4}$ haloalkenyl, C$_{1-4}$ haloalkoxy, C$_{2-4}$ haloalkenyloxy, hydroxyl, C$_{1-4}$ hydroxyalkyl, —SR$^3$ and —NR$^3$R$^4$ groups wherein each R$^3$ and R$^4$ is the same or different and represents hydrogen or unsubstituted C$_{1-2}$ alkyl, or from substituents of formula —COOR$^{12}$, —COR$^{12}$, —SO$_2$R$^{12}$, —CONR$^{12}$R$^{13}$, —SO$_2$NR$^{12}$R$^{13}$, —OCONR$^{12}$R$^{13}$, —NR$^{12}$COR$^{13}$, —NR$^{12}$COOR$^{13}$, —NR$^{12}$SO$_2$R$^{13}$, —NR$^{12}$SO$_2$OR$^{13}$ or —NR$^{12}$CONR$^{12}$R$^{13}$ wherein R$^{12}$ and R$^{13}$ are the same or different and represent hydrogen or unsubstituted $C_{1-4}$ alkyl, or $R^{12}$ and $R^{13}$ when attached to the same nitrogen atom form a non-fused 5- or 6-membered heterocyclyl group.

2. A compound as claimed in claim 1, wherein ring B is unsubstituted or substituted by 1, 2 or 3 substituents which are the same or different and are selected from halogen atoms and unsubstituted $C_{1-4}$ alkyl, $C_{1-4}$ alkoxy, hydroxyl, $C_{1-4}$ haloalkyl, $C_{1-4}$ haloalkoxy, $C_{1-4}$ hydroxyalkyl, cyano, nitro, —$SR^3$ and —$NR^3R^4$ groups, wherein $R^3$ and $R^4$ are the same or different and represent hydrogen or unsubstituted $C_{1-2}$ alkyl.

3. A compound as claimed in claim 1, wherein either $R^{15}$ is hydrogen or $C_{1-3}$alkyl-$(Z^1)_a$—$[(C_1\text{-}C_3)$alkyl$]_b$- wherein a and b are independently 0 or 1 and $Z^1$ is —O—, —S—, or —NH— and $R^{16}$ and $R^{17}$ are independently hydrogen or $C_{1-3}$ alkyl-; or $R^{15}$ and $R^{16}$ taken together with the carbon to which they are attached form a 3- to 7-membered cycloalkyl ring and $R^{17}$ is hydrogen.

4. A compound as claimed in claim 1, wherein either $R^{14}$ is cyclopentyl or t-butyl.

5. A compound as claimed in claim 1, wherein (i) $R^9$ and $R^{10}$ are side chains of natural amino acids, (ii) one of $R^9$ and $R^{10}$ is hydrogen or unsubstituted $C_{1-4}$ alkyl and the other is an unsubstituted $C_{1-6}$ alkyl group or a $C_{1-6}$ alkyl group substituted with a $C_{1-4}$ alkoxy group, or (iii) $R^9$ and $R^{10}$, taken together with the carbon to which they are attached, form a saturated spiro cyclobutyl ring.

6. A compound as claimed in claim 1, wherein R represents a group of formula (Y1):

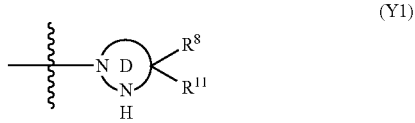

wherein ring D is a is a 5- to 7-membered saturated heterocyclyl group having at least two nitrogen atoms in the ring, wherein $R^8$ and $R^{11}$ are linked to a ring carbon adjacent to a ring nitrogen, and wherein the bond shown intersected by a wavy line is from a nitrogen atom in ring D.

7. A compound as claimed in claim 1, wherein R represents a group of formula (Y2):

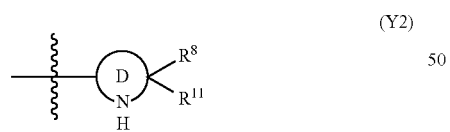

wherein ring D is a is a 5- to 7-membered saturated heterocyclyl group having at least one nitrogen atom in the ring, wherein $R^8$ and $R^{11}$ are linked to a ring carbon adjacent to a ring nitrogen, and wherein the bond shown intersected by a wavy line is from a carbon atom in ring D.

8. A compound according to claim 7, wherein [Linker] represents —$(CH_2)_m$—$X^1$-$(Alk^1)_x$-$Y^1$, wherein m is 0, 1, 2 or 3, x is 0 or 1, $Alk^1$ is an unsubstituted $C_{1-3}$ alkylene group, and $X^1$ and $Y^1$ independently represent a bond, —O—, —S—, —$NR^7$—, —C(=O)— or —C(=O)$NR^5$—, wherein $R^5$ is hydrogen or $C_{1-4}$ alkyl and $R^7$ represents hydrogen, unsubstituted $C_{1-4}$ alkyl or —C(=O)$CH_3$.

9. A compound as claimed in claim 1, wherein:
$R^1$ and $R^2$ each represent hydrogen; and
ring B represents a 1,4-phenylene, 1,3-phenylene or pyridinyl group, said ring B group being unsubstituted or substituted by 1, 2 or 3 substituents which are the same or different and are selected from halogen atoms and unsubstituted $C_{1-4}$ alkyl, $C_{1-4}$ alkoxy, hydroxyl, $C_{1-4}$ haloalkyl, $C_{1-4}$ haloalkoxy, $C_{1-4}$ hydroxyalkyl, cyano, nitro, —$SR^3$ and —$NR^3R^4$ groups, wherein $R^3$ and $R^4$ are the same or different and represent hydrogen or unsubstituted $C_{1-2}$ alkyl.

10. A compound according to claim 9, wherein
R represents a group of formula (X);
$R^8$ is a group —COOH or an ester group of formula —C(=O)$OR^{14}$ wherein $R^{14}$ is $R^{15}R^{16}R^{17}C$— wherein either $R^{15}$ is hydrogen or $C_{1-3}$alkyl-$(Z^1)_a$—$[(C_1\text{-}C_3)$alkyl$]_b$- wherein a and b are independently 0 or 1 and $Z^1$ is —O—, —S—, or —NH— and $R^{16}$ and $R^{17}$ are independently hydrogen or $C_{1-3}$ alkyl-; or $R^{15}$ and $R^{16}$ taken together with the carbon to which they are attached form a 3- to 7-membered cycloalkyl ring and $R^{17}$ is hydrogen;
$R^9$ and $R^{10}$ are side chains of natural amino acids or one of $R^9$ and $R^{10}$ is hydrogen or unsubstituted $C_{1-4}$ alkyl and the other is an unsubstituted $C_{1-6}$ alkyl group;
$R^{11}$ represents a hydrogen atom or an unsubstituted $C_{1-2}$ alkyl group;
[Linker] represents —$(CH_2)_m$—$X^1$-$(Alk^1)$- or —$(CH_2)_v$—, wherein v is 1 or 2, m is 0, 1, 2 or 3; $Alk^1$ is an unsubstituted $C_{1-3}$ alkylene group and $X^1$ is a bond, —O—, —S—, —$NR^7$—, —C(=O)— or —C(=O)$NR^5$—, wherein $R^5$ is hydrogen or $C_{1-4}$ alkyl and $R^7$ represents hydrogen, unsubstituted $C_{1-4}$ alkyl or —C(=O)$CH_3$.

11. A compound as claimed in claim 1, wherein:
ring A represents a phenyl group, said ring A group being unsubstituted or substituted by 1, 2 or 3 substituents which are the same or different and are selected from halogen atoms and unsubstituted $C_{1-4}$ alkyl, $C_{1-4}$ alkoxy, hydroxyl and —$NR^3R^4$ groups, wherein $R^3$ and $R^4$ are the same or different and represent hydrogen or unsubstituted $C_{1-2}$ alkyl;
$R^1$ and $R^2$ each represent hydrogen;
W is —C(H)=; and
ring B represents a 1,4-phenylene or 1,3-phenylene group, said ring B group being unsubstituted or substituted by 1, 2 or 3 substituents which are the same or different and are selected from halogen atoms and unsubstituted $C_{1-4}$ alkyl, $C_{1-4}$ alkoxy, hydroxyl and —$NR^3R^4$ groups, wherein $R^3$ and $R^4$ are the same or different and represent hydrogen or unsubstituted $C_{1-2}$ alkyl.

12. A compound as claimed in claim 11, wherein:
(a)
R represents a group of formula (Y1'):

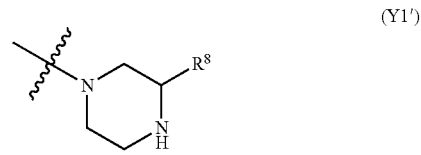

$R^8$ is a group —COOH or an ester group of formula —C(=O)$OR^{14}$ wherein $R^{14}$ is $R^{15}R^{16}R^{17}C$— wherein either $R^{15}$ is hydrogen or $C_{1-3}$alkyl-$(Z^1)_a$—

[(C$_1$-C$_3$)alkyl]$_b$- wherein a and b are independently 0 or 1 and Z$^1$ is —O—, —S—, or —NH— and R$^{16}$ and R$^{17}$ are independently hydrogen or C$_{1-3}$ alkyl-; or R$^{15}$ and R$^{16}$ taken together with the carbon to which they are attached form a 3- to 7-membered cycloalkyl ring and R$^{17}$ is hydrogen;

[Linker] is —(CH$_2$)$_v$— and —C(=O)—, wherein v is 1 or 2; or (b)
R represents a group of formula (Y2'):

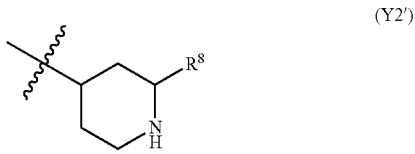

(Y2')

R$^8$ is a group —COOH or an ester group of formula —(C=O)OR$^{14}$ wherein R$^{14}$ is R$^{15}$R$^{16}$R$^{17}$C— wherein either R$^{15}$ is hydrogen or C$_{1-3}$alkyl-(Z$^1$)$_a$—[(C$_1$-C$_3$)alkyl]$_b$- wherein a and b are independently 0 or 1 and Z$^1$ is —O—, —S—, or —NH— and R$^{16}$ and R$^{17}$ are independently hydrogen or C$_{1-3}$ alkyl-; or R$^{15}$ and R$^{16}$ taken together with the carbon to which they are attached form a 3- to 7-membered cycloalkyl ring and R$^{17}$ is hydrogen;

[Linker] is —C(=O)NR$^7$—, —CH$_2$NR$^7$— or —CH$_2$C(=O)NR$^7$—, wherein R$^7$ represents hydrogen, unsubstituted methyl, unsubstituted ethyl, unsubstituted isobutyl or —C(=O)CH$_3$.

13. A compound as claimed in claim 1, which is:
Cyclopentyl (2R)-4-[(4-{5-amino-6-[(2,6-dichlorobenzyl)amino]pyrazin-2-yl}benzyl)amino]piperidine-2-carboxylate;
Cyclopentyl 4-(4-{5-amino-6-[(2,6-dichlorobenzyl)amino]pyrazin-2-yl}benzyl)piperazine-2-carboxylate;
Cyclopentyl (2S)-4-(4-{5-amino-6-[(2,6-dichlorobenzyl)amino]pyrazin-2-yl}benzyl)piperazine-2-carboxylate;
Cyclopentyl (2R)-4-(4-{5-amino-6-[(2,6-dichlorobenzyl)amino]pyrazin-2-yl}benzyl)piperazine-2-carboxylate;
Cyclopentyl (2R)-4-[(4-{5-amino-6-[(2,6-dichlorobenzyl)amino]pyrazin-2-yl}-2-chlorobenzyl)amino]piperidine-2-carboxylate;
Cyclopentyl (2R)-4-[(4-{5-amino-6-[(2,6-dichlorobenzyl)amino]pyrazin-2-yl}benzyl)(ethyl)amino]piperidine-2-carboxylate;
Cyclopentyl (2R)-4-[(4-{5-amino-6-[(2,6-dichlorobenzyl)amino]pyrazin-2-yl}benzyl)(methyl)amino]piperidine-2-carboxylate;
tert-Butyl (2R)-4-[(4-{5-amino-6-[(2,6-dichlorobenzyl)amino]pyrazin-2-yl}benzyl)(ethyl)amino]piperidine-2-carboxylate;
Cyclopentyl (2R)-4-[acetyl(4-{5-amino-6-[(2,6-dichlorobenzyl)amino]pyrazin-2-yl}benzyl)amino]piperidine-2-carboxylate;
Cyclopentyl (2R)-4-(3-{5-amino-6-[(2,6-dichlorobenzyl)amino]pyrazin-2-yl}benzyl)piperazine-2-carboxylate;
Cyclopentyl 1-[(3-{5-amino-6-[(2,6-dichlorobenzyl)amino]pyrazin-2-yl}benzyl)amino]cyclobutanecarboxylate;
Cyclopentyl N-[2-(3-{5-amino-6-[(2,6-dichlorobenzyl)amino]pyrazin-2-yl}phenyl)ethyl]-2-methylalaninate;
Cyclopentyl 4-(4-{5-amino-6-[(2,6-dichlorobenzyl)amino]pyrazin-2-yl}-2-ethylbenzyl)piperazine-2-carboxylate; or Cyclopentyl (2S)-4-(3-{5-amino-6-[(2,6-dichlorobenzyl)amino]pyrazin-2-yl}benzyl)piperazine-2-carboxylate.

14. A pharmaceutical composition which comprises a compound as defined in claim 1 and one or more pharmaceutically acceptable carrier(s) and/or excipients.

15. A compound as claimed in claim 9, wherein Z represents hydrogen.

16. A compound according to claim 9, wherein:
R represents a group of formula (Y1):

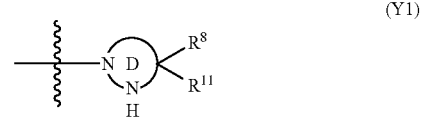

(Y1)

wherein ring D is a is a 5- to 7-membered saturated heterocyclyl group having at least two nitrogen atoms in the ring, wherein R$^8$ and R$^{11}$ are linked to a ring carbon adjacent to a ring nitrogen, and wherein the bond shown intersected by a wavy line is fom a nitrogen atom in ring D;

R$^8$ is a group —COOH or an ester group of formula —(C=O)OR$^{14}$ wherein R$^{14}$ is R$^{15}$R$^{16}$R$^{17}$C—wherein either R$^{15}$ is hydrogen or C$_{1-3}$alkyl-(Z$^1$)$_a$—[(C$_1$-C$_3$)alkyl]$_b$- wherein a and b are independently 0 or 1 and Z$^1$ is —O—, —S—, or —NH— and R$^{16}$ and R$^{17}$ are independently hydrogen or C$_{1-3}$ alkyl-; or R$^{15}$ and R$^{16}$ taken together with the carbon to which they are attached form a 3- to 7-membered cycloalkyl ring and R$^{17}$ is hydrogen;

R$^{11}$ represents a hydrogen atom or an unsubstituted C$_{1-2}$ alkyl group;

[Linker] is —(CH$_2$)$_m$—X$^1$-Alk$^1$)$_x$- or —(CH$_2$)$_v$—, wherein v is 1 or 2, m is 0, 1, 2 or 3; x is 0 or 1; Alk$^1$ is an unsubstituted C$_{1-3}$ alkylene group; and X$^1$ is a bond, —O—, —S—, —NR$^7$—, —C(=O)— or —C(=O)NR$^5$—, wherein R$^5$ is hydrogen or C$_{1-4}$ alkyl and R$^7$ represents hydrogen, unsubstituted C$_{1-4}$ alkyl or —C(=O)CH$_3$, wherein when x is 0, X$^1$ is a bond or C(=O).

17. A compound according to claim 9, wherein:
R represents a group of formula (Y2):

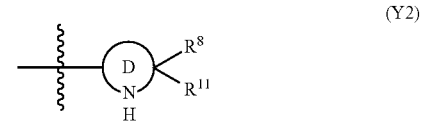

(Y2)

wherein ring D is a is a 5- to 7-membered saturated heterocyclyl group having at least one nitrogen atom in the ring, wherein R$^8$ and R$^{11}$ are linked to a ring carbon adjacent to a ring nitrogen, and wherein the bond shown intersected by a wavy line is fom a nitrogen atom in ring D;

R$^8$ is a group —COOH or an ester group of formula —(C=O)OR$^{14}$ wherein R$^{14}$ is R$^{15}$R$^{16}$R$^{17}$C—wherein either R$^{15}$ is hydrogen or C$_{1-3}$alkyl-(Z$^1$)$_a$—[(C$_1$-C$_3$)alkyl]$_b$- wherein a and b are independently 0 or 1 and Z$^1$ is —O—, —S—, or —NH— and R$^{16}$ and R$^{17}$ are independently hydrogen or C$_{1-3}$ alkyl-; or R$^{15}$ and R$^{16}$ taken together with the carbon to which they are attached form a 3- to 7-membered cycloalkyl ring and R$^{17}$ is hydrogen;

$R^{11}$ represents a hydrogen atom or an unsubstituted $C_{1-2}$ alkyl group;

[Linker] represents $-(CH_2)_m-X^1-(Alk^1)_x-Y^1$, wherein m is 0, 1, 2 or 3; x is 0 or 1; $X^1$ is a bond or $-C(=O)$; $Alk^1$ is an unsubstituted $C_{1-3}$ alkylene group; and $Y^1$ is a bond or $-NR^7-$, wherein $R^7$ represents hydrogen, unsubstituted $C_{1-4}$ alkyl or $-C(=O)CH_3$.

* * * * *